US005955289A

United States Patent [19]
Ma et al.

[11] Patent Number: 5,955,289
[45] Date of Patent: Sep. 21, 1999

[54] ASSAYS FOR NONGENOTOXIC, CHEMICAL CARCINOGENS

[75] Inventors: Xinfang Ma; Joseph A. Rininger, both of Ithaca; Brian E. Johnson, Spencer; Debra S. Whiting, Valois, all of N.Y.

[73] Assignee: Brown, Pinnisi & Michaels, PC, Ithaca, N.Y.

[21] Appl. No.: 08/400,401

[22] Filed: Mar. 7, 1995

Related U.S. Application Data

[63] Continuation of application No. 08/075,744, Jun. 11, 1993, abandoned, which is a continuation-in-part of application No. 08/007,636, Jan. 21, 1993, abandoned.

[51] Int. Cl.$^6$ ........................ G01N 33/567; G01N 33/53; G01N 33/574; G01N 33/48
[52] U.S. Cl. ........................ 435/7.21; 435/7.1; 435/7.23; 435/7.9; 435/7.92; 436/63; 436/64; 530/387.1
[58] Field of Search ............................... 435/6, 7.1, 7.21, 435/7.23, 7.4, 15, 183, 7.9, 7.92; 436/63, 64; 530/387.1

[56] References Cited

U.S. PATENT DOCUMENTS 5,294,538  3/1994  Beach ........................................ 435/21

OTHER PUBLICATIONS

Farber, E. (1984) "The Multistep Nature of Cancer Development". Cancer Res. 44, pp. 4217–4223.
Kanduc, D. et al (1992) "Effect of MNU on the Methylation Pattern of Hepatic DNA During Compensatory Cell Proliferation". Biochem. Biophys. Res. Commun. 184, pp. 107–111.
Ames, B.N. (1984) "The Detection of Environmental Mutagens and Potential Carcinogens". Cancer 53, pp. 2034–2040.
McCann, J. et al (1976) "Detection of Carcinogens as Mutagens in the Salmonella/Microsome Test: Assay of 300 Chemicals: Discussion". Proc. Natl. Acad. Sci. U.S.A. 73, pp. 950–954.
Ames, B.N. et al (1973) "Carcinogens Are Mutagens: A Simple Test System Combining Liver Homogenates for Activation and Bacteria for Detection". Proc. Natl. Acad. Sci. U.S.A. 70, pp. 2281–2285.
Ames, B.N. et al (1973) "An Improved Bacterial Test System for the Detection and Classification of Mutagens and Carcinogens". Proc. Natl. Acad. Sci. U.S.A. 70, pp. 782–786.
Ames, B.N. (1979) "Identifying Environmental Chemicals Causing Mutations and Cancer". Science 204, pp. 587–593.
Gold, L.S. et al (1991) "The Carcinogenic Potency Database: Analyses of 4000 Chronic Animal Cancer Experiments Published in the General Literature and by the U.S. National Cancer Institute/National Toxicology Program". Environ. Health Perspect. 96, pp. 11–15.
Moslen, M.T. et al (1985) "1,2–Dibromoethane Initiation of Hepatic Nodules in Sprague–Dawley Rats Selected With Solt–Farber System". Arch. Toxicol. 58, pp. 118–119.

Gold, L.S. et al (1990) "The Importance of Ranking Possible Carcinogenic Hazards Using HERP". Risk Anal. 10, pp. 625–628.
Buesser, M.T. et al (1987) "Stimulation of DNA Synthesis in Rat and Mouse Liver by Various Tumor Promoters". Carcinogenesis 8, pp. 1433–1437.
Woelfle, D. et al (1988) "Altered Growth Control of Rat Hepatocytes After Treatment With 3,4,3',4'-tetrachlorobiphenyl in vivo and in vitro". Carcinogenesis 9, pp. 919–924.
Chida, K. et al (1986) "Activation of Protein Kinase C and Specific Phosphorylation of a $M_r$ 90,000 Membrane Protein of Promotable BALB/3T3 and C3H/10T1/2 Cells by Tumor Promoters". Cancer Res. 46, pp. 1055–1062.
Novak–Hofer, I. et al (1987) "Estrogen Stimulates Growth of Mammary Tumor Cells ZR–75 Without Activation of S6 Kinase and S6 Phosphorylation. Difference From Epidermal Growth Factor and α–Transforming Growth–Factor–Induced Proliferation". Eur. J. Biochem. 164, pp. 445–451.
Yarden, Y. et al (1988) "Growth Factor Receptor Tyrosine Kinases". Annu. Rev. Biochem. 57, pp. 443–478.
Yarden, Y. et al (1988) "Molecular Analysis of Signal Transduction by Growth Factors". Biochemistry 27, pp. 3113–3119.
Ullrich, A. et al (1986) "Protein Kinases in Cellular Signal Transduction: Tyrosine Kinase Growth Factor Receptors and Protein Kinase C". Cold Spring Harb. Symp. Quant. Biol. 51 Pt 2, pp. 713–724.
Yarden, Y. et al (1987) "Human Proto–Oncogene C–Kit: A New Cell Surface Receptor Tyrosine Kinase for an Unidentified Ligand". EMBO J. 6, pp. 3341–3351.
Hunter, T. (1986) "Cancer. Cell Growth Control Mechanisms [news]". Nature 322, pp. 14–16.
Maller, J.L. et al (1989) "Maturation–Promoting Factor and the Regulation of the Cell Cycle". J. Cell Sci. Suppl. 12, pp. 53–63.
Ma, X. et al (1991) "Benzo[e]pyrene Pretreatment of Immature, Female C57BL/6J Mice Results in Increased Bioactivation of Aflatoxin $B_1$ in vitro". Toxicol. Lett. 59, pp. 51–58.
Laemmli, U.K. et al (1973) "Maturation of the Head of Bacteriophage T4. I. DNA Packaging Events". J. Mol. Biol. 80, pp. 575–599.
Towbin, H. et al (1979) "Electrophoretic Transfer of Proteins From Polyacrylamide Gels to nitrocellulose Sheets: Procedure and Some Applications". Proc. Natl. Acad. Sci. U.S.A. 76, pp. 4350–4354.
Smith, P.K. et al (1985) "Measurement of Protein Using Bicinchoninic Acid [published erratum appears in Anal Biochem May 15, 1987; 163(1):279]". Anal. Biochem. 150, pp. 76–85.

(List continued on next page.)

*Primary Examiner*—Lila Feisee
*Assistant Examiner*—Yvonne Eyler
*Attorney, Agent, or Firm*—Barnard, Brown & Michaels

[57] ABSTRACT

In vivo and in vitro assays for the detection and quantification of substances, which are carcinogenic, but not genotoxic or mutagenic, by measuring a correlative change in cyclin dependent kinases (CDK).

14 Claims, 45 Drawing Sheets

OTHER PUBLICATIONS

Elledge, S.J. et al (1991) "A New Human p34 Protein Kinase, CDK2, Identified by Complementation of a cdc28 Mutation in *Saccharomyces Cerevisiae,* is a Homolog of Xenopus Eg1". EMBO J. 10, pp. 2653–2659.

Sjoelander, S. et al (1991) "Integrated Fluid Handling System for Biomolecular Interaction Analysis". Anal. Chem. 63, pp. 2338–2345.

Dubs, M.C. et al (1992) "Mapping of Viral Epitopes With Conformationally Specific Monoclonal Antibodies Using Biosensor Technology". J. Chromatogr. 597, pp. 391–396.

Dubs, M.C. et al (1991) "Interaction Between Viruses and Monoclonal Antibodies Studied by Surface Plasmon Resonance". Immunol. Lett. 31, pp. 59–64.

Draetta, G. et al (1989) "The Mammalian cdc2 Protein Kinase: Mechanisms of Regulation During the Cell Cycle". J. Cell Sci. Suppl. 12, pp. 21–27.

Baguley, B.C. (1991) "Cell Cycling, cdc2, and Cancer". J. Natl. Cancer Inst. 83, pp. 896–898.

Pardee, A.B. (1989) "$G_1$ Events and Regulation of Cell Proliferation". Science 246, pp. 603–608.

Cohen, S.M. et al (1990) "Cell Proliferation in Carcinogenesis". Science 249, pp. 1007–1011.

Pines, J. et al (1991) "Cyclin–Dependent Kinases: A New Cell Cycle Motif?". Trends in Cell Biol. 1, pp. 117–121.

Ducommun, B. et al (1990) "A Versatile Microtiter Assay for the Universal cdc2 Cell Cycle Regulator". Analytical Biochem. 187, pp. 94–97.

Murray, A.W. et al (Mar., 1991) "What Controls the Cell Cycle". Scientific American, pp. 56–63.

Farber, E. et al (1986) "Chemical Carcinogenesis: The Liver as a Model". Pathol. Immunopathol. Res. 5, pp. 1–28.

Smith, B.M. et al (1988) "Protein Kinase C and its Substrates in Tumor Promoter–Sensitive and –Resistant Cells". J. Biol. Chem. 263, No. 13, May 5, pp. 6424–6431.

Hunter, T. et al (1985) "Protein–Tyrosine Kinases". Annu. Rev. Biochem. 54, pp. 897–930.

Hunter, T. et al (1985) "Protein Phosphorylation and Growth Control". Ciba Found. Symp. 116, pp. 188–204.

Funasaka, Y. et al (1992) "c–Kit–Kinase Induces a Cascade of Protein Tyrosine Phosphorylation in Normal Human Melanocytes in Response to Mast Cell Growth Factor and Stimulates Mitogen–Activated Protein Kinase but is Down––Regulated in Melanomas". Mol. Biol. Cell 3, pp. 197–209.

Bouton, A.H. et al (1991) Tyrosine Phosphorylation of Three Cellular Proteins Correlates With Transformation of Rat 1 Cells by pp60$^{src}$. Mol. Carcinog. 4, pp. 145–152.

Arion, D. et al (1988) "cdc2 is a Component of the M Phase–Specific Histone H1 Kinase: Evidence for Identity With MPF". Cell 55, pp. 371–378.

Arion, D. et al (1989) "M–Phase–Specific Protein Kinase from Mitotic Sea Urchin Eggs: Cyclic Activation Depends on Protein Synthesis and Phosphorylation but Does Not Require DNA or RNA Synethesis". Exp. Cell Res. 183, pp. 361–375.

Brizuela, L. et al (1989) "Activation of Human CDC2 Protein as a Histone H1 Kinase is Associated With Complex Formation With the p62 Subunit". Proc. Natl. Acad. Sci. U.S.A 86, pp. 4362–4366.

Draetta, G. et al (1989) "cdc 2 Protein Kinase is Complexed With Both Cyclin A and B: Evidence for Proteolytic Inactivation of MPF". Cell 56, pp. 829–838.

Altschuh, D. et al (1992) "Determination of Kinetic Constants for the Interaction Between a Monoclonal Antibody and Peptides Using Surface Plasmon Resonance". Biochemistry 31, pp. 6298–6304.

Draetta, G. et al (1988) "Activation of cdc2 Protein Kinase During Mitosis in Human Cells: Cell Cycle–Dependent Phosphorylation and Subunit Rearrangement". Cell 54, pp. 17–26.

Ducommun, B. et al (1991) "cdc2 Phosphorylation is Required for its Interaction With Cyclin". EMBO J. 10, pp. 3311–3319.

Draetta, G. (1990) "Cell Cycle Control in Eukaryotes: Molecular Mechanisms of cdc 2 Activation". Trends Biochem. Sci. 15, pp. 378–383.

Morla, A.O. (1989) "Reversible Tyrosine Phosphorylation of cdc2: Dephosphorylation Accompanies Activation During Entry Into Mitosis". Cell 58, pp. 193–203.

Draetta, G. et al (1988) "Human cdc2 Protein Kinase is a Major Cell–Cycle Regulated Tyrosine Kinase Substrate". Nature 336, pp. 738–744.

Cohen, S.M., et al, (1992), "Cancer Enhancement By Cell Proliferation", Relevance of Animal Studies to the Evaluation of Human Cancer Risk, pp. 213–229.

Yasui, et al., *Int. J. Cancer,* vol. 53, pp. 36–41 (1993).

Hunter, *Cell,* vol. 50, pp. 823–829 (1987).

Farber, *Dig. Dis. Sci.,* vol. 36, pp. 973–978 (1991).

Farber, *Tumor Biol.,* vol. 9, pp. 165–169.

Khatib, et al., *Cancer Research* 53:22 pp. 5535–5541 (1993).

Mishra, et al., *Cancer Research* 53:3 pp. 557–563 (1993).

Marcote, et al., Proc. Annu. Meet. Am. Assoc. Cancer Res., 33:#A575 (1992).

Hellmich, et al., Proc. Annu. Meet. Am. Assoc. Cancer Res., 34:#A244 (1993).

1 2 3 4

<34kDa

CO  CO  DEN  DEN

FIG. 17

ASSAYS FOR NONGENOTOXIC, CHEMICAL CARCINOGENS

This is a continuation application of patent application Ser. No. 08/075,744, filed Jun. 11, 1993 and now abandoned, which is in turn a continuation-in-part application of patent application Ser. No. 08/007,636, filed Jan. 21, 1993, now abandoned.

FIELD OF THE INVENTION

This invention relates to in vivo and in vitro assays for the detection and quantification of substances, which are carcinogenic, but exhibit negative results in genotoxicity or mutagenicity tests.

BACKGROUND OF THE INVENTION

Introduction

Cell proliferation is the most fundamental phenotypic property of cancer. The stimulus for cellular proliferation is central not only at the late steps in carcinogenesis, the cancer, but also at the earliest known step, initiation (1,2) and FIG. 1. In fact, cell proliferation exerts an influence in the initiation of carcinogenesis in that cells in the S phase are more sensitive toward many initiators than at other times in the cell cycle (3). A myriad of short-term tests exist for the assessment of the carcinogenic potential of chemicals. These tests detect only carcinogens that interact with nucleic acids, or induce DNA repair synthesis or mutations in bacterial or mammalian cells (4–8).

As testing of the genotoxicity and carcinogenicity of chemicals has become routine, a growing number of compounds have been found to induce tumors in chronic bioassays while exhibiting negative results in genotoxicity tests (9). Significant examples of these classes of compounds include the dioxins, chlorinated biphenyls and peroxisome proliferators. These chemicals are often active as tumor promoters in two-stage experiments and exhibit biological activities as hormones (ethinylestradiol), peroxisome proliferators (pirnixic acid) or enzyme inducers (phenobarbital) (10).

At the present time only the initiation-promotion assay is employed routinely. In this assay the test compounds are examined for their ability to promote hepatic tumors or foci formation after initiation with a known genotoxic agent (11,12). As currently formatted, this assay utilizes animals, requires several months to perform, and produces histological endpoints that are difficult to quantify and do not lend to rigorous dose-response calculations for the purposes of risk assessment (13).

Stimulation of DNA synthesis has been proposed as an assay for short-term assessment of nongenotoxic carcinogens and tumor promoters in vivo (14,15). This methodology has potential for application to routine testing. So far, only one result has been detected that is inconsistent with carcinogenicity bioassay data. The different carcinogenicity of di(2-ethylhexyl)adipate (negative in rats) and di(2-ethylhexyl)phthalate (positive) was not detectable by DNA stimulation index using $^3$H-thymidine. Both plasticizers were positive in this short-term system with doubling doses of 0.7 mmol/kg for di(2-ethylhexyl)adipate and 0.5 mmol/kg for di(2-ethylhexyl)phthalate. Other disadvantages of this system include the use of radioactivity and the high coefficient of variation in the endpoint.

Several in vitro models have been utilized for the assessment of nongenotoxic carcinogens. Chida et al. (16) modeled the activation of protein kinase C and specific phosphorylation of a 90,000 kDa membrane protein of promotable BALB/3T3 and C3H/10T1/2 cells by tumor promoters. Smith and Colburn also utilized protein kinase C and its substrates in tumor promoter-sensitive and tumor-resistant cells as a biochemical marker for the response of cells to tumor promoters (17). However, these systems were flawed by both false positive and false negative values. The false positive values may be due to the fact that the activation of protein kinases C represents a biochemical signal far upstream from the final proliferative signal, while the false negatives may result from the fact that protein kinase C represents only a single receptor-mediated response. At least four other receptor responses, which are independent of protein kinase C, are known for tumor promotion and activity of nongenotoxic carcinogens (e.g. dioxin receptor, peroxisome proliferator receptor, phenobarbital receptor and estrogen receptor) (14,18).

Protein tyrosine phosphorylation

Protein-tyrosine kinases (PTK) constitute a class of enzymes that catalyze the transfer of the $\mu$-phosphate of either ATP or GTP to specific tyrosine residues in certain protein substrates. Evidence suggests that these enzymes are important mediators of normal cellular signal transduction (19–21), with PTK being the intracellular effectors for many growth hormone receptors (22–24). PTK are also frequently the products of proto-oncogenes (25) and their aberrant expression has been associated with a variety of human cancers (26).

The cascade of protein tyrosine phosphorylation following the activation of protein tyrosine kinases appears to regulate the proliferative response (27,28). Specific, protein tyrosylphosphorylations are common to a wide variety of nongenotoxic carcinogens independent of associated receptors or known mechanism of action. The present invention demonstrates the xenobiotic alterations in protein tyrosine phosphorylation at a fundamental point in the control of cellular proliferation and on an assay protocol that characterizes the ability of a xenobiotic test chemical to initiate cellular proliferation.

Cyclin-dependent Kinases (CDK)

Recent experimental evidence suggests that the cell cycle of all eukaryotic cells is controlled at several checkpoints by different members of a novel class of protein kinase, the cyclin-dependent kinases (29, 31, 36, 46). The most well known of these kinases is the 34 kD product of the cdc2 gene in the fission yeast p34$^{cdc2}$; however, several putative cyclin-dependent kinases (CDK) have now been cloned or identified. Some of these clones resemble p34$^{cdc2}$.

At least nine CDKs have been described in the literature; these all have a common PSTAIR (SEQ. ID. NO:1) epitope. Therefore anti-PSTAIR would be expected to cross react with the entire complement of CDKs showing up in the 32 to 34 kD region. (Apparently some cyclins also cross react with the anti-PSTAIR antibody and this explains the banding at approximately 60 kD observed in some of the immunoblots with anti-PSTAIR.)

The antibody to the C-terminus region is more specific for p34$^{cdc2}$ kinase, since the C-terminus region is more variable than the highly conserved PSTAIR (SEQ.ID.NO:1) region. However, it is obviously not species-specific since it was generated against human cdc2 and it cross reacts with mouse, rat and dog p34$^{cdc}$2 kinase.

SUMMARY OF THE INVENTION

A method and assay to determine whether a test compound or sample is a nongenotoxic carcinogen, wherein the compound or sample to be tested is added to a cyclin dependent kinase (CDK) assay system. The assay system of this invention can be a living organism, a cell culture or a cell lysate, as long as the assay system contains a cyclin dependent kinase (CDK). An increase in the tyrosylphosphorylation level of CDK indicates that the test compound is a nongenotoxic carcinogen, or that the test sample contains a nongenotoxic carcinogen.

This assay also detects nonmutagenic carcinogens and substances having a cell proliferation effect. The nongenotoxic carcinogens that can be identified through the assay include tumor promoters, chlorinated biphenyls, hormones, dioxins and peroxisome proliferators, among others. The assay system can be assembled in the form of a test kit for diagnostic and environmental testing.

The above assay could also be used to quantify the potency of a particular growth factor (peptide hormone). A peptide growth factor would be added to the assay system instead of a xenobiotic (foreign chemical) and otherwise the assay would proceed without modification.

The method and assay of the invention can also be used to determine the potential of a chemical as an antineoplastic agent by reversing the steps outlined above. Starting with a transformed cell or transformed cell lysate, a potential antineoplastic agent would be tested for the capacity of the chemical to put the cells into the $G_0$ state. This capacity would be determined by quantifying the decrease in tyrosylphosphorylation of the CDK. The only other modification necessary to convert the assay for nongenotoxic carcinogens to one for antineoplastic agents is to grow the neoplastic cells in vitro in a full serum complement (20% serum containing medium)

BRIEF DESCRIPTION OF THE DRAWINGS

FIG. 17. Anti-phosphotyrosine immunoblots of rat hepatic S-9 protein separated using 11% SDS-PAGE gels for diethylnitrosamine-treated (lanes 3,4) and control (lanes 1,2) rats.

DETAILED DESCRIPTION OF CERTAIN PREFERRED EMBODIMENTS

In Vivo Experiments

EXAMPLE 1

Figure 1:
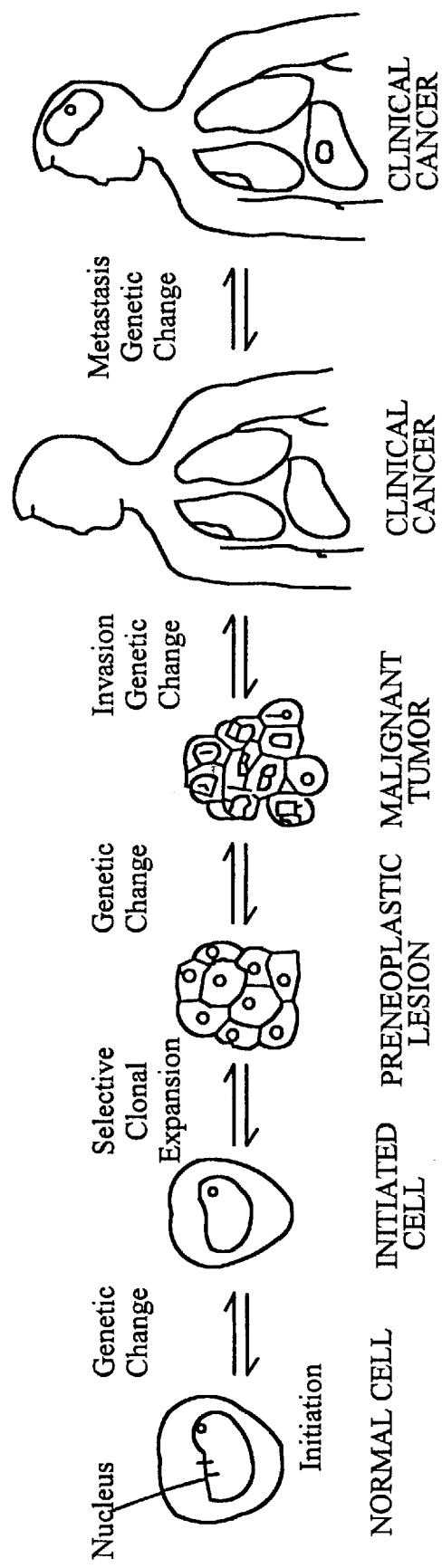
FIG. 1 Schematic of the multistage nature of carcinogenesis. Nongenotoxic carcinogens and tumor promoters affect, respectively, defects in terminal differentiation and selective clonal expansion of initiated cells.
Figure 2:
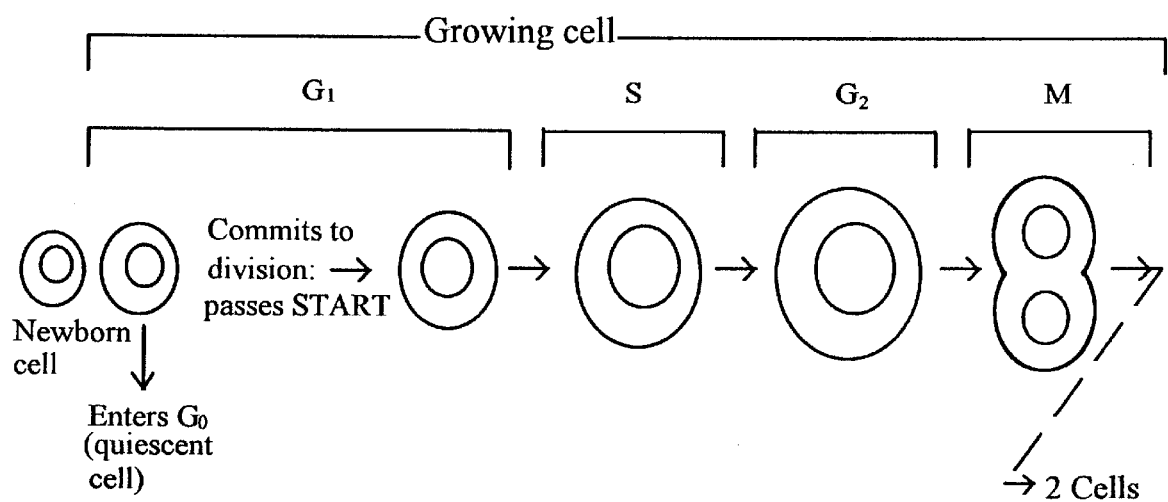
FIG. 2. A representation of the relationship between cell injury and neoplasia. The role of cell proliferation is characterized by the increased cell replication step.
Figure 3:
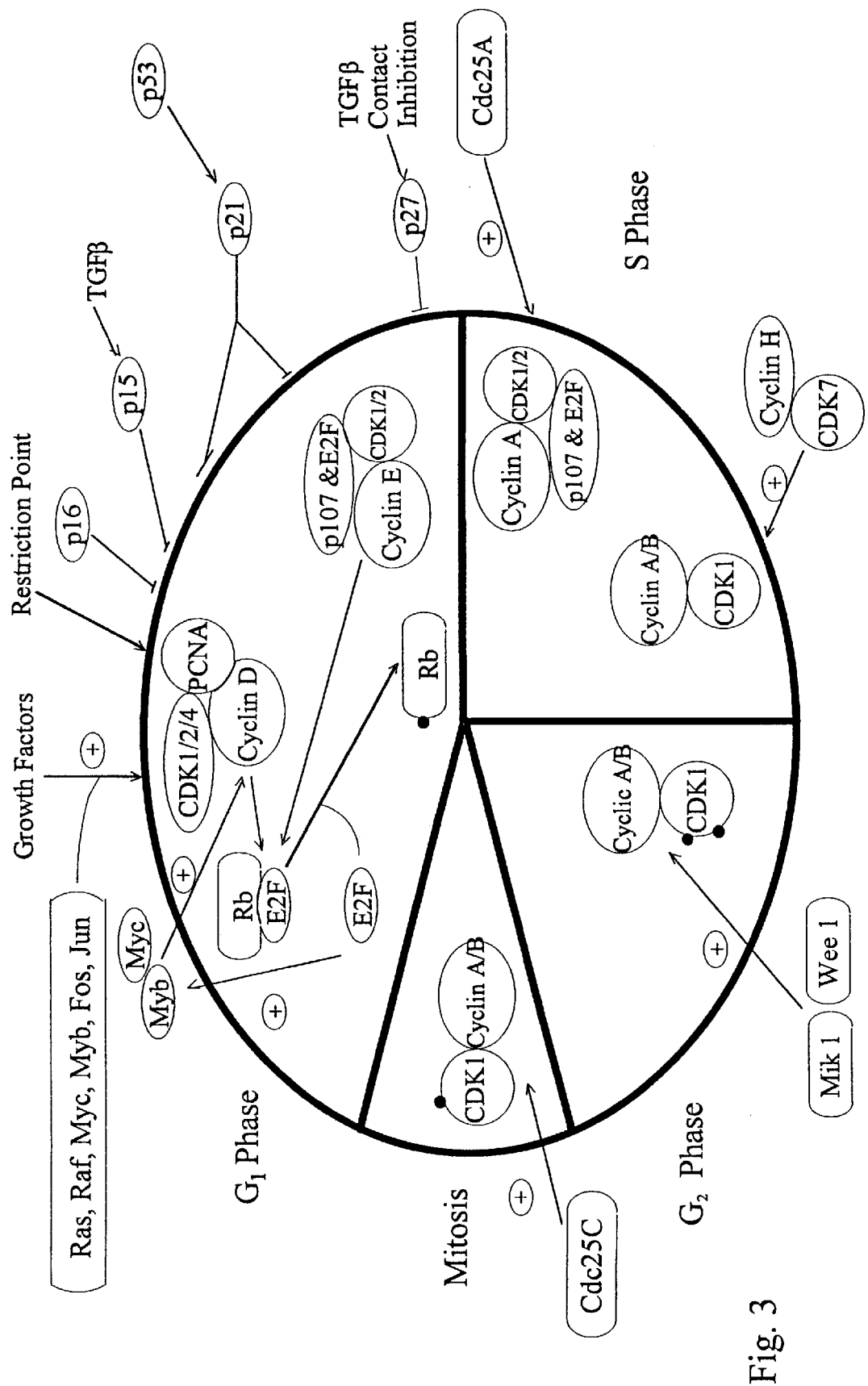
FIG. 3. The cell cycle. A cell can either be quiescent or continue to grow. The decision point is early in the G1 phase when a cell either passes START—and then is committed to growing, finishing the rest of the cycle and dividing (G1, S, G2 and M)—or the cell enter the $G_0$ state in which it continues to metabolize but does not grow.

Enhanced tyrosylphosphorylation of $p34^{cdc2}$ kinase in an mice 24 hours following administration of the nongenotoxic carcinogen 2,3,7,8-tetrachlordibenzo-p-dioxin Summary $p34^{cdc2}$ is the serine/threonine kinase subunit of M-phase promoting factor (MPF) (29–31). The regulation of $p34^{cdc2}$ tyrosine phosphorylation status is considered the control mechanism for entry into $G_1$ from $G_0$, the START signal, and also from $G_2$ to M, the initiation of mitosis. It is demonstrated that a single dose of 2,3,7,8-tetrachlorodibenzo-p-dioxin administered at 0.25, 0.5, 1, or 2 μg/kg to young, female mice increases the extent of tyrosylphosphorylation of hepatic $p34^{cdc2}$ kinase compared to corn oil treated controls. These results indicate that the proliferative stimulus of the nongenotoxic carcinogen 2,3,7,8-tetrachlorodibenzo-p-dioxin may be quantified as an increase in hepatic $p34^{cdc2}$ kinase tyrosylphosphorylation and therefore that stimulation of tyrosylphosphorylation of hepatic $p34^{cdc2}$ kinase can serve to indicate the capacity of a dioxin-like chemical to function in vivo as a nongenotoxic carcinogen.

Materials and Methods

Chemicals: 2,3,7,8-tetrachlorodibenzao-p-dioxin (TCDD) is purchased from AccuStandard, Inc. (New Haven, Conn.).

Anti-phosphotyrosine monoclonal, anti-PSTAIR (CDK), and anti-$p34^{cdc2}$ kinase C-terminus polyclonal antibodies are obtained from UBI (Lake Placid, N.Y.). The acronym PSTAIR (SEQ.ID.NO:1) is the abbreviation for the amino acid sequence used as the antigen for developing the anti-PSTAIR (SEQ.ID.NO:1) antibody. The two antibodies (PSTAIR and anti-C-terminus) recognize two different epitopes. At least nine CDKs have been described in the literature; these all have a common PSTAIR (SEQ.ID.NO:1) epitope. Therefore anti-PSTAIR would be expected to cross react with the entire complement of CDKs showing up in the 32 to 34 kD region. (Apparently some cyclins also cross react with the anti-PSTAIR antibody and this explains the banding at approximately 60 kD observed in some of the immunoblots with anti-PSTAIR.)

The antibody to the C-terminus region is more specific for p34$^{cdc2}$ kinase, since the C-terminus region is more variable than the highly conserved PSTAIR (SEQ.ID.NO:1) region. However, it is obviously not species-specific since it was generated against human cdc2 and it cross reacts with mouse, rat and dog p34$^{cdc2}$ kinase.

One or the other antibody is used depending upon the specificity desired in the experiments.

Bicinchoninic acid is obtained from Pierce (Rockford, Ill.). Molecular weight standards are supplied through Bio-Rad (Melville, N.Y.). All other chemicals are purchased from Sigma (St. Louis, Mo.) and are of the highest purity available.

Animals and dosing

Four to six-wk old, female C57BL/6J mice are obtained from Harton Sprague Dawley (Indianapolis, Ind.). The mice are fed Prolab RMH 1000 (Agway, Cortland, N.Y.) and receive tap water ad libitum. All mice are housed three per cage and maintained on a photoperiod of 12 h. Mice are killed 24 h following an intraperitoneal injection of TCDD in corn oil at 0, 0.25, 0.5, 1, or 2 μg/kg. Three mice are treated at each dose and the volume of the injections ranges from 0.1 to 0.2 mL per mouse. All preparation procedures are performed on pooled hepatic samples of the three mice per dose.

Preparation and −80° C. storage of hepatic S-9 fractions is performed exactly as previously described in the scientific literature (32). This procedure involves killing the mouse by cervical dislocation, removing the liver and homogenizing the liver in three volumes of 0.15M KCl. This hepatic homogenate is centrifuged at 9,000×g for 20 min at 4° C. The resulting supernatant fraction, termed the S-9, is decanted into 1.5 mL plastic, conical tubes, frozen in a dry ice/ethanol bath and stored at −80° C. until immunoprecipitation of phosphotyrosyl proteins can be performed.

Immunoprecipitation of tyrosine phosphorylated hepatic S-9 proteins with anti-phosphotyrosine monoclonal antibody The hepatic S-9 is solubilized in immunoprecipitation buffer containing 20 mM Tris HCl (pH 8.0), 137 mM NaCl, 10% glycerol, 1% NP-40, 1 mM phenylmethylsulphonyl fluoride (PMSF), 0.15 U/mL aprotinin, and 1 mM sodium vanidate, centrifuged at 13,000×g for 15 min at 4° C. The solubilized hepatic S-9 proteins are then incubated with anti-phosphotyrosine monoclonal antibody (5 μg/mL) at 4° C. for 4 h or overnight. After the incubation period, add 25 μL of protein A-Sepharose for each 5 μg of antibody. One h later the immune complexes are collected by centrifugation at 13,000×g, washed twice with immunoprecipitation buffer, solubilized in SDS gel sample buffer and heated at 100° C. for 5 min in preparation of SDS PAGE and immunoblotting.

Gel electrophoresis and immunoblotting

SDS PAGE is carried out as described in the scientific literature (33) using 11% polyacrylamide gels with the modification that hepatic S-9 (100 μg protein/well) are subjected to heat treatment (100° C.) for 3 min. The immunoblotting assay is performed as described by Towbin et al. (34), however a Milliblot SDE electroblot apparatus (Millipore, Bedford, Mass.), is used to transfer proteins from polyacrylamide gels to an Immobilon® membrane filter (Millipore, Bedford, Mass.). Complete transfers are accomplished in 25–30 min at 500 mA and are assessed by tracking pre-stained molecular weight standards on the membrane filter.

Membrane filters are blocked by incubating in TBS (Tris buffered saline) containing 5% commercial nonfat dry milk (any commercial brand is suitable) for 30 min at room temperature The membranes are then washed in TBST (TBS with 0.05% Tween 20) and incubated for 2 h with anti-human CDK (PSTAIR (SEQ.ID.NO:1)) antibody (2–5 μg/mL) in TBST or anti-mouse cdc2 kinase (C-terminus) polyclonal antibody in TBST. The antibody reaction is visualized by incubating the membranes for 2 h at room temperature with alkaline phosphatase-conjugated anti-mouse IgG diluted 1:1000 in TBST and developed for 15 min. Molecular weights are determined by adding molecular weight standards (Bio Rad, Melville, N.Y.) to reference lanes and staining the membrane filters with amido black 10 B. The resulting immunoblots are scanned into TIFF-formatted files (MacIntosh®; Apple Computers, Cupertino, Calif.) with a Microtech 600GS scanner (Torrance, Calif.) and quantified using Scan Analysis (BIOSOFT, Cambridge, UK). Summary scans are then printed and peak heights are measured directly from the figure. One density unit (U) is defined as one mm of the resulting peak height.

Protein determination

Bicinchoninic acid is used for the spectrophotometric determination of protein concentration (35). Mix 100 μL of sample (standard or unknown) with 2 mL of working reagent in a test tube. Color development occurs by incubation at 37° C. for 30 min. Absorbance is read at 562 nm. Working reagent is made by adding 100 volumes of Reagent A with 2 volumes Reagent B. Reagent A: is made by combining 1.0 g bicinchoninic acid (Pierce Chemical, Rockford, Ill.); 2.0 g $Na_2CO_3*H_2O$; 0.16 g NaOH; and 0.95 g $NaHCO_3$ with water to 100 mL and adjust the pH to 11.25 with 50% NaOH. Reagent B consists of 4.9 g $CuSO_4*5H_2O$ to 100 mL in double distilled $H_2O$.

Results

Figure 4:
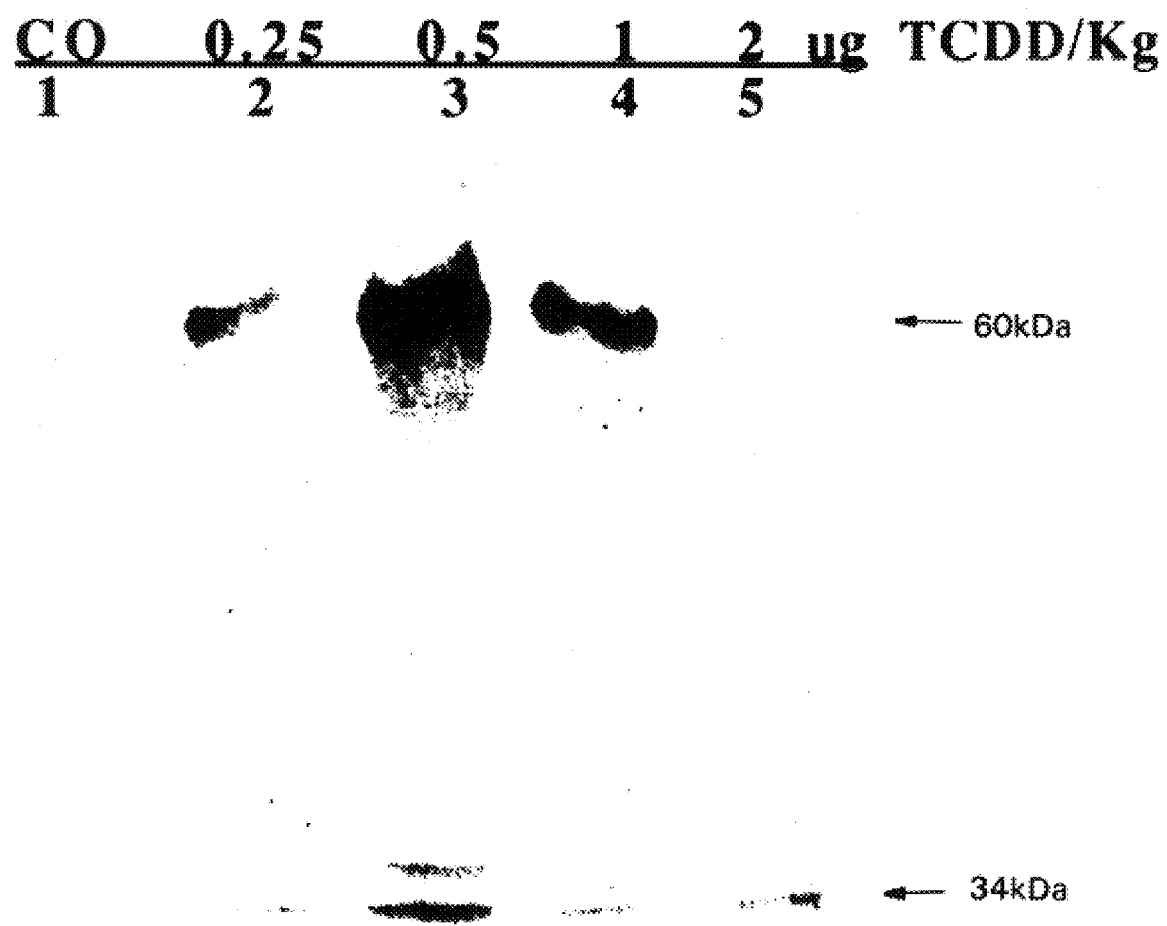
FIG. 4 Immunoblot using anti-PSTAIR antibody. An anti-phosphotyrosine immunoprecipitate of the murine hepatic S-9 protein is separated using an 11% SDS-PAGE gel. The separated proteins are transferred to a blotting membrane and probed with the anti-PSTAIR antibody.
Figure 5A:
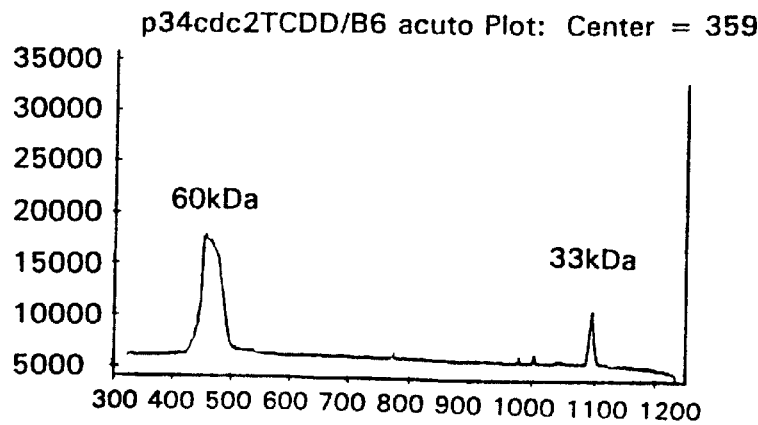
FIG. 5. Scanning densitometry of anti-PSTAIR immunoblots for hepatic S-9 fraction of 2,3,7,8-tetrachlorodibenzo-p-dioxin treated female, C57BL/6J mice.
Figure 5B:
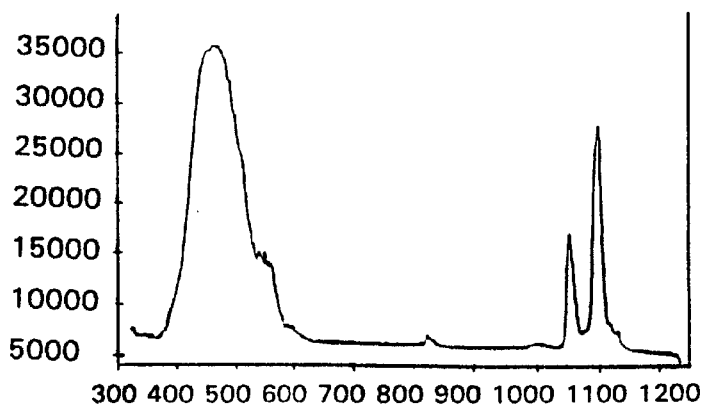
Figure 5C:
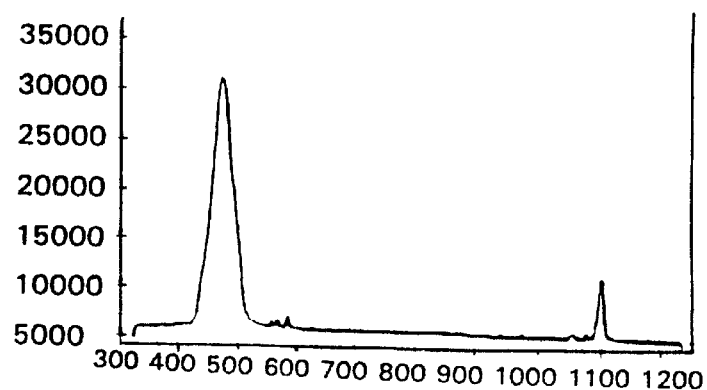
Figure 5D:
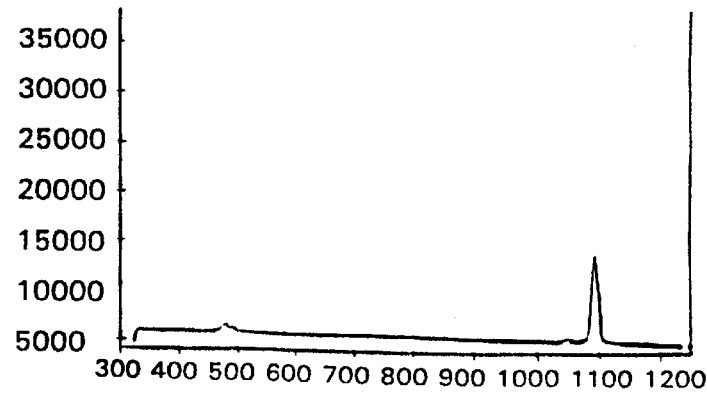
Figure 6:
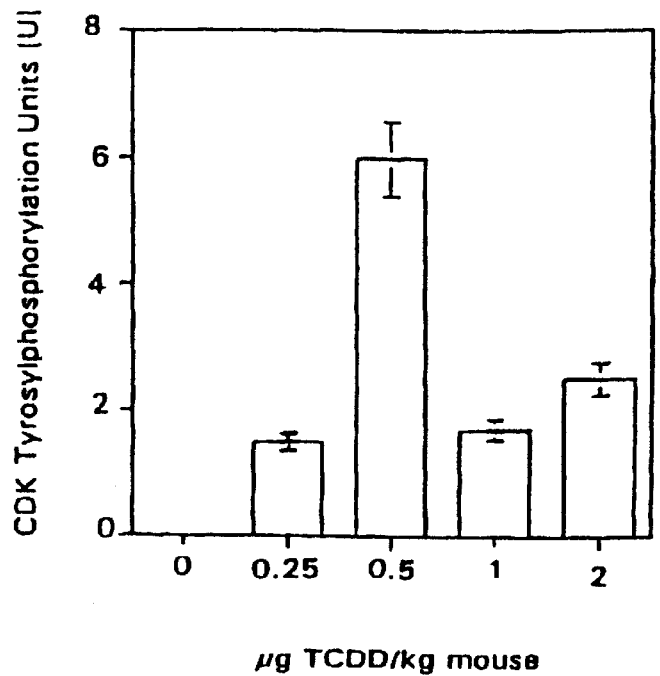
FIG. 6. Bar graph depicting the quantification of the results of the scanning densitometry. The cyclin dependent kinase (CDK) quantified from the anti-PSTAIR immunoblot was at 32 kDa. The administration of a single dose of 2,3,7,8-tetrachlorodibenzo-p-dioxin results in enhanced tyrosylphosphorylation of the CDK compared to control animals, which exhibit no tyrosylphosphorylation of CDK. Each group on the graph represents the single result of scanning an anti-PSTAIR immunoblot produced from the pooled hepatic S-9 of three animals. Error bars represent the 10 percent coefficient of variation in the quantification of density.

The anti-phosphotyrosine immunoprecipitate of the murine hepatic S-9 is run on an 11% polyacrylamide gel as described above and immunoblotting is performed with the anti-PSTAIR monoclonal antibody. The resulting anti-PSTAIR immunoblot is depicted in FIG. 4. Density scans of the immunoblot are presented in FIG. 5 and the quantification of these bands is presented in FIG. 6. The bands in FIG. 4 at 34 and 32 kDa immunoreactive with anti-PSTAIR have been identified as cyclin dependent kinases and at this time it is not known if they represent isoforms of a single pp34$^{cdc2}$ kinase or whether they are two separate cyclin dependent kinases (36). The large anti-PSTAIR immunoreactive band at approximately 60 kDa has been identified as a cyclin protein (37, 38).

The results demonstrate that the tyrosylphosphorylated CDK (pp34$^{cdc2}$) does not exist in measurable quantities in the hepatic S-9 of corn oil treated control mice. However, dosing of mice with TCDD enhanced the tyrosylphosphorylation of a p34 and p32 to a maximum at 0.5 μg TCDD/kg. At higher doses of TCDD the tyrosylphosphorylation of the kinase(s) becomes attenuated, perhaps due to overt toxicity of TCDD to the mice at these higher doses.

EXAMPLE 2

Enhanced tyrosylphosphorylation of p34$^{cdc2}$ kinase in an hepatic cytosol preparation (S-9) from young male rats 24 hours following administration of the nongenotoxic carcinogen pirnixic acid Summary p34$^{cdc2}$ is the serine/threonine kinase subunit of M-phase promoting factor (MPF) (29–31). The regulation of p34$^{cdc2}$ tyrosine phosphorylation status is considered the control mechanism for entry into $G_1$ from $G_0$, the START signal, and also from $G_2$ to M, the initiation of mitosis. It is demonstrated that twice daily doses of 50 mg pirnixic acid/kg of body weight for 5 days to young male rats increases the extent of tyrosylphosphorylation of hepatic p34$^{cdc2}$ kinase compared to corn oil treated controls. These results indicate that the proliferative stimulus of the non-genotoxic carcinogen pirnixic acid may be quantified as an increase in hepatic p34$^{cdc2}$ kinase tyrosylphosphorylation and therefore that stimulation of tyrosylphosphorylation of hepatic p34$^{cdc2}$ kinase can serve to indicate the capacity of chemicals that are termed peroxisome proliferators to function in vivo as a noyngenotoxic carcinogen.

Materials and Methods

Chemicals

Pirnixic acid (CAS 50892-23-4 [4-chloro-6-(2,3-xylidino)-2-pyrimidiylthio] acetic acid) is purchased from ChemSyn Science Labs (Lenexa, Ky.). Anti-phosphotyrosine monoclonal, anti-PSTAIR (CDK), and anti-p34$^{cdc2}$ kinase C-terminus polyclonal antibodies are obtained from UBI (Lake Placid, N.Y.). Bicinchoninic acid is obtained from Pierce (Rockford, Ill.). Molecular weight standards are supplied through BioRad (Melville, N.Y.). Sensor Chips CM5, Surfactant P20, and amine coupling kit (EDC, NHS, and ethanolamine hydrochloride) were purchased from Pharmacia Biosensor AB. All other chemicals are purchased from Sigma (St. Louis, Mo.) and are of the highest purity available.

Animals and dosing

Eight-wk old male Sprague-Dawley rats are purchased from Charles River Laboratory (Charles River, Mass.) and housed four to a cage in polycarbonate cages (24×34×20 cm). Bedding consists of hardwood chips. Rats are allowed free access to tap water and fed Agway RMH 3000 (Cortland, N.Y.) ad libitum. Photoperiod is maintained at 12 h of light and 12 h of darkness.

After a wk of acclimation to new surroundings, treatments are begun. The treatment consists of twice daily doses of the test compound administered by oral gavage. The pirnixic acid is dissolved in corn oil. Sham-treated animals are given an equal volume of plain corn oil. Doses are adjusted daily on the basis of weight. The volume of corn oil is generally on the order of 2 mL/ rat throughout the treatment period. The second dose is given between the h of 13:00–16:00, approximately 6 h after the first dose given between the h of 7:00–10:00. The pirnixic acid is administered for 5 days at a dose of 50 mg/kg twice a day.

On the day of sacrifice the rats are anesthetized with ethyl ether and decapitated. Livers are removed, weighed and homogenized using a Potter-Elvehjem® tissue grinder with 3 mL of ice-cold 0.15M KCl per g of wet weight of liver. This material is pooled for each rat and spun in a high speed centrifuge (Beckman J2-MI, Beckman Instruments, Fullerton, Calif.) for 10 min at 9000×g at 4° C. The supernatant liquid is decanted, distributed as aliquot and frozen at −90° C.

Gel electrophoresis and immunoblotting with anti-phosphotyrosine

These procedures are carried out essentially as described in Example 1 except that anti-phosphotyrosine antibody is used in place of anti-PSTAIR antibody.

Protein determination

This procedure is performed as described in Example 1.

Real-time quantification of total tyrosylphosphorylated p34$^{cdc2}$ kinase

Surface plasmon resonance (SPR) is used for the real time quantification of p34$^{cdc2}$ kinase that exists in the tyrosylphosphorylated form. SPR is sensitive to changes in the optical properties of a medium close to a metal surface (39). SPR is suitable for macromolecular interaction studies at solid/liquid interfaces with the use of a carboxymethylated dextran hydrogel placed upon a thin layer of gold (39,40).

The detection system of a SPR monitor consists of a light source emanating both monochromatic and plane-polarized light, a glass prism, a thin metal film in contact with the base of the prism, and a photodetector. An evanescent field forms from the prism into the metal film when obliquely incident light on the base of the prism will exhibit total internal reflection for angles greater than the critical angle. This evanescent field can couple to an electromagnetic surface wave, a surface plasmon, at the metal/liquid interface. Coupling is achieved at a specific angle of incidence, the SPR angle (39).

The SPR angle is highly sensitive to changes in the reactive index of a thin layer adjacent to the metal surface which is sensed by the evanescent wave. Therefore, it is a volume close to the surface that is probed. For example, when a protein layer is adsorbed on the metal surface, keeping all other parameters constant, an increase in the surface concentration occurs and the SPR angle shifts to larger values (39). The magnitude of the shift, defined as the SPR response, depends on the mean refractive index change due to the adsorption in the probed volume (a function of mass).

Utilizing SPR, biospecific interaction analysis is performed in real time in conjunction with a flow injection system and is as sensitive as other methods such as radiolabeling, fluorometry, and chemiluminescence. In short, biospecific interaction analysis is a sensitive, non-labile way of examining interactions between macromolecules in real time (40–42).

SPR measurements are performed on a BIAcore unit manufactured by Pharmacia Biosensor AB (Uppsala, Sweden). Sensor Chips CM5, Surfactant P20, and amine coupling kit (EDC, NHS, and ethanolamine hydrochloride) were purchased from Pharmacia Biosensor AB.

Immobilization of PSTAIR (SEQ.ID.NO:1) and C-terminus antibodies via amine coupling was performed according to the general procedure recommended by the manufacturer. Briefly, the instrument was equilibrated with HBS buffer (10 mM HEPES, 150 mM NaCl, 0.05% surfactant P20, pH 7.4, and filtered with a 0.22 micron filter), then the following series of injections were made using the autosampler incorporated into the BIAcore units:

(1) equal volumes of EDC (0.1M in water) and NHS (0.1M in water) were mixed and 35 μL injected to activate the carboxymethylated surface;

(2) ligand (35 μL, 50 μg/mL in 10 mM sodium acetate pH 4.5) was then injected;

(3) the remaining NHS-esters on the surface were then deactivated with ethanolamine (35 μL, 1M in water, pH 8.5);

(4) noncovalently bound material was then washed from the surface with hydrochloric acid (15 μL. 20 mM). Immobilizations were executed with a continuous flow of HBS at a flow rate of 5 μL/min.

Figure 7:
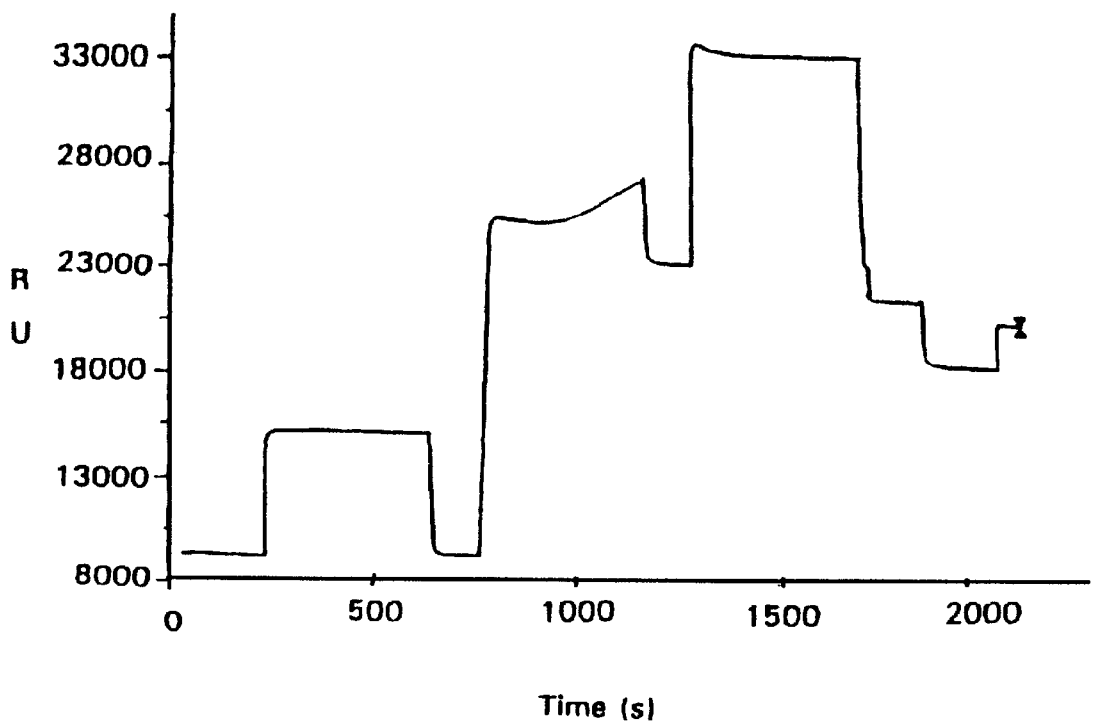
FIG. 7. A typical BIAcore sensorgram produced on immobilization of anti-cdc2 kinase C-terminus.

A typical sensorgram produced on immobilization of anti-cdc2 C-terminus is depicted in FIG. 7. Time required for immobilization is approximately 30 min.

BIAcore assay for tyrosylphosphorylation of cycline dependent kinase (CDK)-Each binding/regeneration cycle is performed with a constant flow of HBS of 3 μL/min. Hepatic S-9 fractions of rats dosed with pirnixic acid or vehicle alone are diluted to a concentration of 1.5 mg protein/mL into exhausted FB-2 tissue culture supernatant liquid and incubated overnight at 4° C. with anti-phosphotyrosine antibody. This equilibrated mixture (40 μL) is then injected over the immobilized PSTAIR (SEQ.ID.NO:1) and C-terminus antibodies and binding is recorded in RU. Binding is directly proportional to the amount of tyrosylphosphorylated protein interacting with the anti-PSTAIR or anti-C Terminus antibodies.

Interpretation of Results

Immunoblots—For scans of immunoblots a change in phosphotyrosylprotein content of p34$^{cdc2}$ kinase greater than 40 percent was considered biologically meaningful.

BIAcore assay—Research on the cell cycle has shown that the concentration of cdc2 kinase remains constant and that tyrosine phosphorylation can be utilized as a marker of cells that are preparing to enter the M phase of the cell cycle (43–48). Therefore, increased binding indicate increased tyrosylphosphorylation of cdc2 kinase, thus more cells are in the process of preparing to enter mitosis. Treatment effects from BIAcore analyses are considered significant when the instrument response of the treatment group is outside the upper bounds of the population 95 percent confidence interval ($t_{(5)(0.95)}$=2.015 times the standard deviation of the RU response of the control animals).

Results

Figure 8:
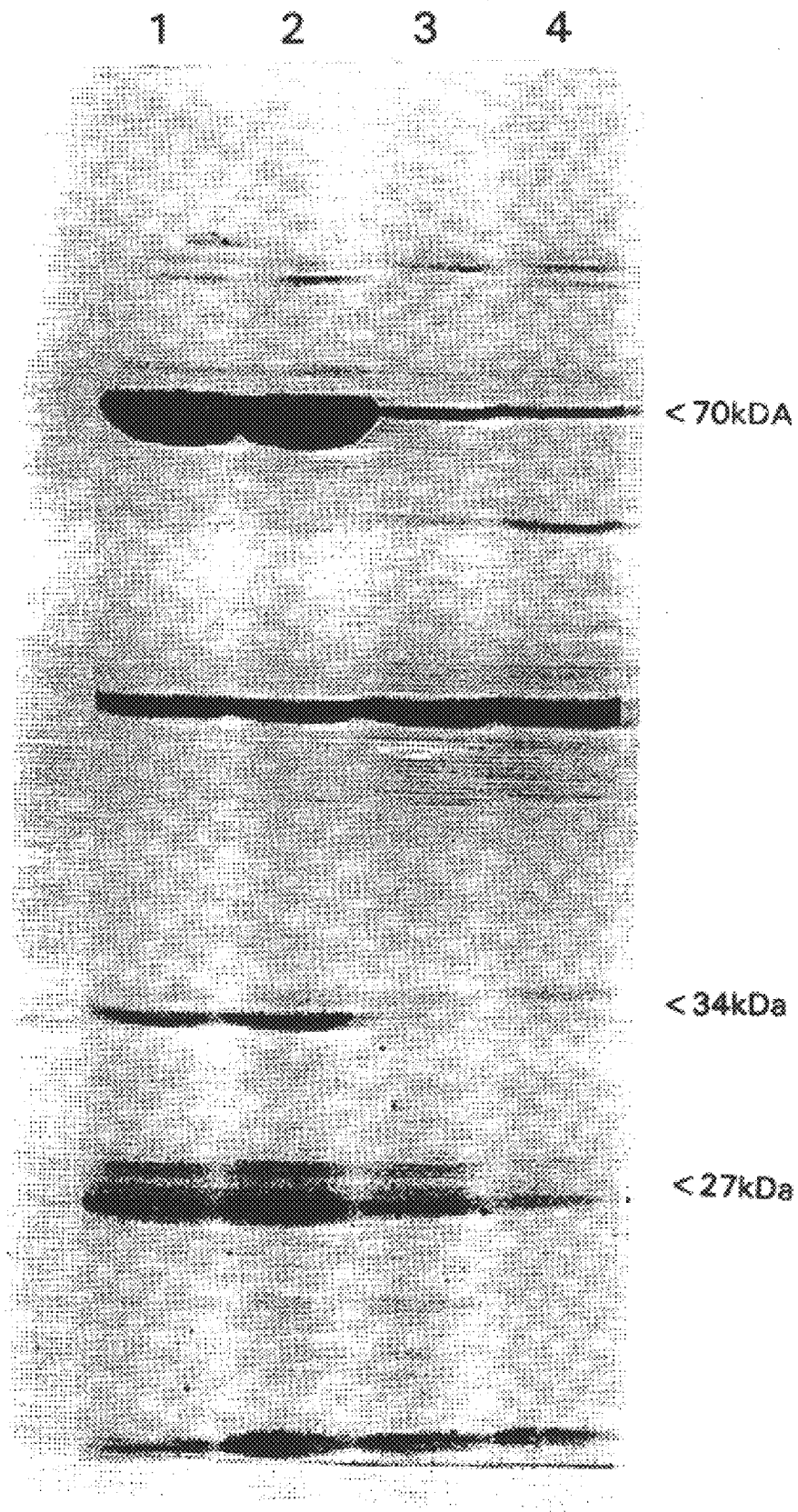
FIG. 8. Anti-phosphotyrosine immunoblots of rat hepatic S-9 protein separated using 11% SDS-PAGE gels for pirnixic acid-treated (lanes 1,2) and control (3,4) rats. Each lane represents a single rat.
Figure 9A:
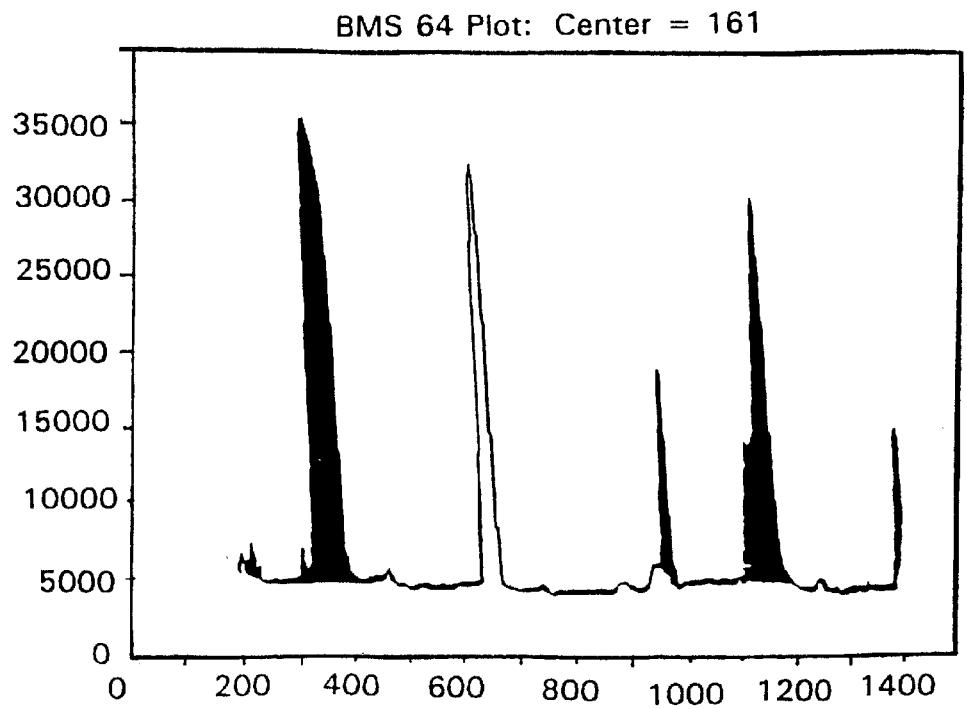
FIG. 9. Scanning densitometry of anti-phosphotyrosine immunoblots for pirnixic acid-treated rats [A and B] and paired vehicle controls [C and D, respectively]. Bolding of peaks indicates difference of greater than 40 percent between treatment and control.
Figure 9B:
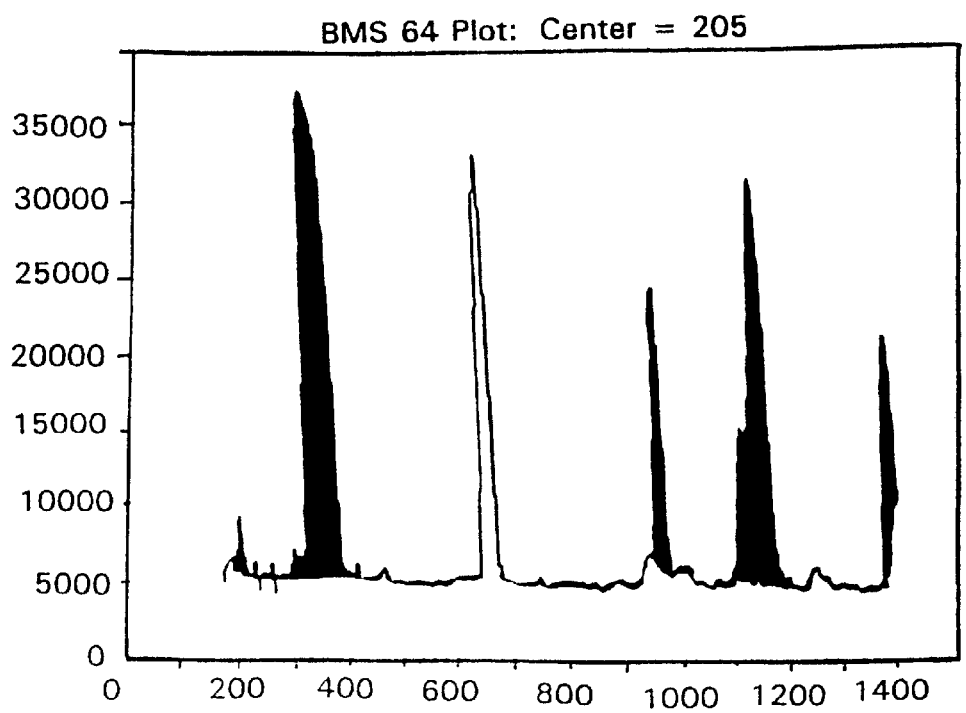
Figure 9C:
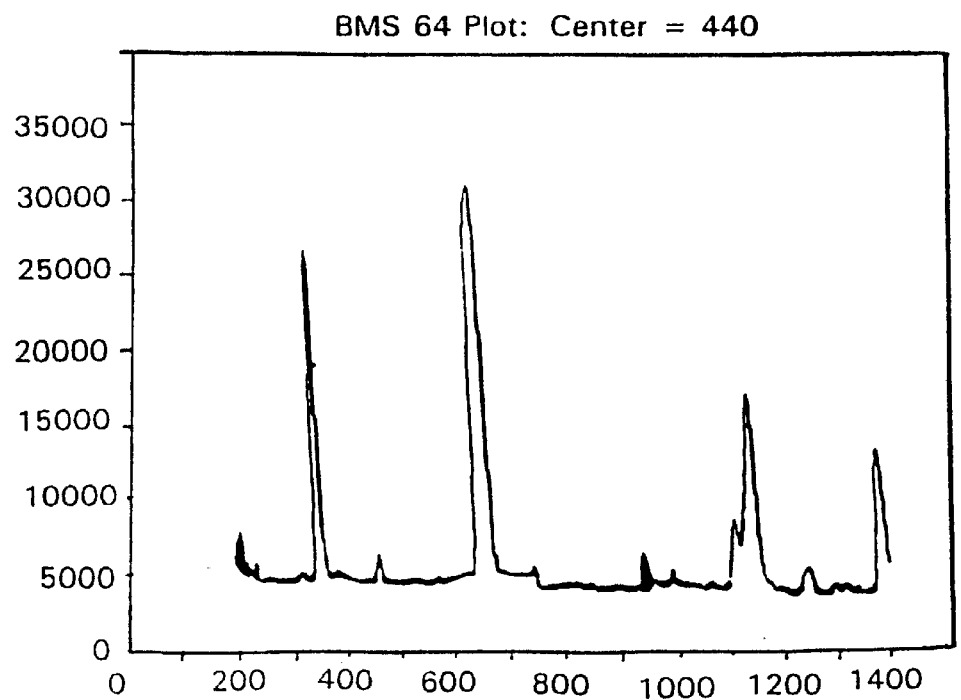
Figure 9D:
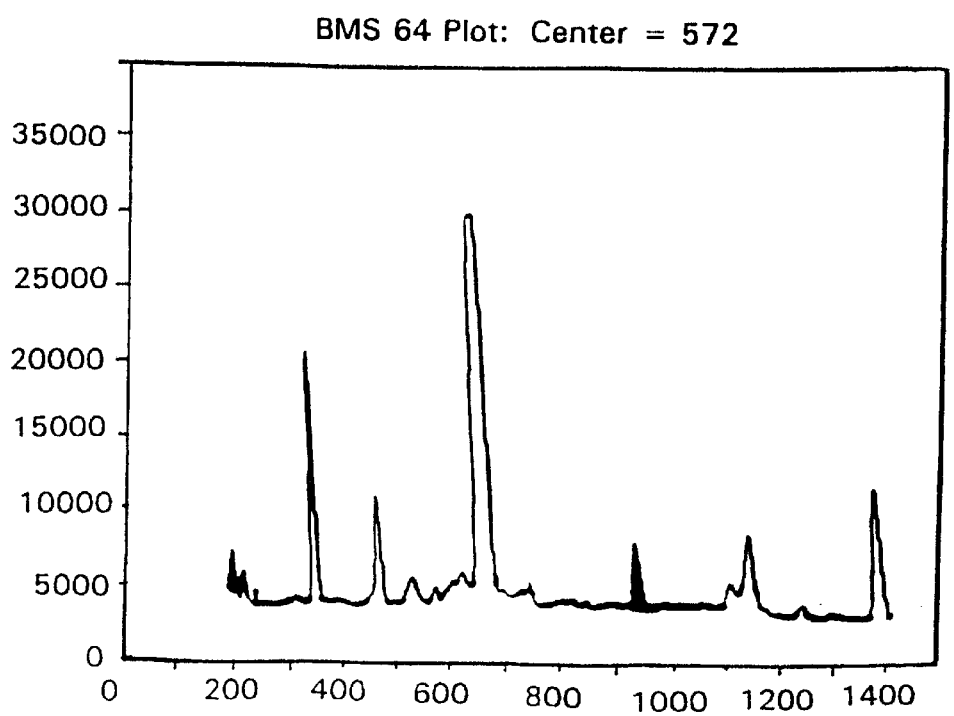
Figure 10:
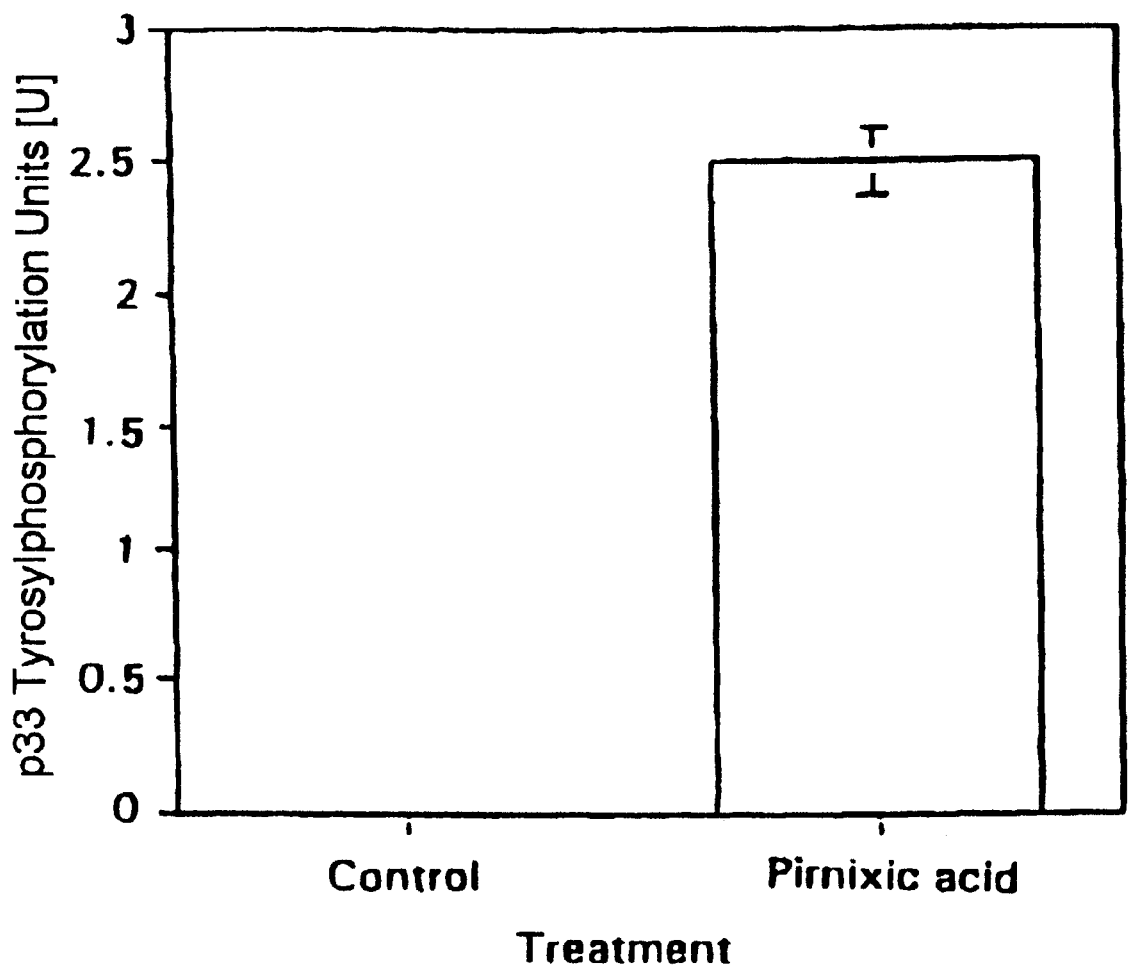
FIG. 10. Bar graph depicting the quantification of the results of the scanning densitometry. The phosphotyrosyl protein quantified from the anti-phosphotyrosine immunoblot was at 33 kDa. Results indicate that the administration of five, twice-daily doses of pirnixic acid (50 mg/kg each dose) produces enhanced tyrosylphosphorylation of p33 compared to control animals, which exhibit no tyrosylphosphorylation at 33 kDa. Each group on the graph represents the average of two rats. Error bars represent the 10 percent coefficient of variation in the quantification of density.

Immunoblotting analysis—As seen in FIG. 8, seven proteins exhibited an increased tyrosine phosphorylation in response to the administration of pirnixic acid. A 6.24-fold increase was noted in pp69, while the greatest relative difference in peak height was seen with a 13.16-fold increase in pp33. Five phosphotyrosylproteins also evidenced a decrease in quantity. These were pp84, pp61, pp43, pp34 and pp23. FIG. 9 depicts the scanning results and FIG. 10 shows the quantification of the CDK at 33 kDa. Results indicate that the administration of five, twice-daily doses of pirnixic acid (50 mg/kg each dose) produces enhanced tyrosylphosphorylation of the CDK compared to control animals, which exhibit no tyrosylphosphorylation of CDK at 33 kDa. Each group on the graph represents the average of two rats. Error bars in this figure represent the 10 percent coefficient of variation in the quantification of density.

Figure 11:
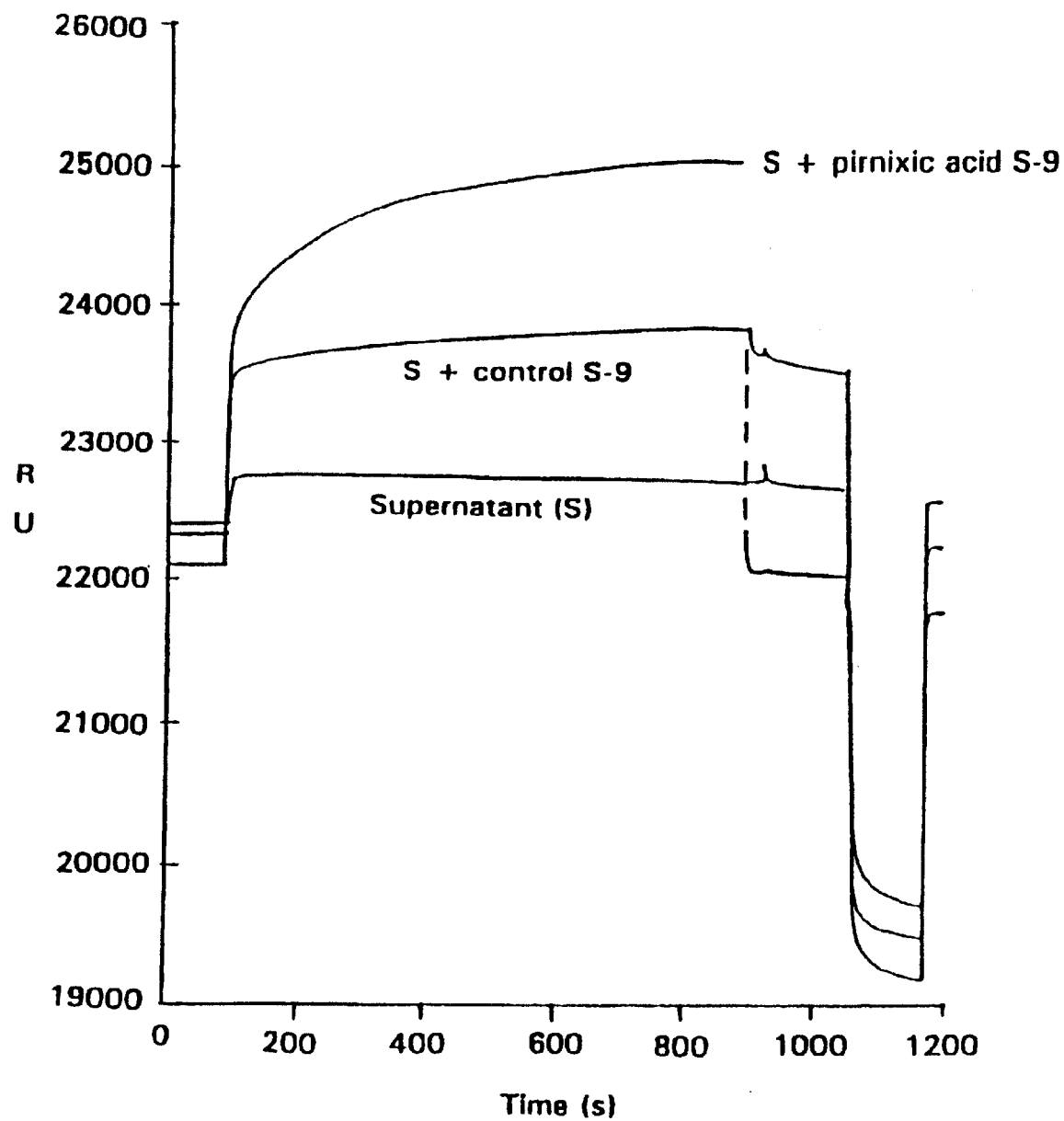
FIG. 11. BIAcore® sensorgram displaying binding of pirnixic acid-treated S-9 protein and control S-9 protein over immobilized anti-cdc2 PSTAIR (SEQ.ID.NO:1) monoclonal antibody.
Figure 12:
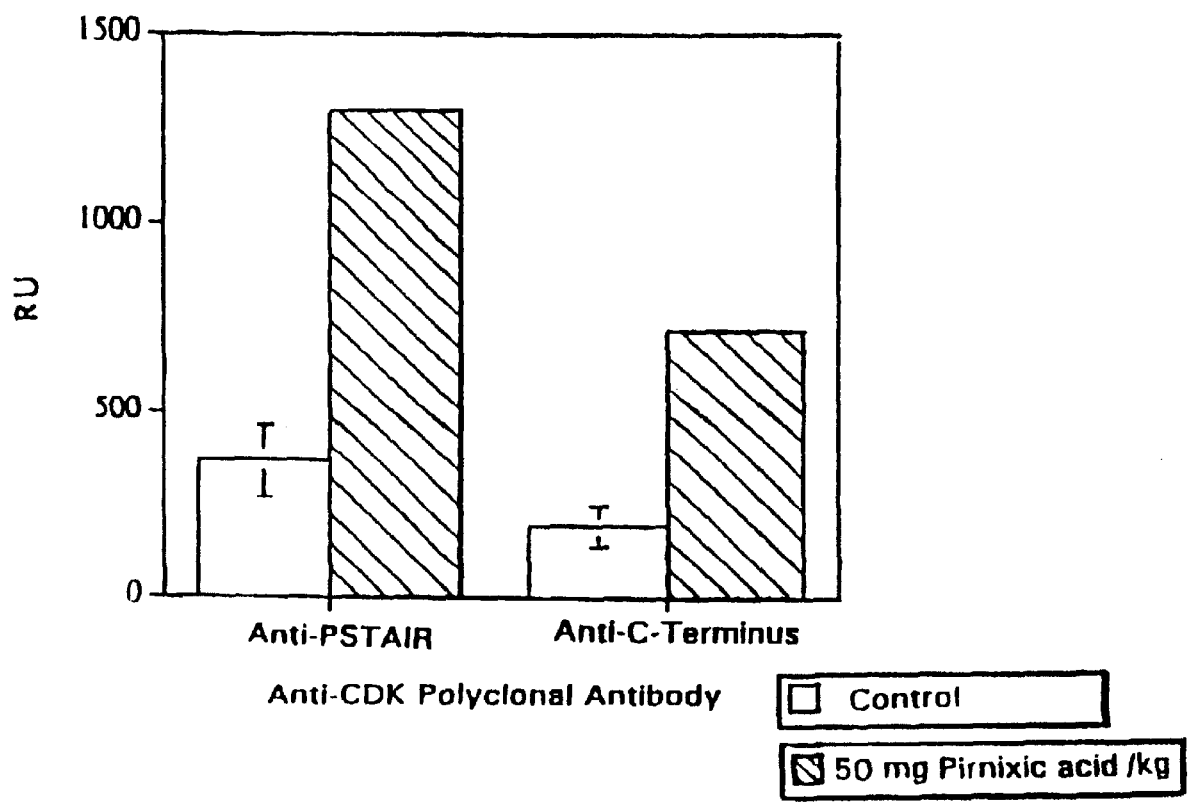
FIG. 12. Summary bar graph depicting BIAcore® quantification of the interaction of tyrosylphosphorylated cyclin dependent kinases (CDK) with anti-CDK monoclonal antibodies (PSTAIR (SEQ.ID.NO:1) and C-terminus) from control and pirnixic acid-treated rats. Error bars represent standard deviations of n=6 (anti-PSTAIR) and n=8 (anti-C Terminus) control rats. RU (response units) value for pirnixic acid-treated rats represents the mean of 2 animals. The treatment of rats with 50 mg pirnixic acid/kg twice a day for 5 days results in enhanced tyrosylphosphorylation of CDK ($p_{34}^{cdc2}$ kinase) compared to control rats.

BIAcore (SPR)—Hepatic S-9 samples from rats treated with pirnixic acid produced greater binding to both anti-PSTAIR or anti-C-terminus antibodies than hepatic S-9 samples from vehicle control rats (FIG. 11). This increased binding exhibited by the hepatic S-9 of test animals is due to enhanced tyrosylphosphorylation of cdc2 kinase (CDK). FIG. 12 is a summary bar graph depicting BIAcore® quantification of the interaction of tyrosylphosphorylated cyclin dependent kinases (CDK) with anti-CDK polyclonal antibodies (PSTAIR (SEQ.ID.NO:1) and C-terminus) from control and pirnixic acid-treated rats. Error bars represent standard deviations of n=6 (anti-PSTAIR) and n=8 (anti-C-terminus) control rats. RU value for pirnixic acid-treated rats represents the mean of 2 animals. The treatment of rats with 50 mg pirnixic acid/kg twice a day for 5 days results in enhanced tyrosylphosphorylation of CDK (p34$^{cdc2}$ kinase) compared to control rats.

EXAMPLE 3

Enhanced tyrosylphosphorylation of p34$^{cdc2}$ kinase in an hepatic cytosol preparation (S-9) from young male rats 24 hours following administration of the nongenotoxic carcinogen diethylhexylphthalate Summary p34$^{cdc2}$ is the serine/threonine kinase subunit of M-phase promoting factor (MPF) (29–31). The regulation of p34$^{cdc2}$ tyrosine phosphorylation status is considered the control mechanism for entry into $G_1$ from $G_0$, the START signal, and also from $G_2$ to M, the initiation of mitosis. It is demonstrated that twice daily doses of 500 mg diethylhexylphthalate/kg of body weight for 5 days to young, male rats increases the extent of tyrosylphosphorylation of hepatic p34$^{cdc2}$ kinase compared to corn oil treated controls. These results indicate that the proliferative stimulus of the nongenotoxic carcinogen diethylhexylphthalate may be quantified as an increase in hepatic p34$^{cdc2}$ kinase tyrosylphosphorylation and therefore that stimulation of tyrosylphosphorylation of hepatic p34$^{cdc2}$ kinase can serve to indicate the capacity of chemicals that are termed peroxisome proliferators to function in vivo as a nongenotoxic carcinogen.

Materials and Methods

Chemicals

Diethylhexylphthalate (DEHP) [CAS 117-81-7] was purchased from Fluka Chemicals (Ronkonkoma, N.Y.). Anti-phosphotyrosine monoclonal, anti-PSTAIR (CDK), and anti-p34$^{cdc2}$ kinase C-terminus polyclonal antibodies were obtained from UBI (Lake Placid, N.Y.). Bicinchoninic acid was obtained from Pierce (Rockford, Ill.). Molecular weight standards were supplied through BioRad (Melville, N.Y.). All other chemicals were purchased from Sigma (St. Louis, Mo.) and were of the highest purity available.

Animals and dosing

Rats are purchased and handled as described in Example 2.

After a wk of acclimation to new surroundings, treatments are begun. The treatment consists of twice daily doses of DEHP administered by oral gavage. The DEHP is dissolved in corn oil. Sham-treated animals are given an equal volume of plain corn oil. Doses are adjusted daily on the basis of weight. The volume of corn oil is generally on the order of 2 mL/rat throughout the treatment period. The second dose is given between the h of 13:00–16:00, approximately 6 h after the first dose given between the h of 7:00–10:00. The DEHP is administered for 5 days at a dose of 500 mg/kg twice a day. Rats are anesthetized and livers are prepared as described in Example 2.

Gel electrophoresis and immunoblotting with anti-phosphotyrosine

These procedures are carried out essentially as described in Example 1 except that anti-phosphotyrosine antibody is used in place of anti-PSTAIR antibody.

Protein determination

This procedure is performed as described in Example 2.

Real-time quantification of total tyrosylphosphorylated p34$^{cdc2}$ kinase and interpretation of the results These procedures are performed as described in Example 2.

Results

Figure 13:
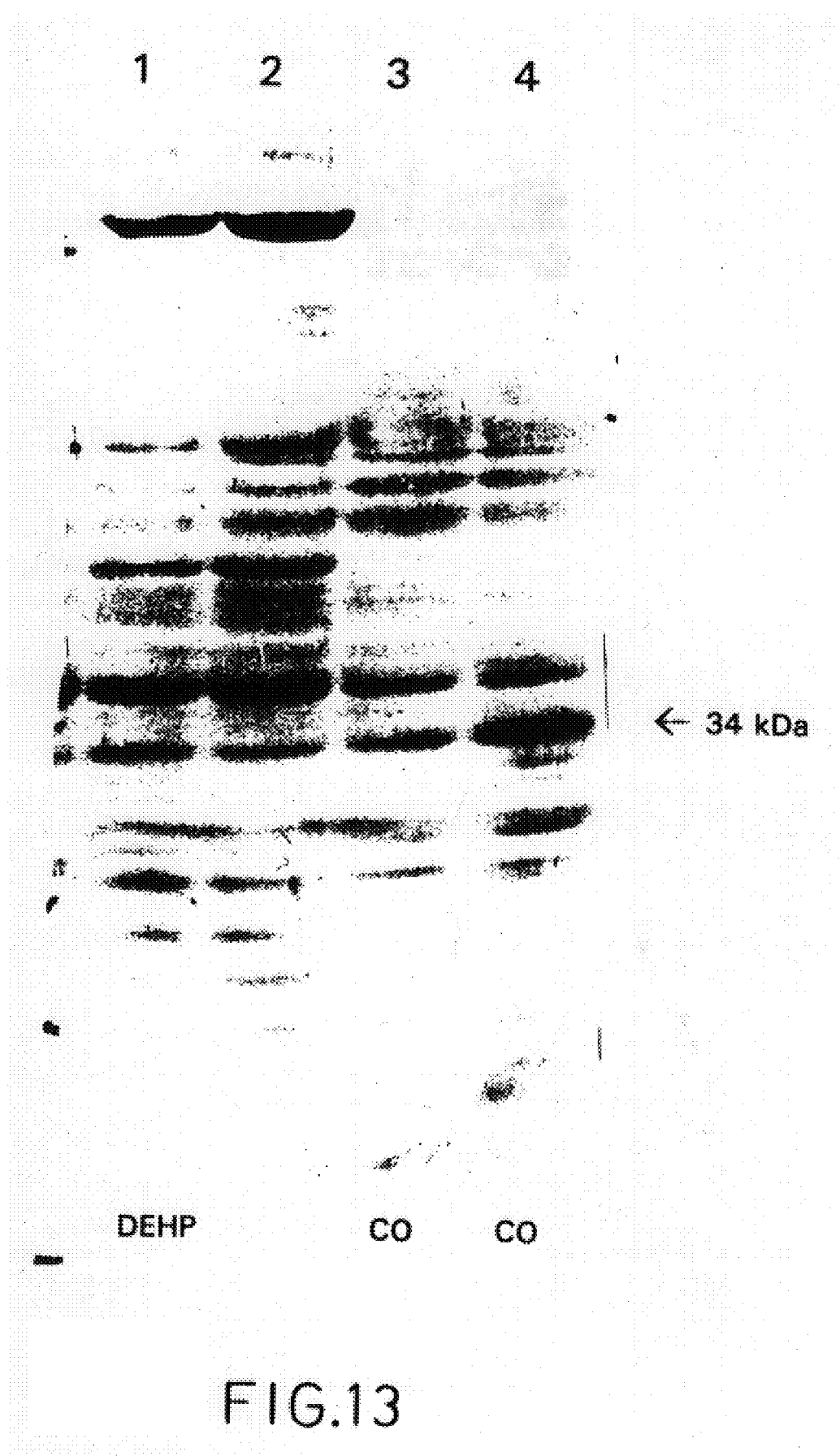
FIG. 13. Anti-phosphotyrosine immunoblots of rat hepatic S-9 protein separated using 11% SDS-PAGE gels for diethylhexylphthalate-treated (lanes 1,2) and control (3,4) rats. Each lane represents a single rat.
Figure 14A:
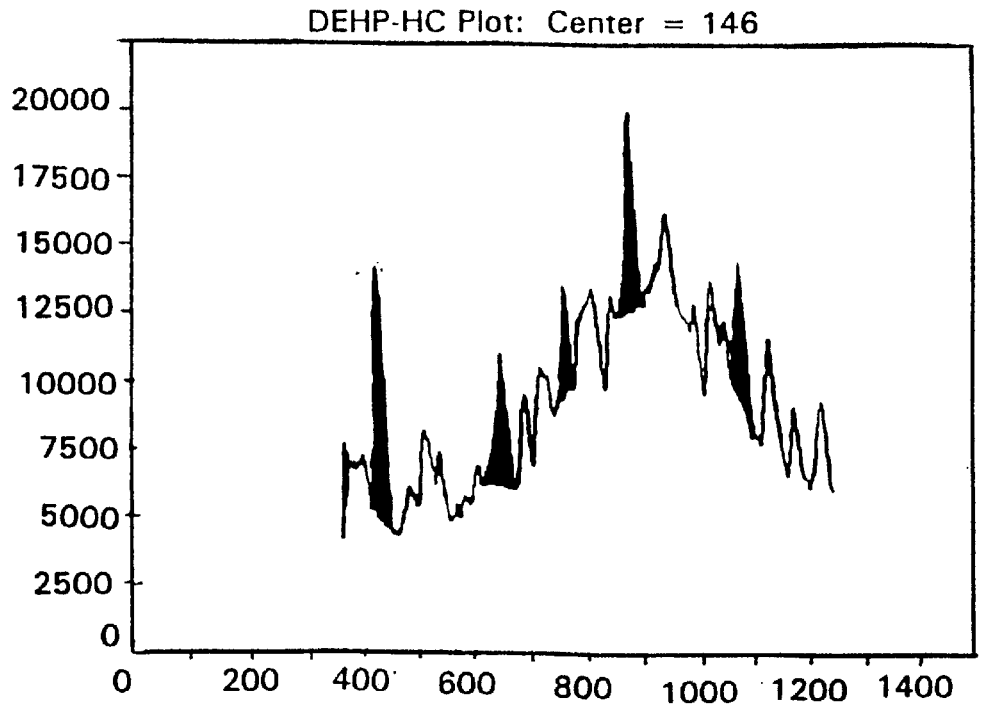
FIG. 14. Scanning densitometry of anti-phosphotyrosine immunoblots for diethylhexylphthalate-treated rats [A and B] and paired vehicle controls [C and D, respectively]. Bolding of peaks indicates difference of greater than 40 percent between treatment and control.
Figure 14B:
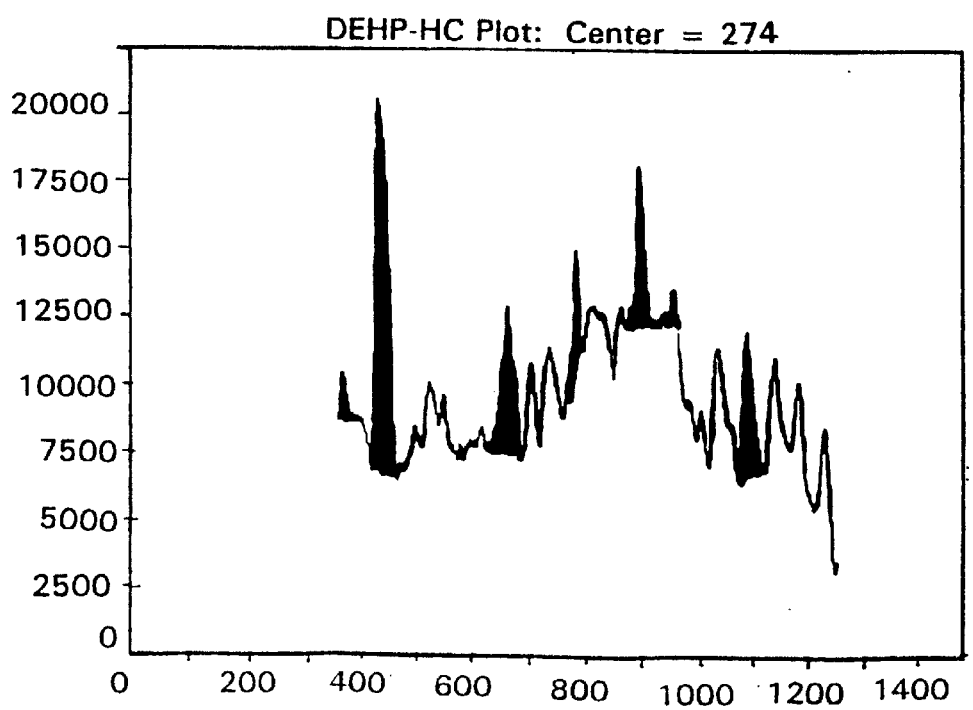
Figure 14C:
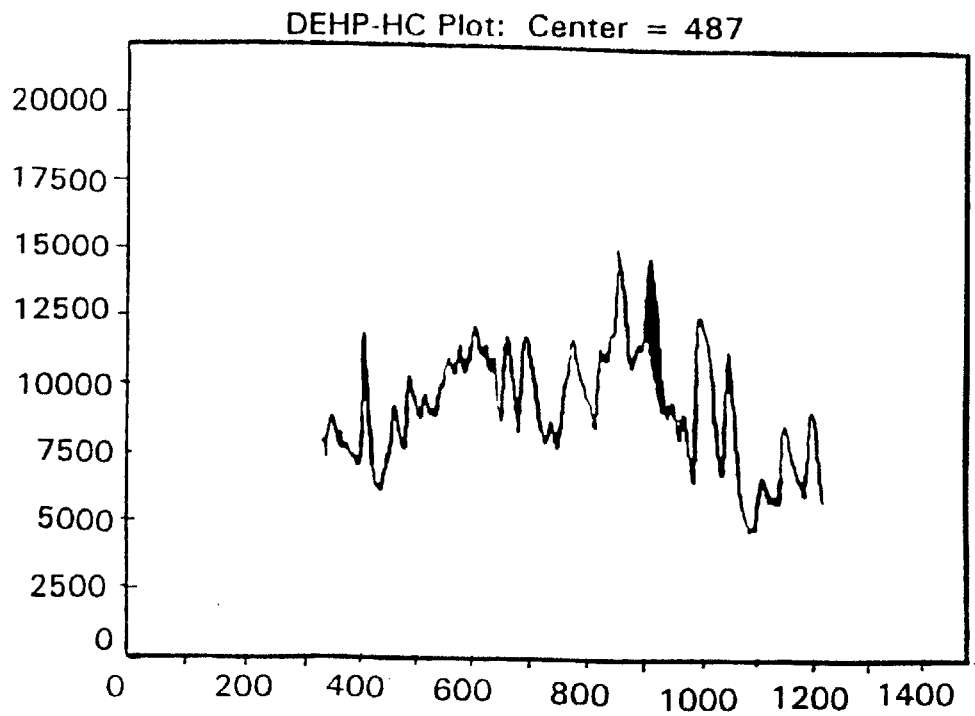
Figure 14D:
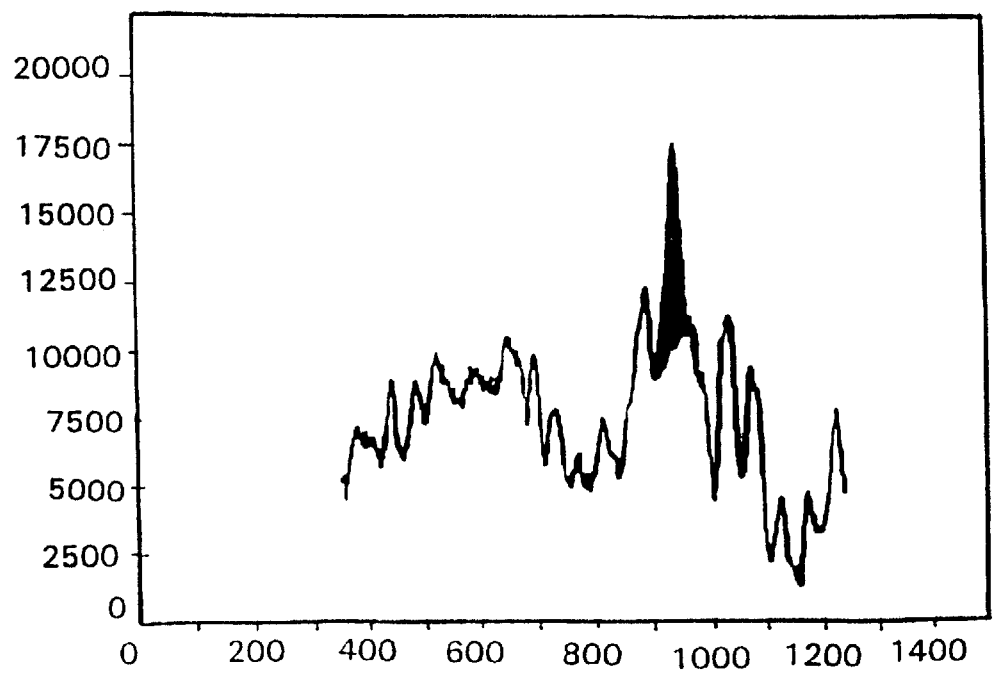
Figure 15:
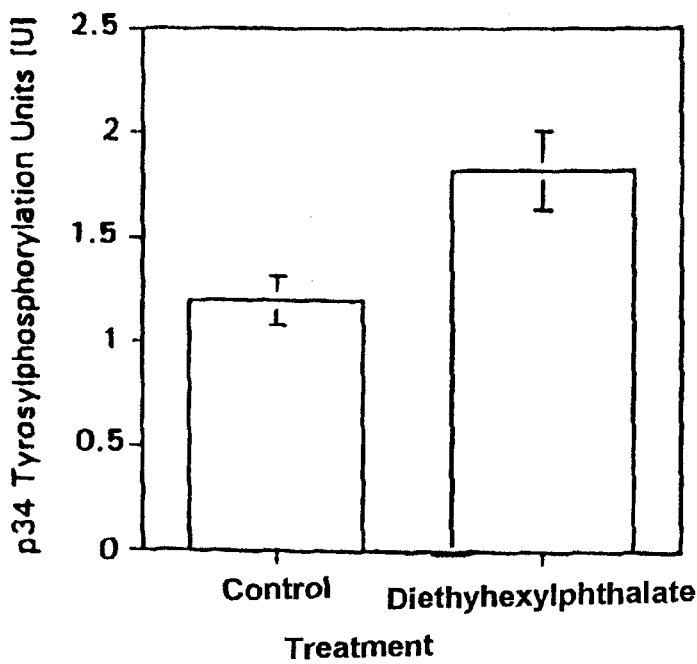
FIG. 15. Bar graph depicting the quantification of the results of the scanning densitometry. The phosphotyrosyl protein quantified from the anti-phosphotyrosine immunoblot was at 34 kDa. Results indicate that the administration of five, twice-daily doses of diethylhexylphthalate (500 mg/kg each dose) produces enhanced tyrosylphosphorylation of the p34 compared to control animals, which exhibit no tyrosylphosphorylation at 34 kDa. Each group on the graph represents the average of two rats. Error bars represent the 10 percent coefficient of variation in the quantification of density.

Immunoblotting analysis—Six phosphotyrosylproteins are shown to increase with the administration of DEHP (FIGS. 13 and 14). The range of relative increase is 1.48 to 4.19-fold. A decrease in pp31 and pp28 is also observed. FIG. 15 depicts the quantification of the results of the scanning densitometry. The cyclin dependent kinase (CDK) quantified from the anti-phosphotyrosine immunoblot is at 34 kDa. Results indicate that the administration of five, twice-daily doses of DEHP (500 mg/kg each dose) produces enhanced tyrosylphosphorylation of the CDK compared to control animals, which exhibit no tyrosylphosphorylation of CDK at 34 kDa. Each group on the graph represents the average of two rats. Error bars represent the 10 percent coefficient of variation in the quantification of density.

Figure 16:
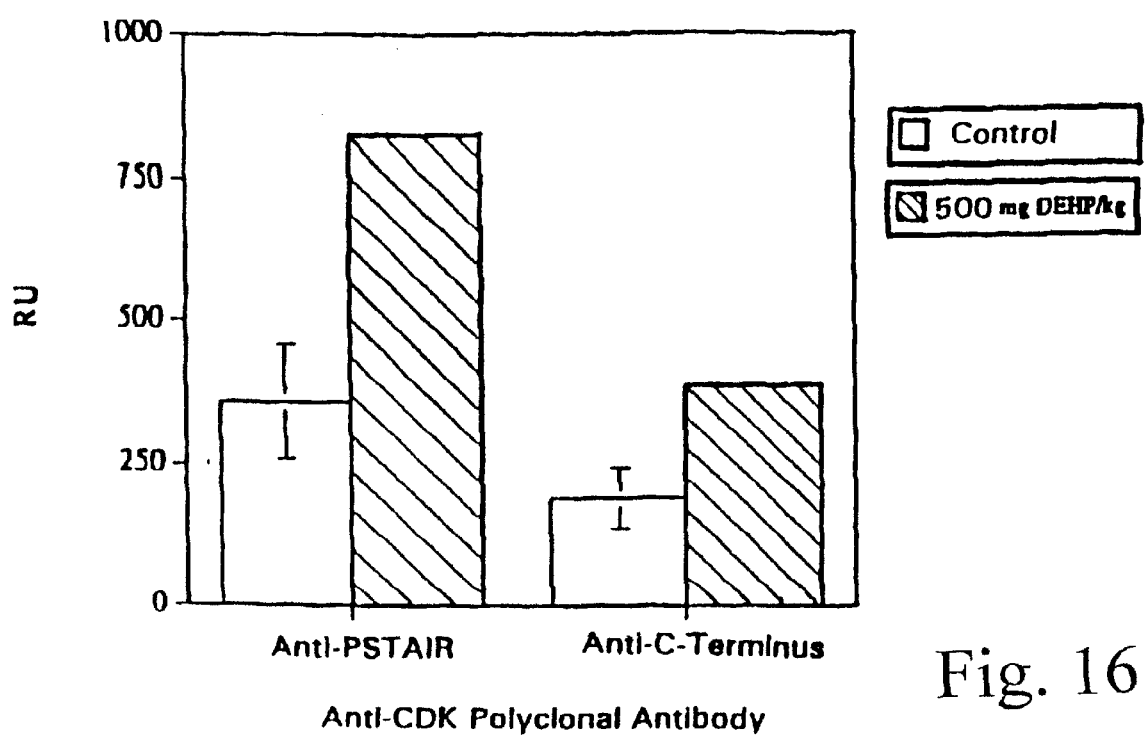
FIG. 16. Summary bar graph depicting BIAcore® quantification of the interaction of tyrosylphosphorylated cyclin dependent kinases (CDK) with anti-CDK monoclonal antibodies (PSTAIR (SEQ.ID.NO:1) and C-terminus) from control and diethylhexylphthalate-treated rats. Error bars represent standard deviations of n=6 (anti-PSTAIR) and n=8 (anti-C Terminus) control rats. RU value for diethylhexylphthalate-treated rats represents the mean of 2 animals. The treatment of rats with 500 mg diethylhexylphthalate/kg twice a day for 5 days produces enhanced tyrosylphosphorylation of CDK (p34$^{cdc2}$ kinase) compared to control rats.
Figure 18A:
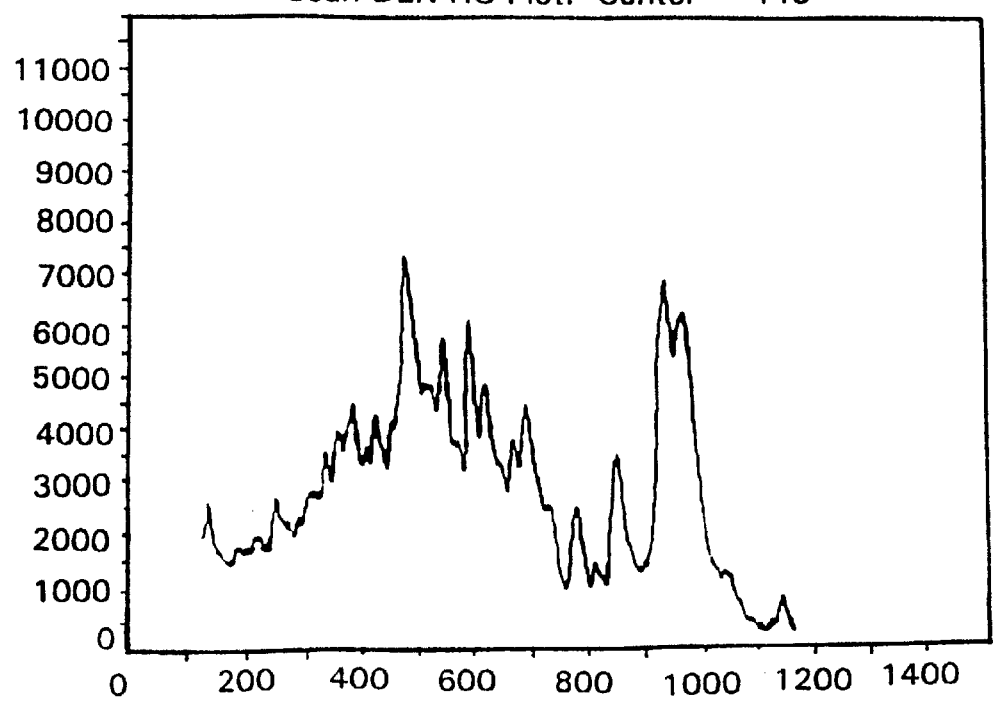
FIG. 18. Scanning densitometry of anti-phosphotyrosine immunoblots for diethylnitrosamine-treated rats [A and B] and paired vehicle controls [C and D, respectively]. Bolding of peaks indicates difference of greater than 40 percent between treatment and control.
Figure 18B:
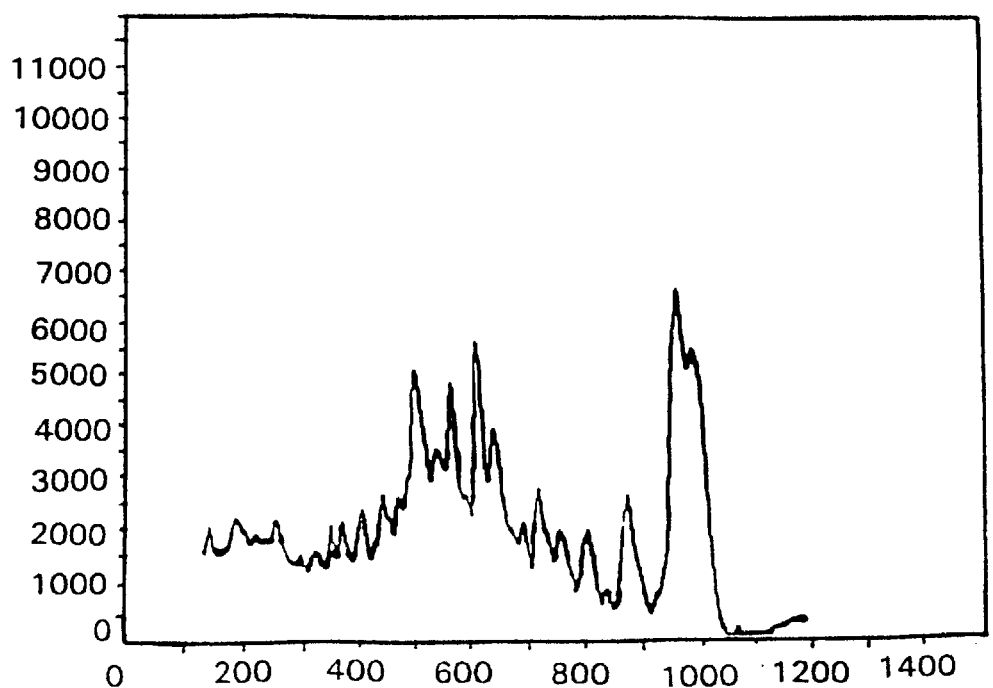
Figure 18C:
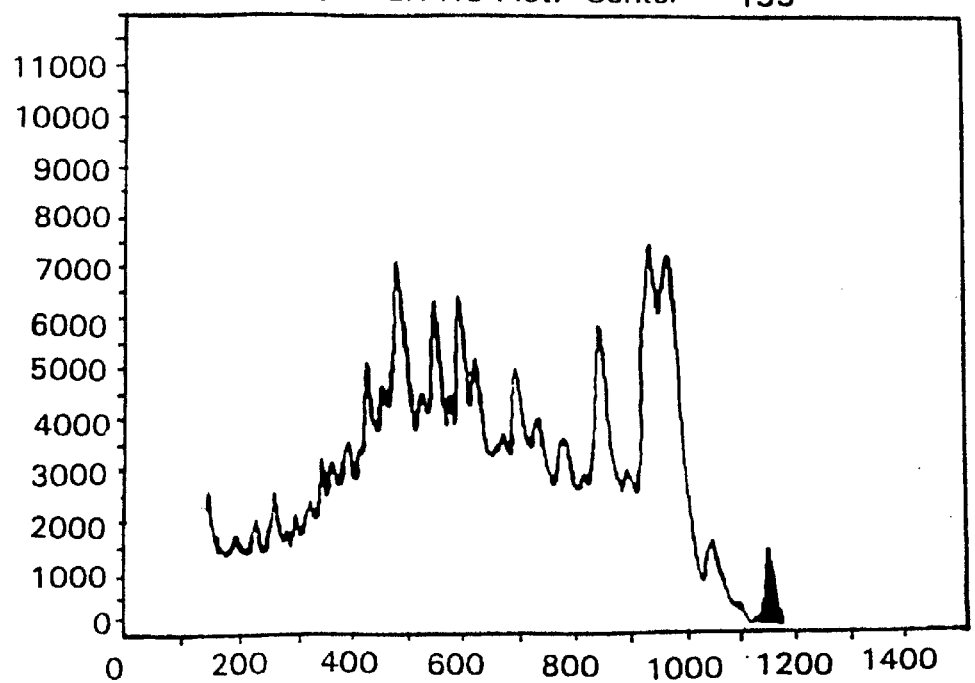
Figure 18D:
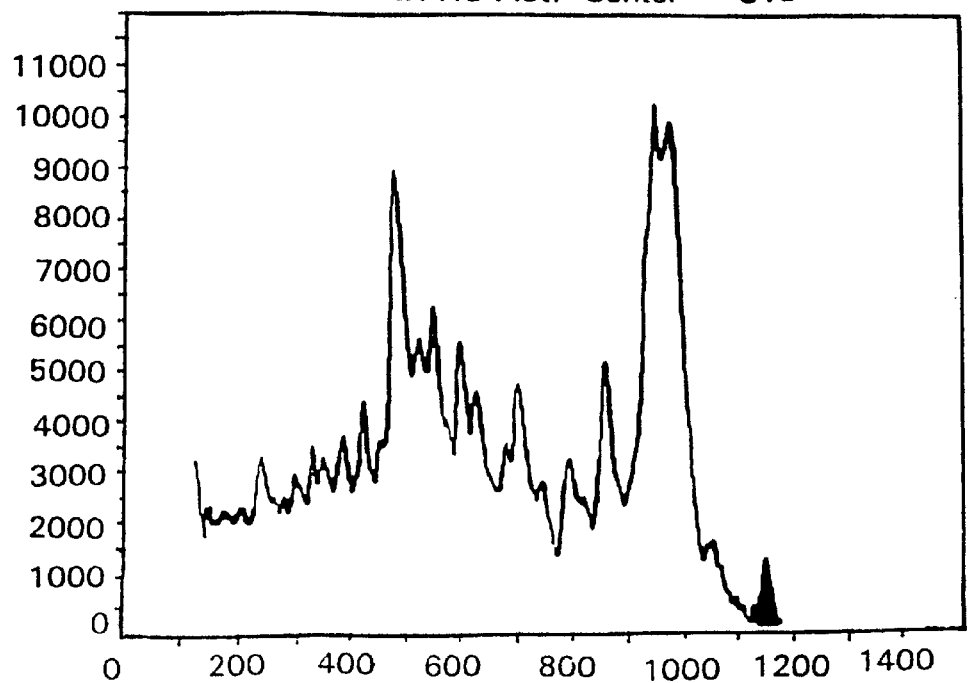

BIAcore (SPR)—Hepatic S-9 samples from rats treated with DEHP produce greater binding to both anti-PSTAIR or anti-C-terminus antibodies than hepatic S-9 samples from vehicle control rats (FIG. 16). This increase in binding by the hepatic S-9 of DEHP-treated animals is due to enhanced tyrosylphosphorylation of cdc2 kinase (CDK). FIG. 16 is a summary bar graph depicting BIAcore® quantification of the interaction of tyrosylphosphorylated cyclin dependent kinases (CDK) with anti-CDK polyclonal antibodies (PSTAIR (SEQ.ID.NO:1) and C-terminus) from control and DEHP-treated rats. Error bars represent standard deviations of n=6 (anti-PSTAIR) and n=8 (anti-C-terminus) control rats. RU value for DEHP-treated rats represents the mean of 2 animals. The treatment of rats with 500 mg DEHP/kg twice a day for 5 days results in enhanced tyrosylphosphorylation of CDK (p34$^{cdc2}$ kinase) compared to control rats.

EXAMPLE 4

The genotoxic carcinogen diethylnitrosamine does not enhanced tyrosylphosphorylation of p34$^{cdc2}$ kinase in an hepatic cytosol preparation (S-9) from young male rats 24 hours following administration Summary p34$^{cdc2}$ is the serine/threonine kinase subunit of M-phase promoting factor (MPF) (29–31). The regulation of p34$^{cdc2}$ tyrosine phosphorylation status is considered the control mechanism for entry into $G_1$ from $G_0$, the START signals, and also from $G_2$ to M, the initiation of mitosis. It is demonstrated that twice daily doses of 500 mg diethylnitrosamine/kg of body weight for 5 days to young, male rats did not affect the extent of tyrosylphosphorylation of hepatic p34$^{cdc2}$ kinase compared to corn oil treated controls. These results indicate that the early in vivo effects of the genotoxic carcinogen diethylnitrosamine can not be quantified through a change in hepatic p34$^{cdc2}$ kinase tyrosylphosphorylation and therefore that stimulation of tyrosylphosphorylation of hepatic p34$^{cdc2}$ kinase is specific for nongenotoxic carcinogens.

Materials and Methods
Chemicals

Diethylnitrosamine (DEN) [CAS 55-18-5] was purchased from Fluka Chemicals (Ronkonkoma, N.Y.). Anti-phosphotyrosine monoclonal, anti-PSTAIR (CDK), and anti-p34$^{cdc2}$ kinase C-terminus polyclonal antibodies were obtained from UBI (Lake Placid, N.Y.). Bicinchoninic acid was obtained from Pierce (Rockford, Ill.). Molecular weight standards were supplied through BioRad (Melville, N.Y.). All other chemicals were purchased from Sigma (St. Louis, Mo.) and were of the highest purity available.

Animals and dosing

Animals are purchased and handled as described in Example 2. After a wk of acclimation to new surroundings, treatments are begun. The treatment consists of twice daily doses of DEN administered by oral gavage. The DEN is dissolved in corn oil. Sham-treated animals are given an equal volume of plain corn oil. Doses are adjusted daily on the basis of weight. The volume of corn oil is generally on the order of 2 mL/rat throughout the treatment period. The second dose is given between the h of 13:00–16:00, approximately 6 h after the first dose given between the h of 7:00–10:00. The DEN is administered for 5 days at a dose of 500 mg/kg twice a day. Rats are anesthetized and livers are prepared as described in Example 2.

Gel electrophoresis and immunoblotting with anti-phosphotyrosine

These procedures are carried out as described in Example 1 except that anti-phosphotyrosine antibody is used in place of anti-PSTAIR antibody.

Protein determination

This procedure is performed as described in Example 1. Real-time quantification of total tyrosylphosphorylated p34$^{cdc2}$ kinase and interpretation of the results These procedures are performed as described in Example 2.

Results

Figure 17:
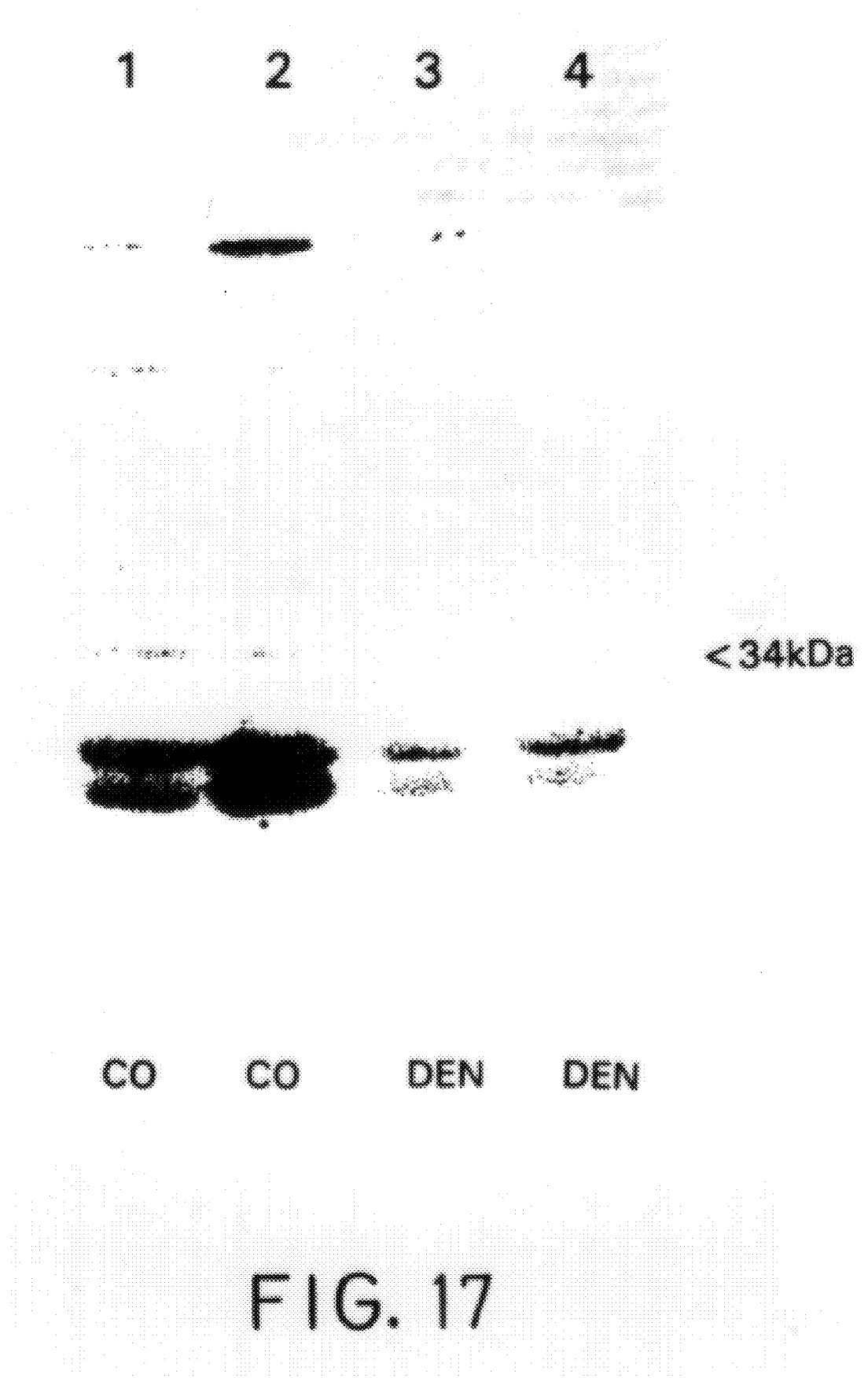
Figure 19:
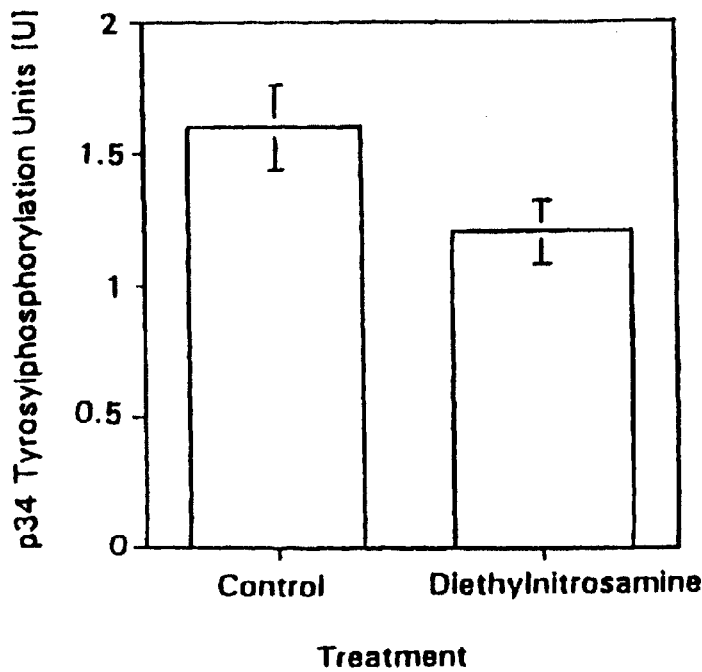
FIG. 19. Bar graph depicting the quantification of the results of the scanning densitometry. The phosphotyrosyl protein quantified from the anti-phosphotyrosine immunoblot was at 34 kDa. Results indicate that the administration of five, twice-daily doses of diethylnitrosamine (500 mg/kg each dose) produces no enhanced tyrosylphosphorylation of p34 compared to control animals. Each group on the graph represents the average of two rats. Error bars represent the 10 percent coefficient of variation in the quantification of density.
Figure 20:
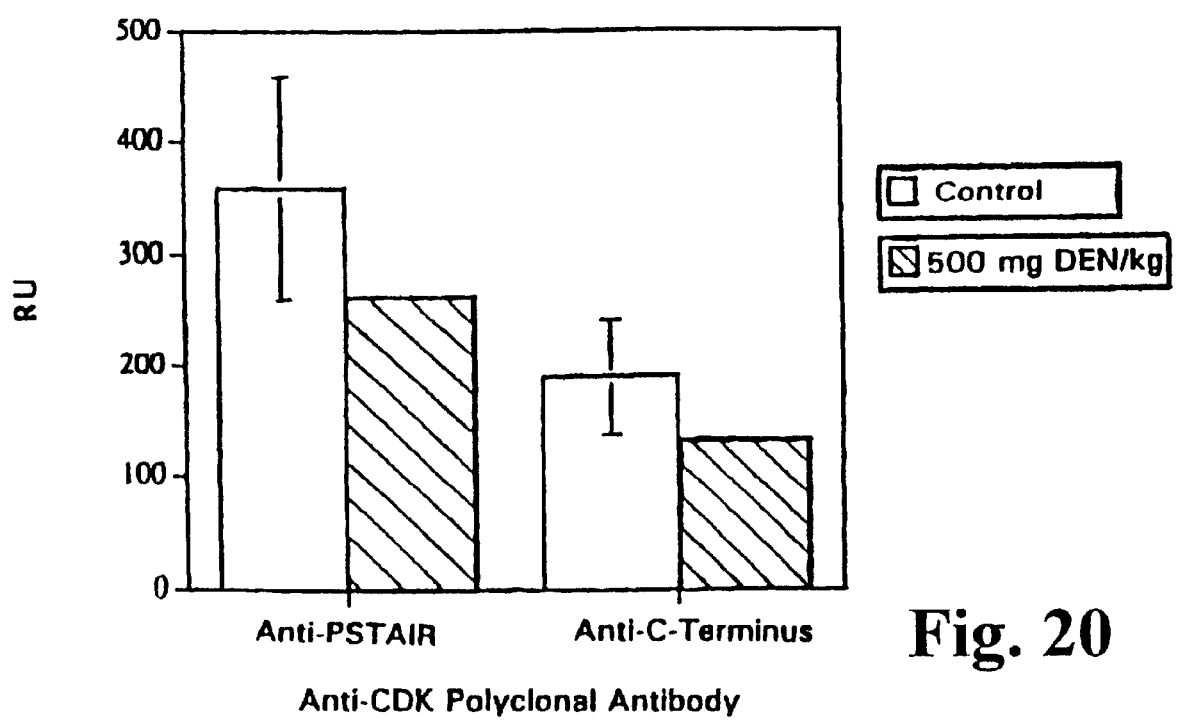
FIG. 20. Summary bar graph depicting BIAcore® quantification of the interaction of tyrosylphosphorylated cyclin dependent kinases (CDK) with anti-CDK polyclonal antibodies (PSTAIR (SEQ.ID.NO:1) and C-terminus) from control and diethylnitrosamine-treated rats. Error bars represent standard deviations of n=6 (anti-PSTAIR) and n=8 (anti-C-terminus) control rats. RU value for diethylnitrosamine-treated rats represents the mean of 2 animals. Results indicate that the treatment of rats with 500 mg diethylnitrosamine/kg twice a day for 5 days produces no enhanced tyrosylphosphorylation of CDK (p34$^{cdc2}$ kinase) compared to control rats.

Immunoblotting analysis—Administration of DEN to young male rats did not produce any increases in phospho-tyrosylproteins (FIGS. 17 and 18). A 61% decrease in pp22 is observed. FIG. 19 is a bar graph depicting the quantification of the results of the scanning densitometry. The band quantified from the anti-phosphotyrosine immunoblot is at 34 kDa. Results indicate that the administration of five, twice-daily doses of DEN (500 mg/kg each dose) produces no enhanced tyrosylphosphorylation of the p34 compared to control animals. Each group on the graph represents the average of two rats. Error bars represent the 10 percent coefficient of variation in the quantification of density. BlAcore (SPR)—Hepatic S-9 samples from rats treated with DEN produce no greater binding to anti-PSTAIR or anti-C-terminus antibodies than hepatic S-9 samples from vehicle control rats. FIG. 20 is a summary bar graph depicting BIAcore® quantification of the interaction of tyrosylphosphorylated cyclin dependent kinases (CDK) with anti-CDK polyclonal antibodies (PSTAIR (SEQ.ID.NO:1) and C-terminus) from control and DEN-treated rats. Error bars represent standard deviations of n=6 (anti-PSTAIR) and n=8 (anti-C Terminus) control rats. RU value for DEN-treated rats represents the mean of 2 animals. Results indicate that the treatment of rats with 500 mg DEN/kg twice a day for 5 days produces no enhanced tyrosylphosphorylation of CDK (p34$^{cdc2}$ kinase) compared to control rats.

EXAMPLE 5

Enhanced tyrosylphosphorylation of p34 in an hepatic cytosol preparation (S-9) from female Beagle dogs following administration of the nongenotoxic carcinogen Aroclor® polychlorinated biphenyls for eleven and one-half weeks Summary It is demonstrated that daily doses of 0.6, 0.8, 4–8, or 5–10 mg/kg of body weight for 11.5 weeks to 2-year old, female Beagle dogs enhances the tyrosine phosphorylation status of an hepatic p34 compared to corn oil treated controls. These results indicate that the early in vivo effects of the nongenotoxic carcinogen Aroclor® polychlorinated biphenyls can be quantified through a change in hepatic p34 tyrosylphosphorylation and therefore that stimulation of tyrosylphosphorylation of hepatic p34 is specific for nongenotoxic carcinogens.

Materials and Methods
Chemicals

Aroclor®1254 polychlorinated biphenyls (PCBs) is purchased from AccuStandard, Inc. (New Haven, Conn.). Anti-phosphotyrosine monoclonal antibody is obtained from UBI (Lake Placid, N.Y.). Bicinchoninic acid is obtained from Pierce (Rockford, Ill.). Molecular weight standards are supplied through BioRad (Melville, N.Y.). All other chemicals were purchased from Sigma (St. Louis, Mo.) or stated suppliers and were of the highest purity available.

Animals and dosing

Five, purebred, 2-year old; female beagle dogs, obtained from Norwich Pharmaceutical (Norwich, N.Y.), are used in this study. All dogs were fully vaccinated, dewormed and specific pathogen free (SPF) for at least 30 days prior to the initiation of the experiment. They are maintained indoors and individually housed according to Public Health service guidelines (NIH publication No. 85-23). At the beginning of the study the dogs weigh between 8.7 and 12.2 kg. Physical observations of the dogs are made daily during the 11.5-wk dosing period of the study.

Each dog is administered either corn oil (controls) or Aroclor® PCBS at 0.6, 0.8, 4 or 5 mg/kg-day for seven wk. From seven to 11.5 wk, the 4 mg/kg-day dose and the 5 mg/kg-day dose are increased to 8 and 10 mg/kg-day, respectively. The corn oil, as well as test material, is administered in a cube of agarose concealed in a small ball of canned dog food. After consumption of the meatball, the dogs are immediately fed their daily caloric requirement of canned food.

Dogs were sacrificed using 2 mL/kg of Fatal Plus (Vortech Pharmaceutical Company, Dearborne, Mich.). Hepatic S-9 fractions were prepared as previously described in Example 1.

Gel electrophoresis and immunoblotting with anti-phosphotyrosine

These procedures are carried out as described in Example 1 with the exception that anti-phosphotyrosine antibody is used in place of anti-PSTAIR antibody.

Protein determination

This procedure is performed as described in Example 1.

Results

Figure 21:
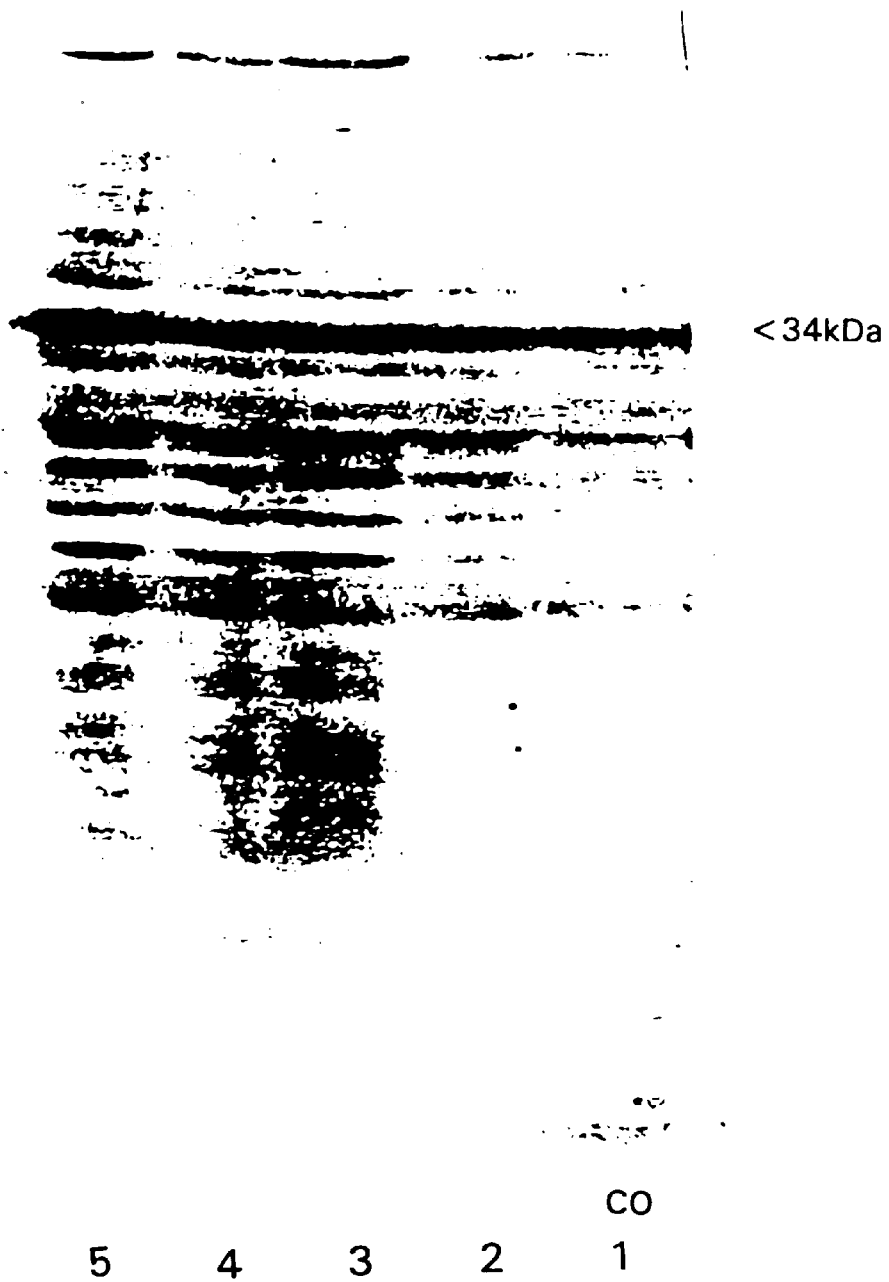
FIG. 21. Anti-phosphotyrosine immunoblot of dog hepatic S-9 protein separated using 11% SDS-PAGE gels for Aroclor®-treated dogs. Lanes 1, 2, 3, 4 and 5 are control, 0.6, 0.8, 4–8, and 5–10 mg Aroclor®/kg-day, respectively.
Figure 22A:
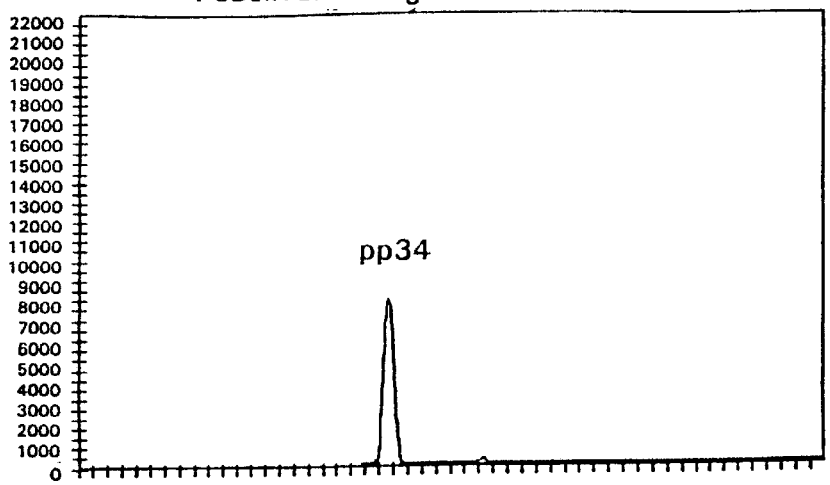
FIG. 22. Scanning densitometry of anti-phosphotyrosine immunoblots at 34 kDa for Aroclor®-treated dogs. From top to bottom the figures represent 0.6, 0.8, 4–8, and 5–10 mg Aroclor®/kg-day, respectively.
Figure 22B:
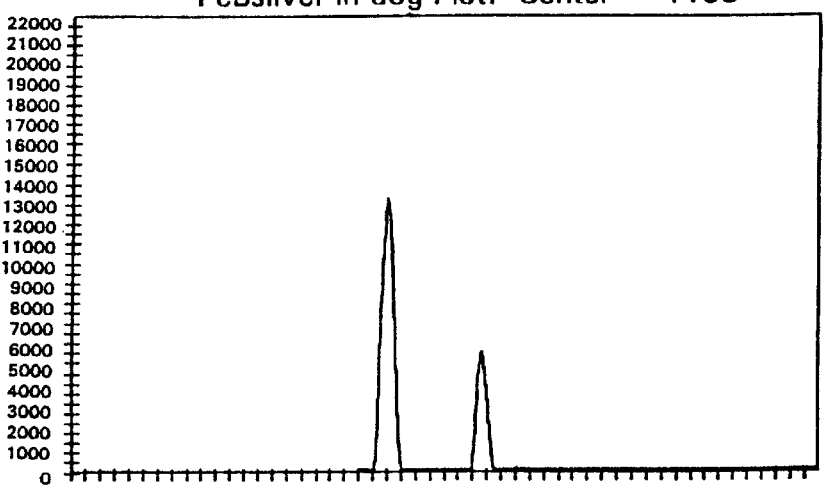
Figure 22C:
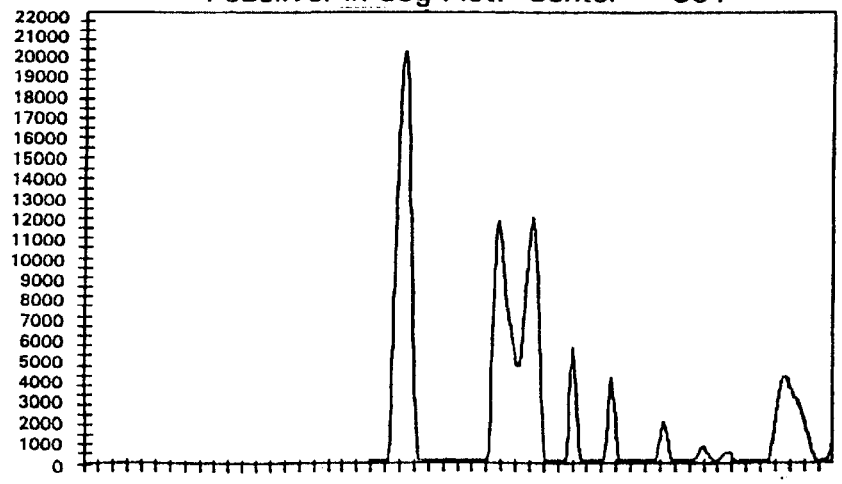
Figure 22D:
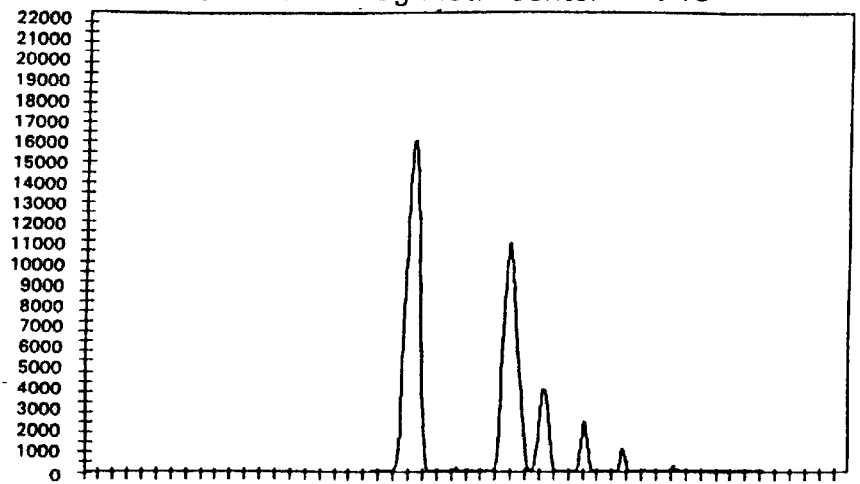
Figure 22E:
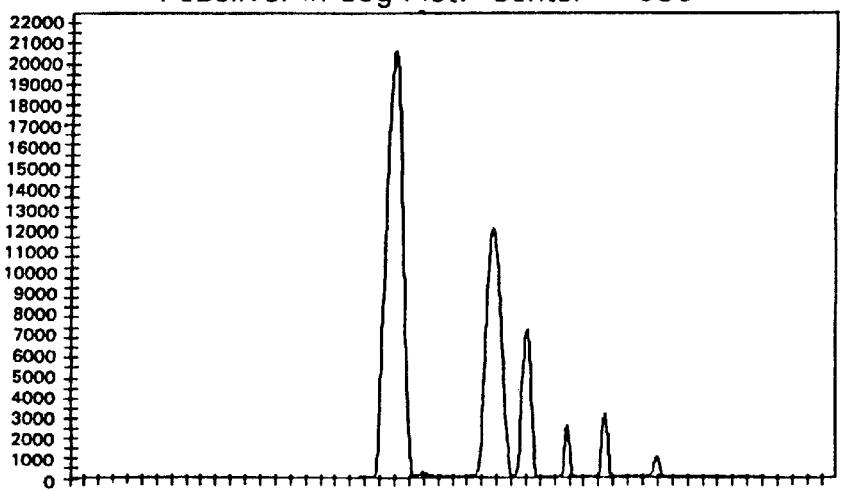
Figure 23:
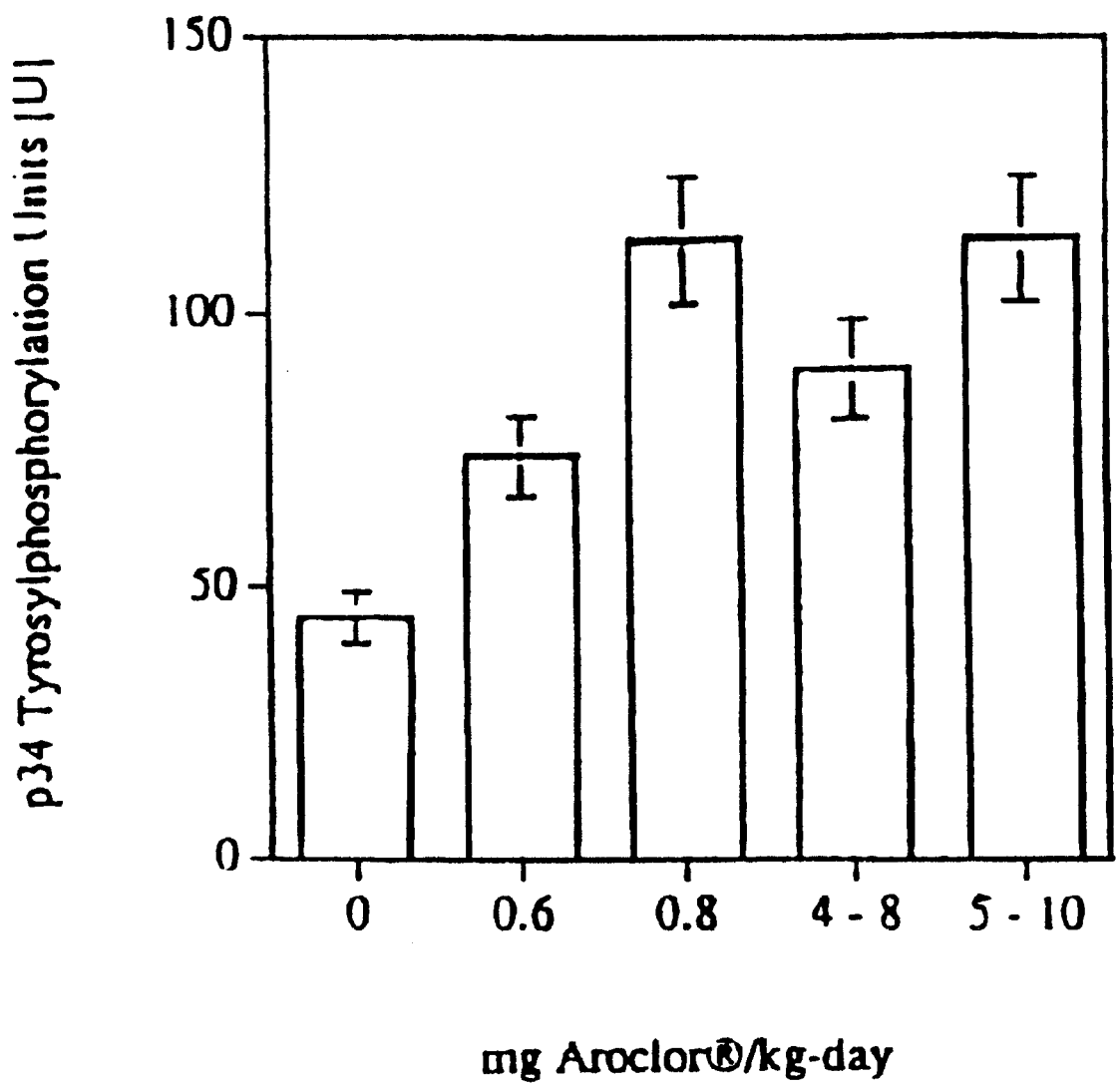
FIG. 23. Bar graph depicting the quantification of the scanning densitometry of the putative cyclin dependent kinase (p34) from the anti-phosphotyrosine immunoblot. The daily administration of Aroclor® for a period of 11.5 weeks results in enhanced tyrosylphosphorylation of the p34 at all doses compared to the control dog. Each bar on the graph represents the result of scanning an immunoblot produced from the hepatic S-9 of a single dog. Error bars represent the 10 percent coefficient of variation in the quantification of density.

The daily administration of Aroclor® polychlorinated biphenyls for a period of 11.5 wk results in enhanced tyrosylphosphorylation of a protein migrating at 34 kDa at all doses compared to the control dog. FIG. 21 depicts the anti-phosphotyrosine immunoblot of dog hepatic S-9 protein separated using 11% SDS-PAGE gels for control and Aroclor® polychlorinated biphenyls-treated dogs. Lanes 1,2,3, 4, and 5 are control, 0.6, 0.8, 4–8, and 5–10 mg Aroclor®/kg-day, respectively. The scanning densitometry of a single band at p34 of the anti-phosphotyrosine immunoblot is presented in FIG. 22. Quantification of the scanning densitometry of p34 is presented in FIG. 23 as a bar graph. Each bar on the graph represents the single result of scanning an immunoblot produced from the hepatic S-9 of one dog. Error bars represent the 10 percent coefficient of variation in the quantification of density.

In Vitro Experiments

EXAMPLE 6

Enhanced tyrosylphosphorylation of p34/p33 (putative CDK) in 3T3 cell lysates 24 hours following exposure to the nongenotoxic carcinogen 2,3,7,8-tetrachlorodibenzo-p-dioxin Summary It is demonstrated that exposure of 3T3 cells to 10 nM 2,3,7,8-tetrachlorodibenzo-p-dioxin for 24 h in a low serum media enhances the tyrosine phosphorylation status of two cell lysate proteins, p34 and p33, compared to dimethylsulfoxide-treated controls. These results indicate that the early in vitro effects of the nongenotoxic carcinogen 2,3,7,8-tetrachlorodibenzo-p-dioxin can be quantified through a change in cellular p34/p33 tyrosylphosphorylation and therefore that stimulation of tyrosylphosphorylation of p34/p33 is specific for nongenotoxic carcinogens.

Materials and Methods

Chemicals 2,3,7,8-Tetrachlorodibenzo-p-dioxin (TCDD) is purchased from AccuStandard, Inc. (New Haven, Conn.). Anti-phosphotyrosine monoclonal antibody is obtained from UBI (Lake Placid, N.Y.). Bicinchoninic acid is obtained from Pierce (Rockford, Ill.). Molecular weight standards are supplied through BioRad (Melville, N.Y.). All other chemicals were purchased from Sigma (St. Louis, Mo.) or stated suppliers and were of the highest purity available.

Tissue culture cells, culture conditions and dosing

3T3 cells (ATCC CCL-92) are purchased from American Type Culture Collection (Bethesda, Md.). These cells are maintained in Dulbecco's Modified Eagle's Medium (DMEM; Gibco cat. #430-2100) supplemented with 10% Fetal bovine serum-heat inactivated (FBS-HI) (Intergen, Purchase, N.Y.). For experimental purposes, the cells are plated in 100 mm×20 mm tissue culture dishes containing 10 mL of the above maintenance medium. The plates are placed in an incubator set at 37° C., 5% $CO_2$, 95% humidity, until they reach confluence (contact inhibited). At this point all the plates are then washed 2× with 5 mL of Dulbecco's calcium- and magnesium-free phosphate buffered saline (CMF-PBS). Four plates are then fed 10 mL of DMEM+ 10% FBS-HI and all the other plates are fed 10 mL of DMEM+0.5% FBS-HI and incubated for 48 h in the above environmental conditions.

After the 48 h incubation period, the medium from the low-serum group (0.5% FBS-HI) was aseptically harvested and allocated into separate tubes containing 40 mL each (to provide 10 mL/plate for 4 plates per treatment). The following concentrations and reagents are added to the appropriate tubes (4 plates/treatment). Dimethyl sulfoxide (DMSO) is used as the diluent for TCDD.

10 mL of DMEM+20% FBS-HI+0.1% DMSO (positive control)

10 mL of DMEM+0.5% FBS-HI+0.1% DMSO 10 mL of DMEM+0.5% FBS-HI+10 nM TCDD

All plates were returned to the incubator for 24 h at the environmental conditions listed above. After the 24 h incubation period, the cells are harvested using the harvesting procedure described.

Gel electrophoresis and immunoblotting with anti-phosphotyrosine

These procedures are carried out as described in Example 1 with the exception that anti-phosphotyrosine antibody is used in place of anti-PSTAIR antibody.

Protein determination

This procedure is performed as described in Example 1.

Results

Figure 24:
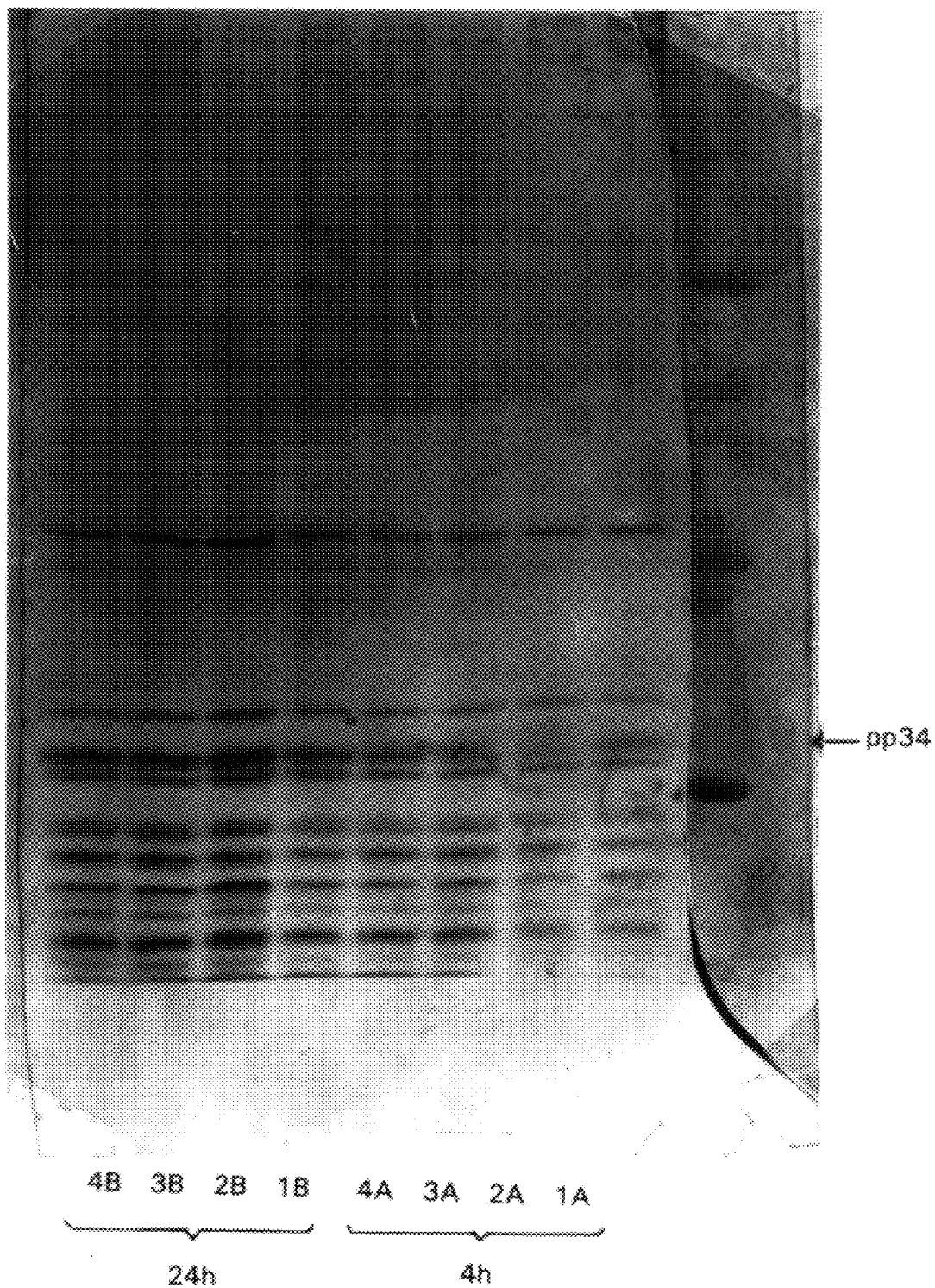
FIG. 24. Anti-phosphotyrosine immunoblots of 3T3 cell lysate protein separated using 11% SDS-PAGE gels for 3T3 cells exposed to 10 nM 2,3,7,8-tetrachlorodibenzo-p-dioxin (lane 3B) or DMSO vehicle (lane 1B) for 24 h in 0.5% serum supplemented media.
Figure 25A:
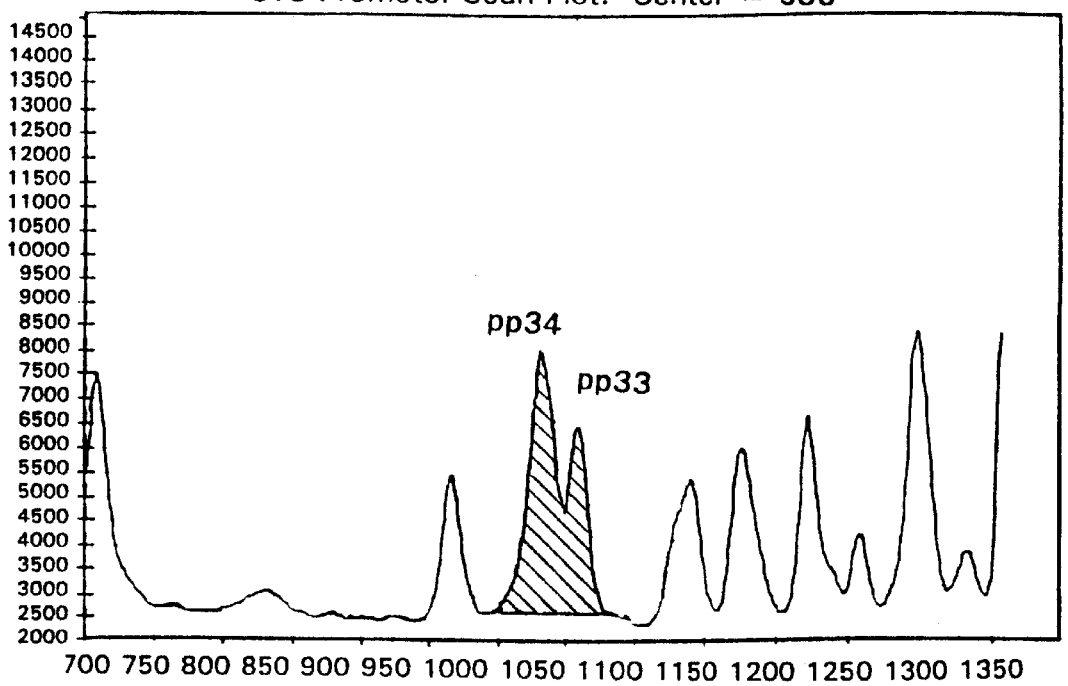
FIG. 25. Scanning densitometry of anti-phosphotyrosine immunoblots for 3T3 cells treated with 2,3,7,8-tetrachlorodibenzo-p-dioxin (TCDD) or DMSO vehicle (Control) for 24 h in 0.5% serum media. Bolded peaks indicate p34 and p33 tyrosylphosphoproteins.
Figure 25B:
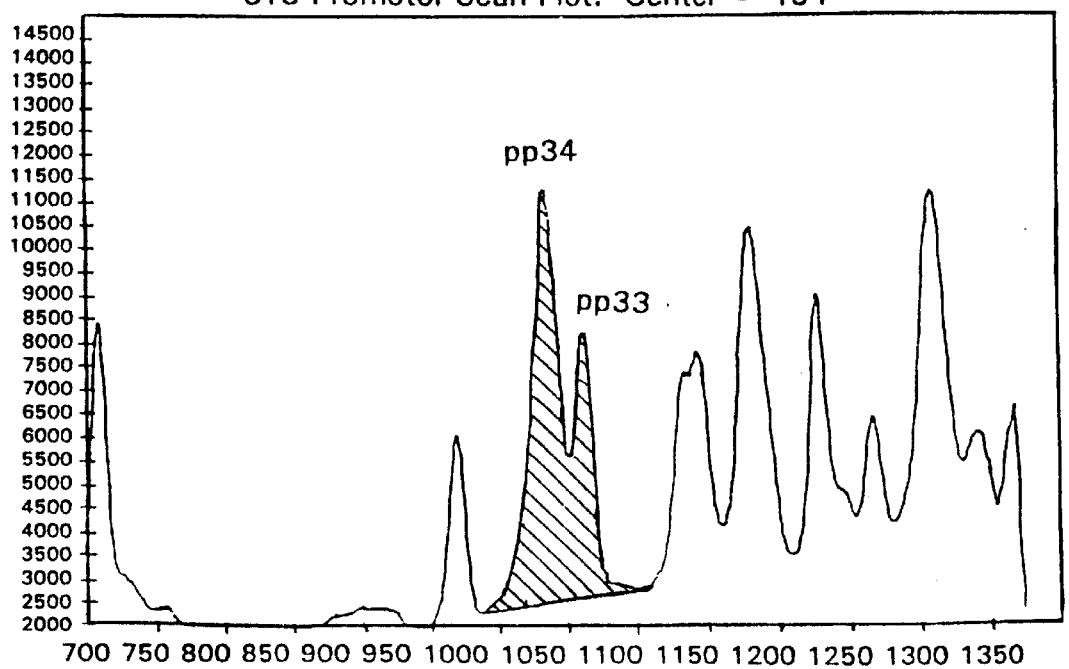
Figure 26:
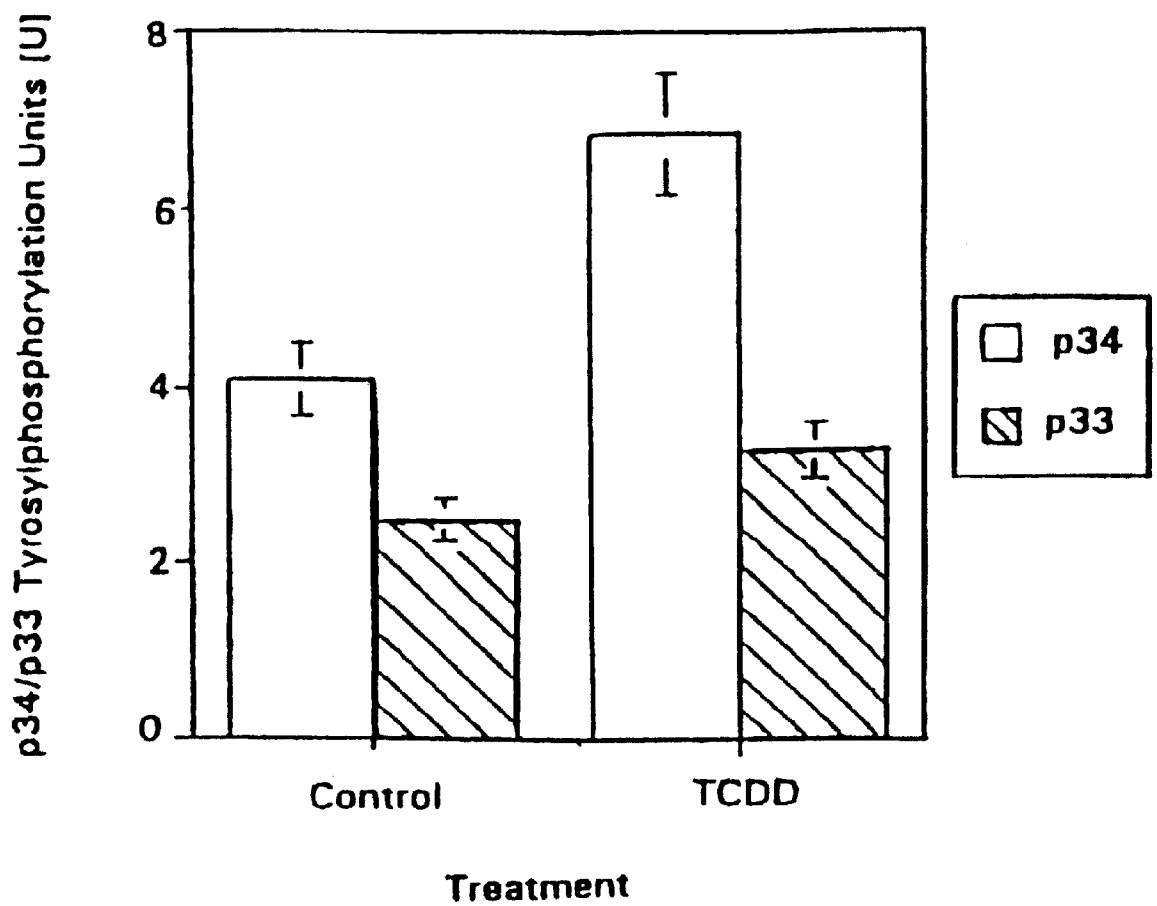
FIG. 26. Bar graph depicting the quantification of the scanning densitometry of the putative cyclin dependent kinases (p34/p33) from the anti-phosphotyrosine immunoblot. Exposure of 3T3 cells to 10 nM 2,3,7,8-tetracholordibenzo-p-dioxin for 24 h results in an increase in tyrosylphosphorylation of p34 and p33 of 67 and 32%, respectively, compared to the vehicle control. Each bar on the graph represents the result of scanning an immunoblot produced from the pooled whole cell lysates of four plates per treatment. Error bars represent the 10 percent coefficient of variation in the quantification of density.

Exposure of 3T3 cells to 10 nM TCDD for 24 h results in an increase in tyrosylphosphorylation of p34 and p33 of 67 and 32%, respectively, compared to the vehicle control. The anti-phosphotyrosine immunoblot of 3T3 cell lysate protein separated using an 11% SDS-PAGE gel for 3T3 cells exposed to 10 nM TCDD is presented in FIG. 24. Results of scanning the control and TCDD-treated lanes are presented in FIG. 25; bolded peaks indicate p34 and p33 tyrosylphosphoproteins. In FIG. 26 the putative cyclin dependent kinases (p34/p33) are quantified from the anti-phosphotyrosine immunoblot. Results of serum supplementation (c.f. immunoblot in FIG. 24, scan results not depicted in FIG. 25) indicate enhanced tyrosylphosphorylation of p34/p33. This result would be expected if the pp34/pp33 are cyclin dependent kinases, since the serum supplemented media provide growth factor that stimulate the cells to mitosis and this stimulus is mediated through the CDK.

EXAMPLE 7

Enhanced tyrosylphosphorylation of p34/p33 (putative CDK) in 3T3 cell lysates 24 hours following exposure to the tumor promotor 12-O-tetra-decanoylphorbol-13-acetate Summary It is demonstrated that exposure of 3T3 cells to 12-O-tetra-decanoylphorbol-13-acetate for 24 h in a low-serum media enhances the tyrosine phosphorylation status of two cell lysate proteins, p34 and p33, compared to dimethylsulfoxide-treated controls. These results indicate that the early in vitro effects of the tumor promotor 12-O-tetra-decanoylphorbol-13-acetate can be quantified through a change in cellular p34/p33 tyrosylphosphorylation and therefore that stimulation of tyrosylphosphorylation of p34/p33 is specific to a mechanism relating to the process of nongenotoxic carcinogenesis.

Materials and Methods
Chemicals

2-O-Tetra-decanoylphorbol-13-acetate (TPA) is purchased from ChemSyn Science Labs (Lenexa, Ky.). Anti-phosphotyrosine monoclonal antibody is obtained from UBI (Lake Placid, N.Y.). Bicinchoninic acid is obtained from Pierce (Rockford, Ill.). Molecular weight standards are supplied through BioRad (Melville, N.Y.). All other chemicals were purchased from Sigma (St. Louis, Mo.) or stated suppliers and were of the highest purity available.

Tissue culture cells, culture conditions and dosing

These procedures are performed as described in Example 6. The following concentrations and reagents are added to the appropriate tubes (4 plates/treatment). Dimethyl sulfoxide (DMSO) is used as the diluent for TPA.

10 mL of DMEM+20% FBS-HI+0.1% DMSO
10 mL of DMEM+0.5% FBS-HI+0.1% DMSO
10 mL of DMEM+0.5% FBS-HI+160 nM TPA

Gel electrophoresis and immunoblotting with anti-phosphotyrosine

These procedures are carried out as described in Example 1 except that anti-phosphotyrosine antibody is used in place of anti-PSTAIR antibody.

Protein determination

This procedure is performed as described in Example 1.

Results

Figure 27:
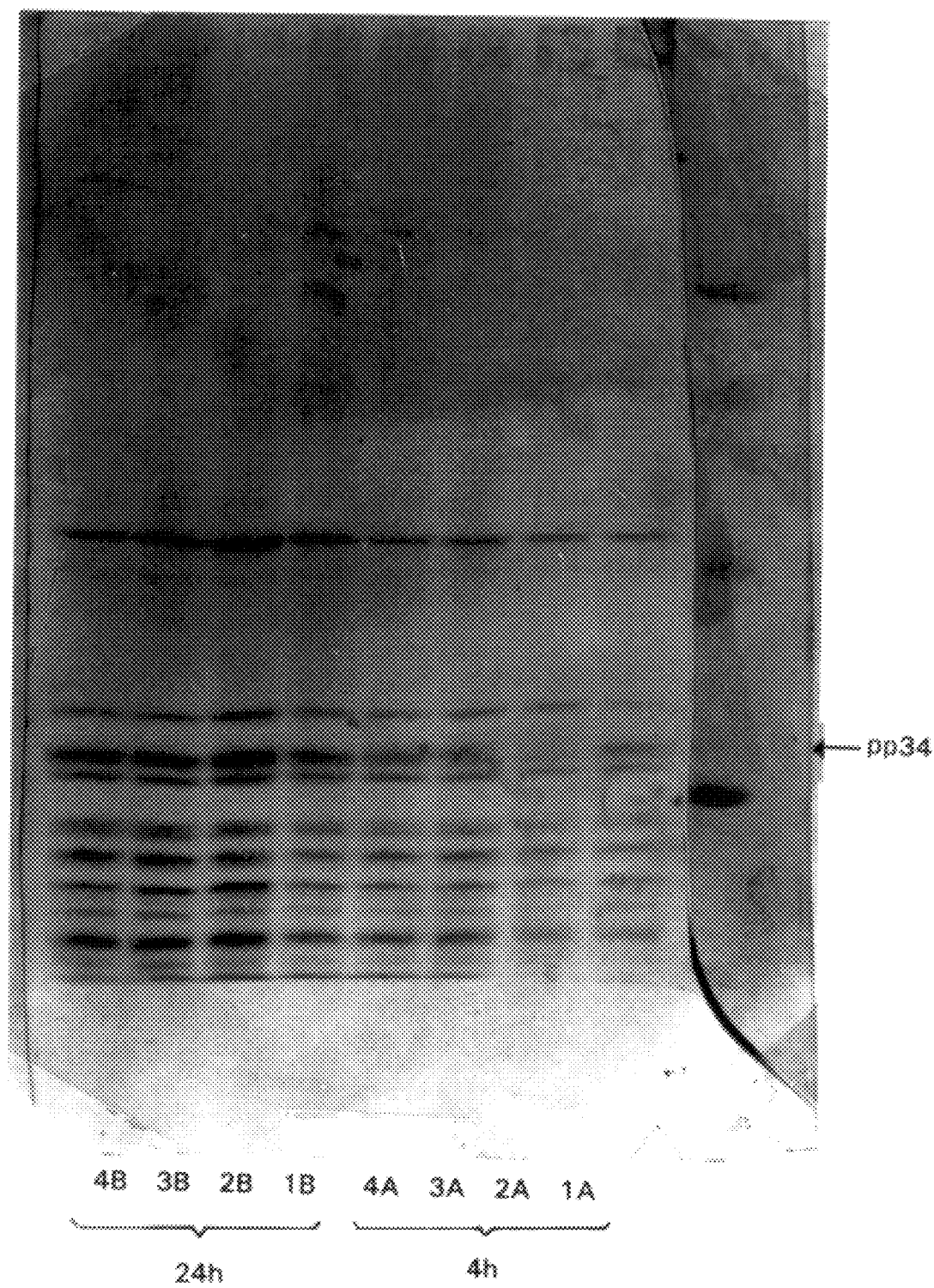
FIG. 27. Anti-phosphotyrosine immunoblots of 3T3 cell lysate protein separated using 11% SDS-PAGE gels for 3T3 cells exposed to 160 nM 12-O-tetra-decanoylphorbol-13-acetate (TPA; lane 4B) or DMSO vehicle (Control; lane 1B) for 24 h in 0.5% serum supplemented media.
Figure 28A:
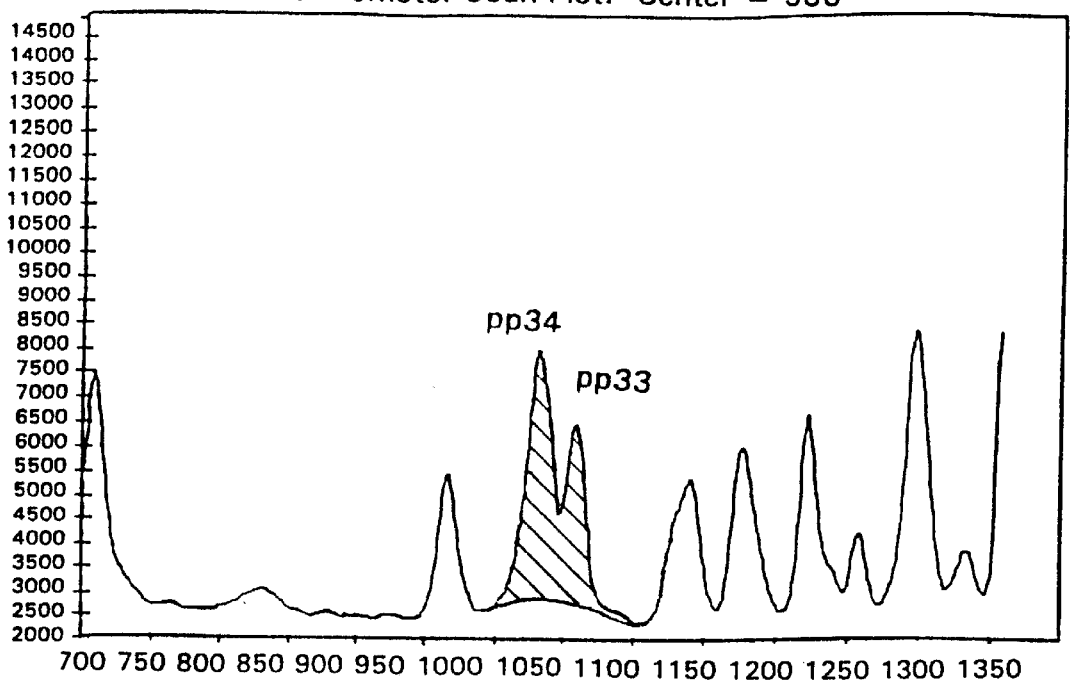
FIG. 28. Scanning densitometry of anti-phosphotyrosine immunoblots for 3T3 cells treated with 160 nM 12-O-tetra-decanoylphorbol-13-acetate (TPA) or DMS0 vehicle for 24 h in 0.5% serum media. Bolded peaks indicate p34 and p33 tyrosylphosphoproteins.
Figure 28B:
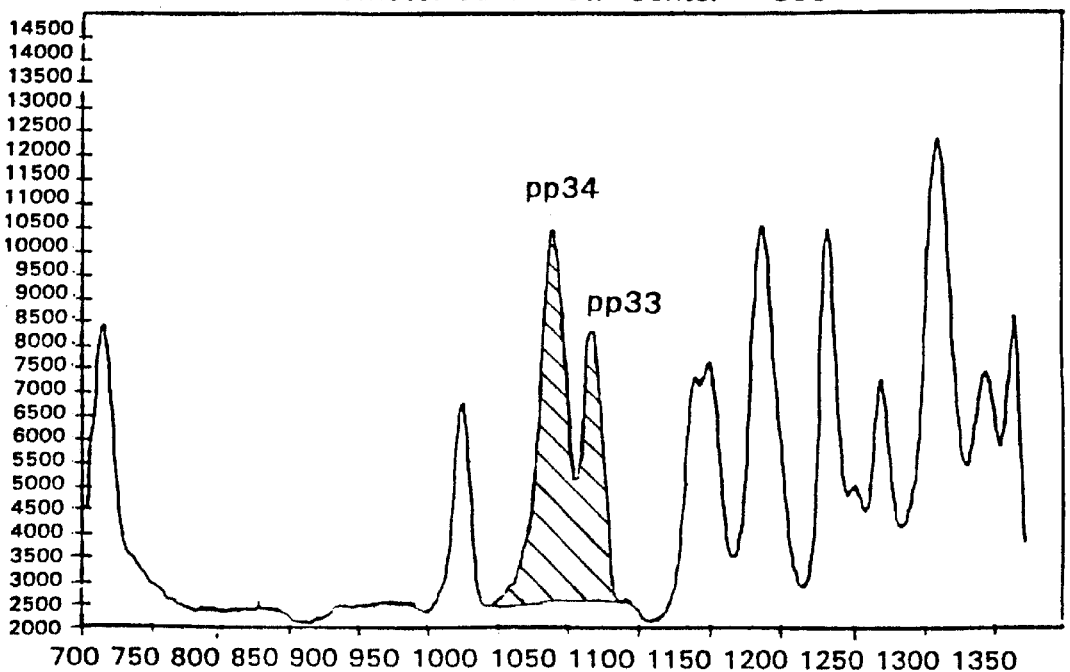
Figure 29:
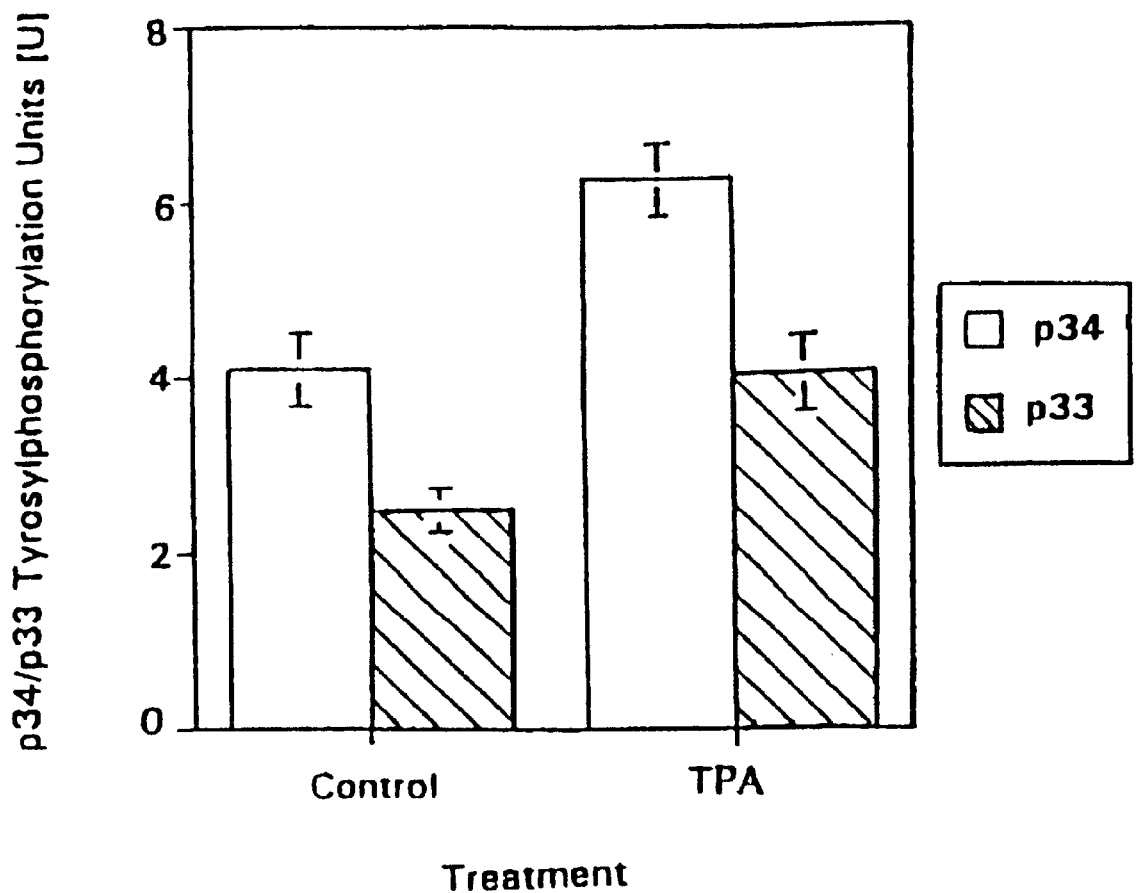
FIG. 29. Bar graph depicting the quantification of the scanning densitometry of the putative cyclin dependent kinases (p34/p33) from the anti-phosphotyrosine immunoblot. Exposure of 3T3 cells to 160 nM 12-O-tetra-decanoylphorbol-13-acetate (TPA) for 24 h results in an increase in tyrosylphosphorylation of p34 and p33 of 54 and 95%, respectively, compared to the vehicle control. Each bar on the graph represents the result of scanning an immunoblot produced from the pooled whole cell lysates of four plates per treatment. Error bars represent the 10 percent coefficient of variation in the quantification of density.

Exposure of 3T3 cells to 160 nM TPA for 24 h results in an increase in tyrosylphosphorylation of p34 and p33 of 54 and 95%, respectively, compared to the vehicle control The anti-phosphotyrosine immunoblot of 3T3 cell lysate protein separated using an 11% SDS-PAGE gel for 3T3 cells exposed to 10 nM TCDD is presented in FIG. 27. Results of scanning the control and TCDD-treated lanes are presented in FIG. 28; bolded peaks indicate p34 and p33 tyrosylphosphoproteins. In FIG. 29 the putative cyclin dependent kinases (p34/p33) are quantified from the anti-phosphotyrosine immunoblot. Results of serum supplementation (c.f. immunoblot in FIG. 27, scan results not depicted in FIG. 28) indicate enhanced tyrosylphosphorylation of p34/p33. This result would be expected if the pp34/pp33 are cyclin dependent kinases, since the serum supplemented media provide growth factor that stimulate the cells to mitosis and this stimulus is be mediated through the CDK.

EXAMPLE 8

Enhanced tyrosylphosphorylation of p34/p33 in BNL CL.2 cell lysates 24 hours following exposure to the nongenotoxic carcinogen 2,3,7,8-tetrachlorodibenzo-p-dioxin Summary It is demonstrated that exposure of BNL CL.2 cells to 0.1, 1, 10 or 100 nM 2,3,7,8-tetrachlorodibenzo-p-dioxin for 24 h in a low serum media enhances the tyrosine phosphorylation status of two cell lysate proteins, p34 and p33, compared to dimethylsulfoxide-treated controls. These results indicate that the early in vitro effects of the nongenotoxic carcinogen 2,3,7,8-tetrachlorodibenzo-p-dioxin can be quantified through a change in cellular p34/p33 tyrosylphosphorylation and therefore that stimulation of tyrosylphosphorylation of p34/p33 is specific for nongenotoxic carcinogens.

Materials and Methods
Chemicals

This section is as previously described in Example 6.

Tissue culture cells, culture conditions and dosing

BNL CL.2 cells (ATCC TIB73) are purchased from American Type Culture Collection (Bethesda, Md.). These cells are representative of normal mouse hepatocytes. All other procedures were performed as detailed in Example 6.

The following concentrations and reagents are added to the appropriate tubes (4 plates/treatment). Dimethyl sulfoxide (DMSO) is used as the diluent for TCDD.

10 mL of DMEM+20% FBS-HI+0.1% DMSO (positive control)
10 mL of DMEM+0.5% FBS-HI+0.1% DMSO
10 mL of DMEM+0.5% FBS-HI+0.1 nM TCDD
10 mL of DMEM+0.5% FBS-HI+1.0 nM TCDD
10 mL of DMEM+0.5% FBS-HI+10 nM TCDD
10 mL of DMEM+0.5% FBS-HI+100 nM TCDD All plates were returned to the incubator for 24 h at the environmental conditions listed above. After the 24 h incubation period, the cells are harvested using the harvesting procedure described.

Gel electrophoresis and immunoblotting with anti-phosphotyrosine

These procedures are carried out as described in Example 1 except that anti-phosphotyrosine antibody is used in place of anti-PSTAIR antibody.

Protein determination

This procedure is performed as described in Example 1.

Results

Figure 30:
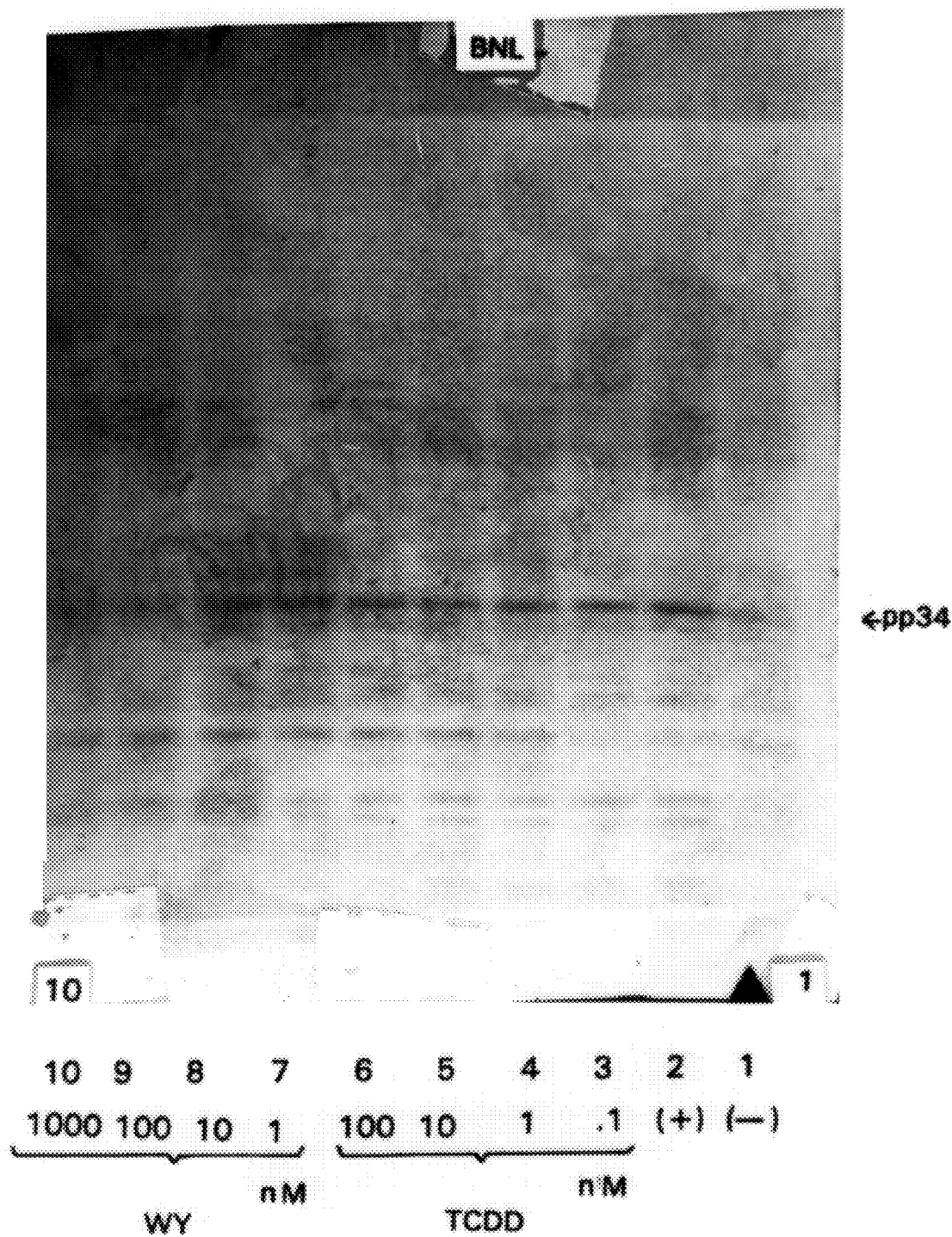
FIG. 30. Anti-phosphotyrosine immunoblots of BNL CL.2 cell lysate protein separated using 11% SDS-PAGE gels for BNL CL.2 cells exposed to 0.1, 1, 10, or 100 nM 2,3,7,8-tetrachlorodibenzo-p-dioxin (TCDD; lanes 3,4,5 and 6, respectively) or DMSO vehicle (lane 1) for 24 h in 0.5% serum supplemented media Lane 2 is the 20% serum-supplemented control.
Figure 31A:
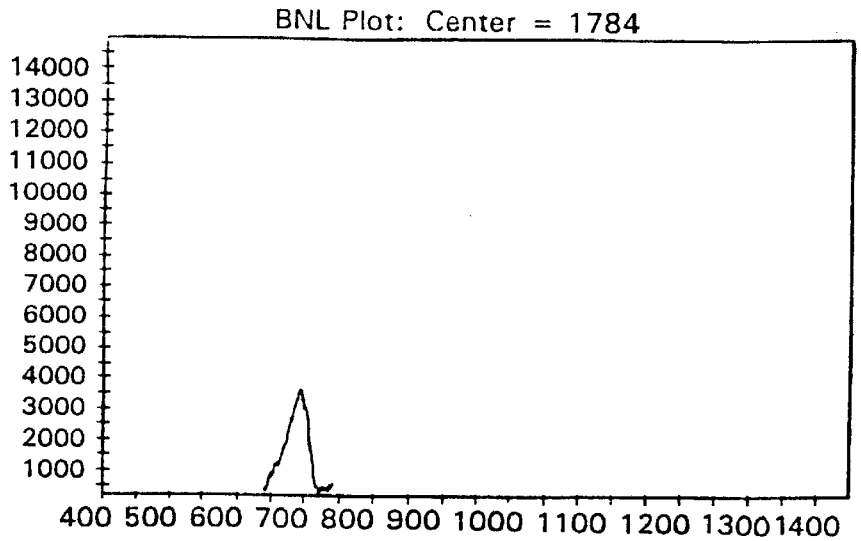
FIG. 31. Scanning densitometry of anti-phosphotyrosine immunoblots in the 35 to 30 kDa molecular weight range for BNL CL.2 cells treated with 0.1, 1, 10 or 100 nM 2,3,7,8-tetrachlorodibenzo-p-dioxin (TCDD) or DMSO vehicle (Control) for 24 h in 0.5% serum supplemented media. p34 and p33 tyrosylphosphoproteins are indicated for the respective treatments. Top row (left to right) 0.5% and 20% serum supplementation; Middle row 0.1 and 1 nM TCDD; Bottom row 10 and 100 nM TCDD.
Figure 31C:
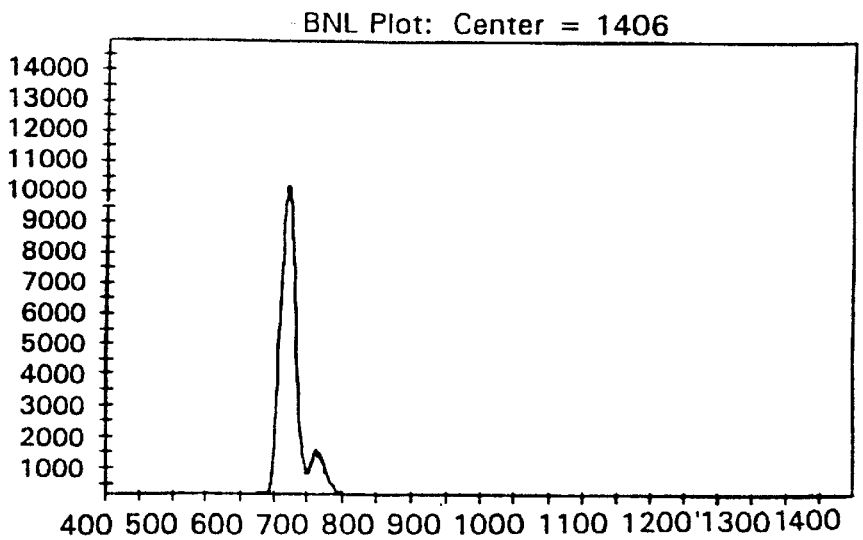
Figure 31E:
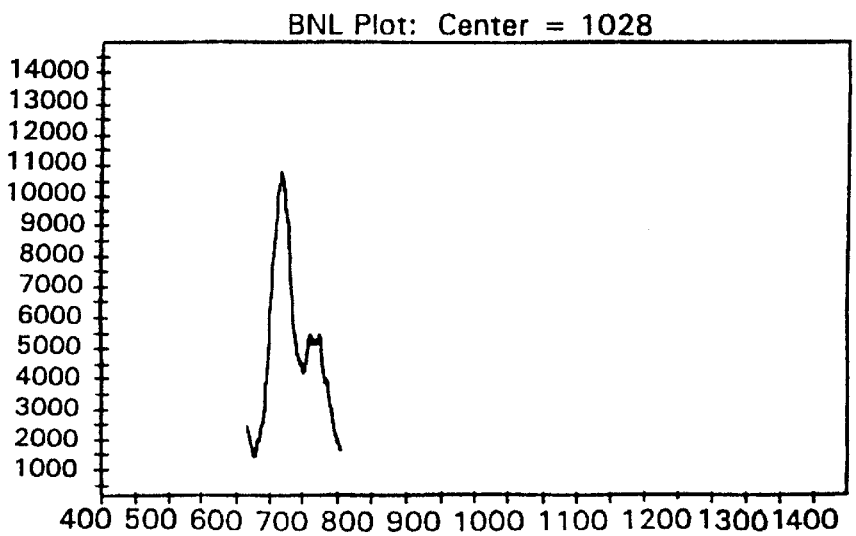
Figure 31B:
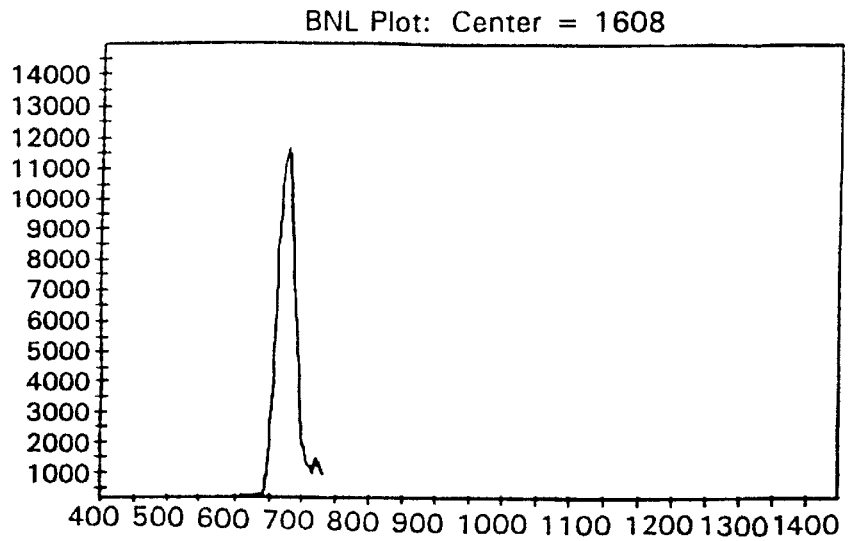
Figure 31D:
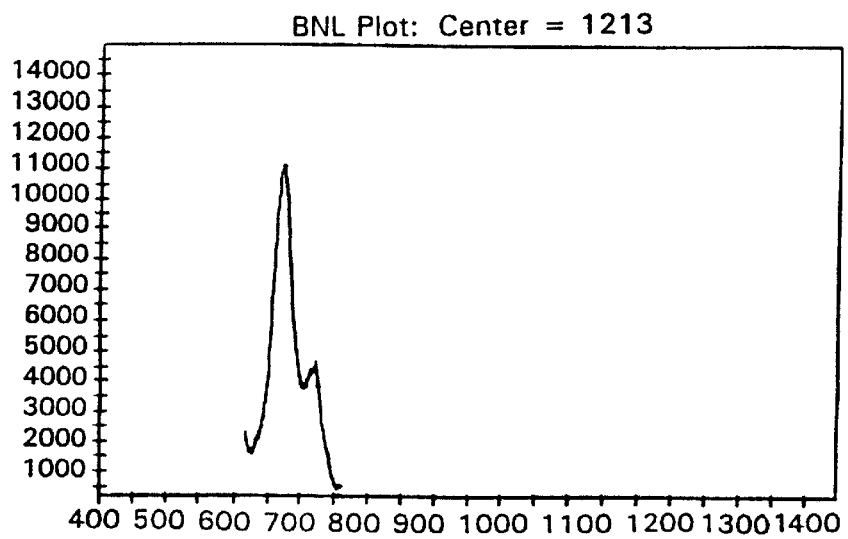
Figure 31F:
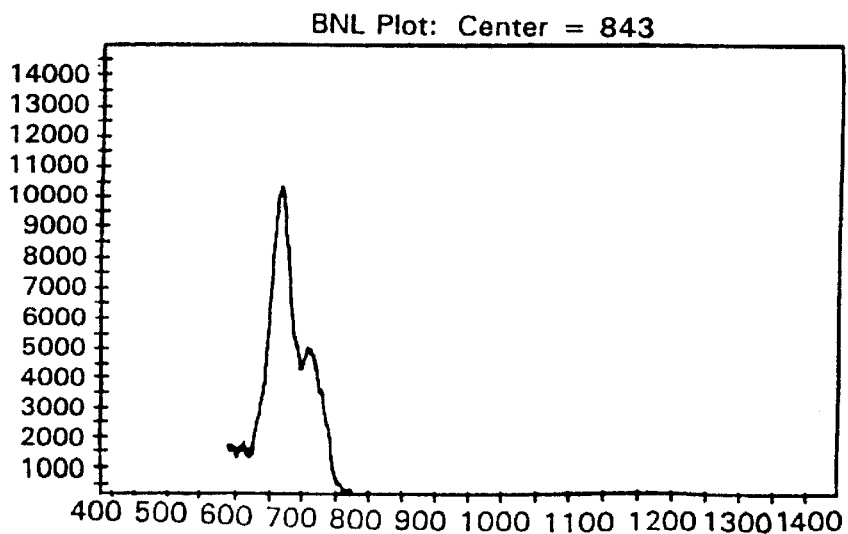
Figure 32:
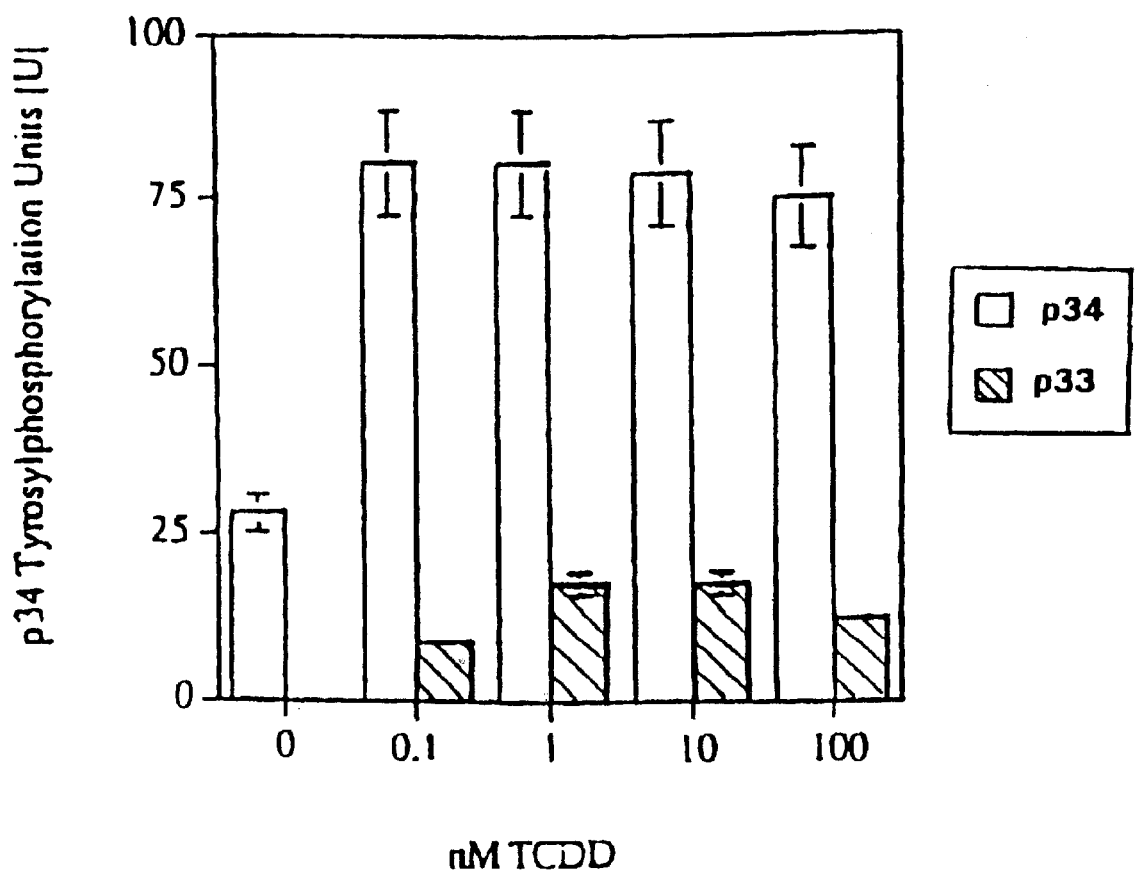
FIG. 32. Bar graphs depicting the quantification of the scanning densitometry of the putative cyclin dependent kinases (p34-top/p33-bottom) from the anti-phosphotyrosine immunoblot. Exposure of BNL CL2 cells to 0.1, 1, 10 or 100 nM 2,3,7,8-tetrachlorodibenzo-p-dioxin (TCDD) for 24 h results in a similar increase in tyrosylphosphorylation of p34, averaging 180% of the vehicle control over all concentrations of TCDD. Twenty percent serum supplementation results in an increase of tyrosylphosphorylation of p34 of 229% of the vehicle control. Vehicle controls at 0.5% serum supplementation exhibit no tyrosylphosphorylation at p33, while TCDD exposure at the four concentrations enhances tyrosylphosphorylation of this putative CDK to 0.9, 2.0, 2,0 and 1.9 density units, respectively. The increases in tyrosylphosphorylation of p33 by TCDD are 3.4 times the p33 tyrosine phosphorylation produced by 20% serum supplementation. Each bar on the graph represents the result of scanning an immunoblot produced from the pooled whole cell lysates of four plates per treatment. Error bars represent the 10 percent coefficient of variation in the quantification of density.

Exposure of BNL CL2 cells to 0.1, 1, 10 or 100 nM 2,3,7,8-tetrachlorodibenzo-p-dioxin (TCDD) for 24 h results in a similar increase in tyrosylphosphorylation of p34, averaging 180% of the vehicle control over all test concentrations of TCDD. Twenty percent serum supplementation results in an increase of tyrosylphosphorylation of p34 of 229% of the vehicle control. Vehicle controls at 0.5% serum supplementation exhibit no tyrosylphosphorylation at p33, while TCDD exposure at the four concentrations enhances tyrosylphosphorylation of this putative CDK to 0.9, 2.0, 2, 0 and 1.9 density units, respectively. The increases in tyrosylphosphorylation of p33 by TCDD are 3.4 times the p33 tyrosine phosphorylation produced by 20% serum supplementation. The anti-phosphotyrosine immunoblot of BNL CL.2 cell lysate protein separated using an 11% SDS-PAGE gel for BNL CL.2 cells exposed to the four concentrations of TCDD is presented in FIG. 30. Results of scanning the control and TCDD-treated lanes are presented in FIG. 31; the represented peaks are p34 and p33 tyrosylphosphophoproteins. In FIG. 32 the putative cyclin dependent kinases (p34/p33) are quantified from the anti-phosphotyrosine immunoblot.

EXAMPLE 9

Enhanced tyrosylphosphorylation of p34/p33 in BNL CL.2 cell lysates 24 hours following exposure to the nongenotoxic carcinogen pirnixic acid Summary It is demonstrated that exposure of BNL CL.2 cells to 1, 10 or 100 nM pirnixic acid for 24 h in a low serum media enhances the tyrosine phosphorylation status of two cell lysate proteins, p34 and p33, compared to dimethylsulfoxide-treated controls. These results indicate that the early in vitro effects of the nongenotoxic carcinogen pirnixic acid can be quantified through a change in cellular p34/p33 tyrosylphosphorylation and that stimulation of tyrosylphosphorylation of p34/p33 is specific for nongenotoxic carcinogens.

Materials and Methods

Chemicals

This section is as previously described in Example 7.

Tissue culture cells, culture conditions and dosing

BNL CL.2 cells (ATCC TIB73) are purchased from American Type Culture Collection (Bethesda, Md.). These cells are representative of normal mouse hepatocytes. All other procedures were performed as detailed in Example 7.

The following concentrations and reagents are added to the appropriate tubes (4 plates/treatment). Dimethyl sulfoxide (DMSO) is used as the diluent for TCDD.

10 mL of DMEM+20% FBS-HI+0.1% DMSO (positive control)

10 mL of DMEM+0.5% FBS-HI+0.1% DMSO 10 mL of DMEM+0.5% FBS-HI+1 nM pirnixic acid 10 mL of DMEM+0.5% FBS-HI+10 nM pirnixic acid 10 mL of DMEM+0.5% FBS-HI+100 nM pirnixic acid 10 mL of DMEM+0.5% FBS-HI+1000 nM pirnixic acid All plates were returned to the incubator for 24 h at the environmental conditions listed above. After the 24 h incubation period, the cells are harvested using the harvesting procedure described.

Gel electrophoresis and immunoblotting with anti-phosphotyrosine

These procedures are carried out as described in Example 1 except that anti-phosphotyrosine antibody is used in place of anti-PSTAIR antibody.

Protein determination

This procedure is performed as described in Example 1.

Results

Figure 33:
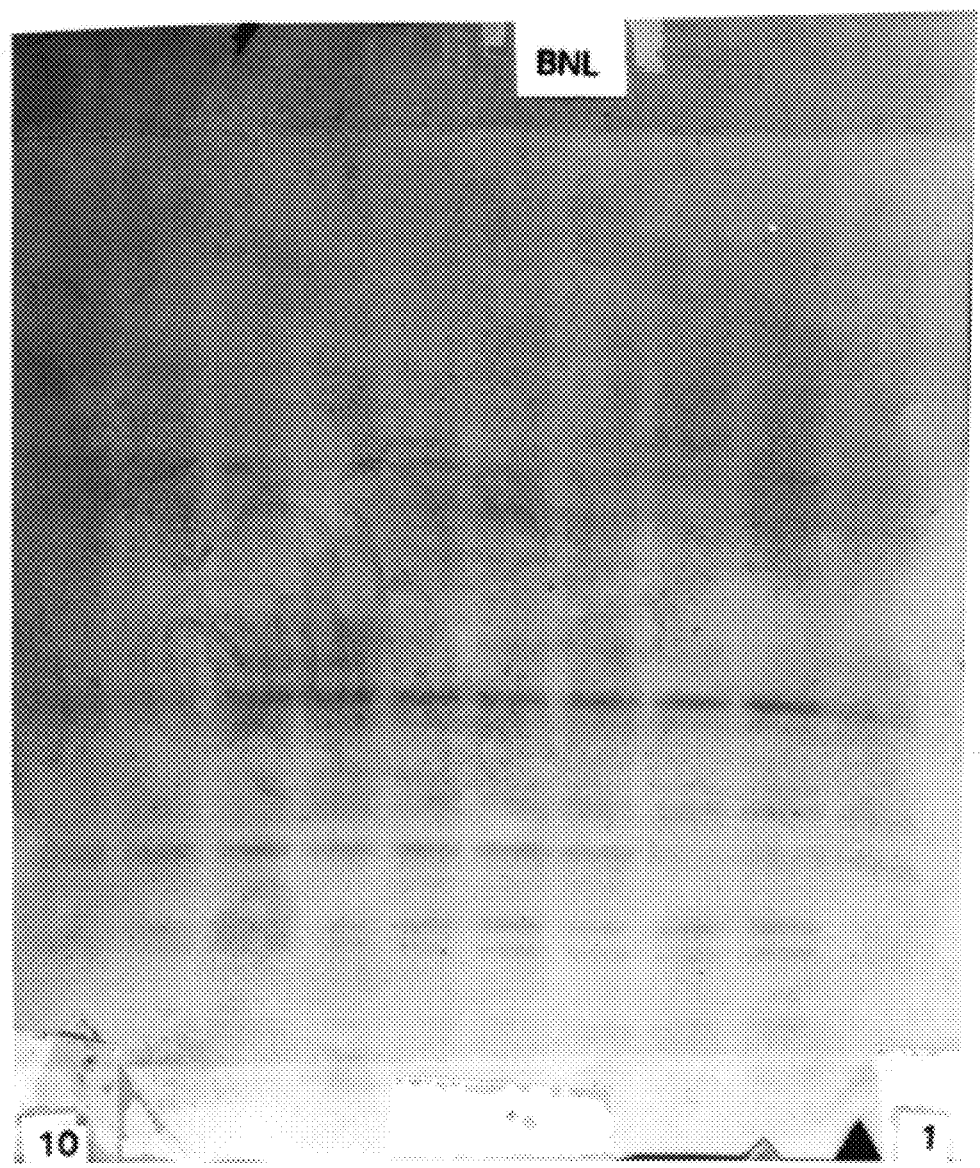
FIG. 33. Anti-phosphotyrosine immunoblots of BNL CL.2 cell lysate protein separated using 11% SDS-PAGE gels for BNL CL.2 cells exposed to 1, 10, 100, or 1000 nM pirnixic acid (lanes 7,8,9 and 10, respectively) or DMSO vehicle (lane 1) for 24 h in 0.5% serum supplemented media Lane 2 is the 20% serum-supplemented control.
Figure 34A:
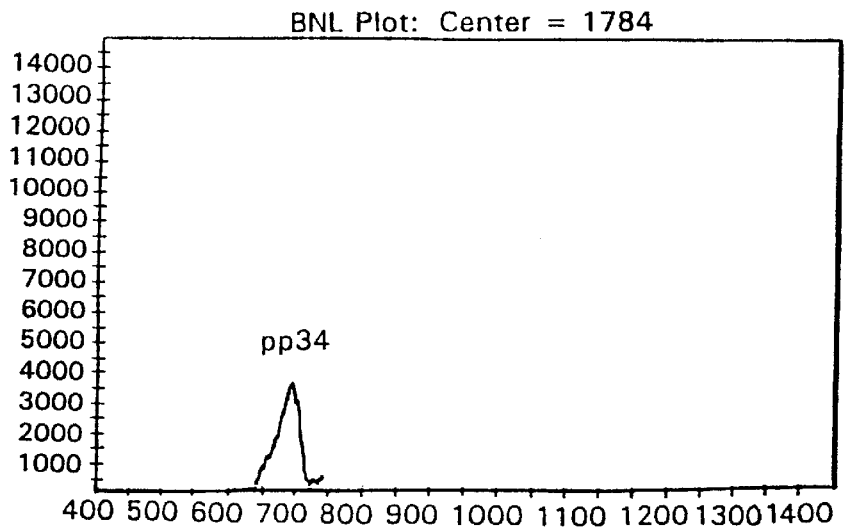
FIG. 34. Scanning densitometry of anti-phosphotyrosine immunoblots in the 35 to 30 kDa molecular weight range for BNL CL.2 cells treated with 1, 10, 100, or 1000 nM pirnixic acid or DMSO vehicle (Control) for 24 h in 0.5% serum media. p34 and p33 tyrosylphosphoproteins are indicated for the respective treatments. Top row (left to right) 0.5% serum and 20% serum; Middle row 1 and 10 nM pirnixic acid; Bottom row 100 and 1000 nM pirnixic acid.
Figure 34C:
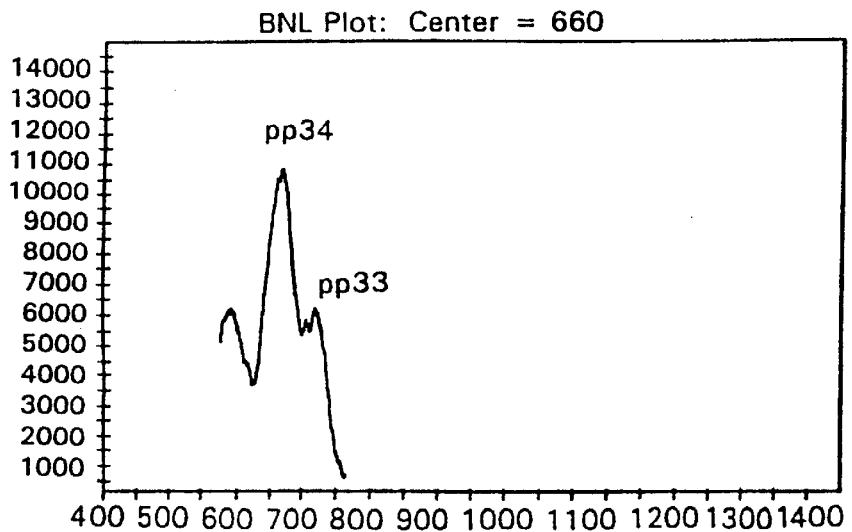
Figure 34E:
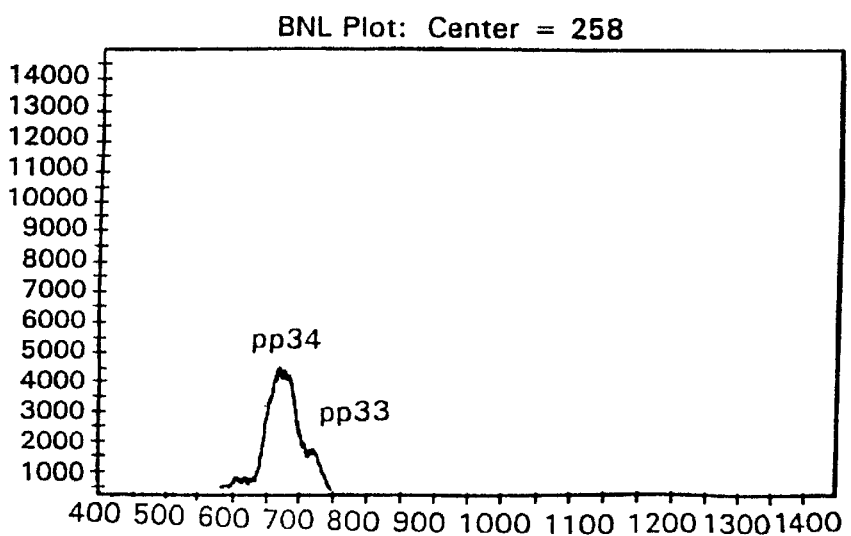
Figure 34B:
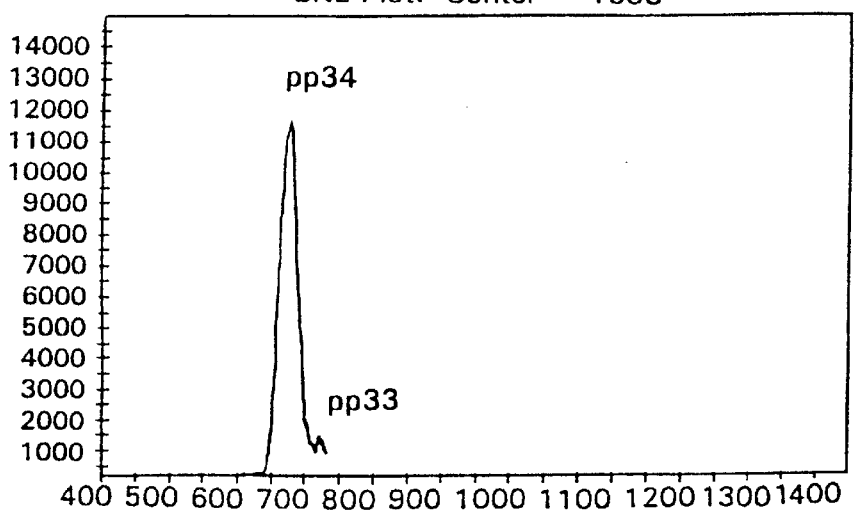
Figure 34D:
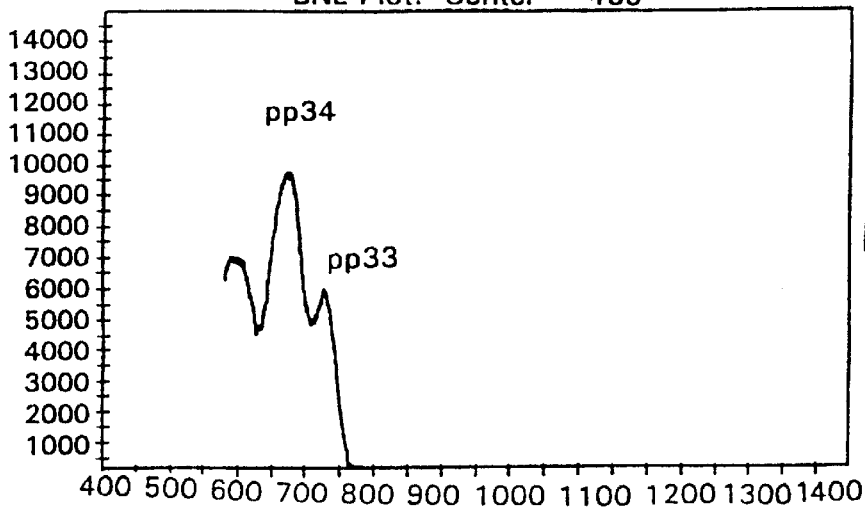
Figure 34F:
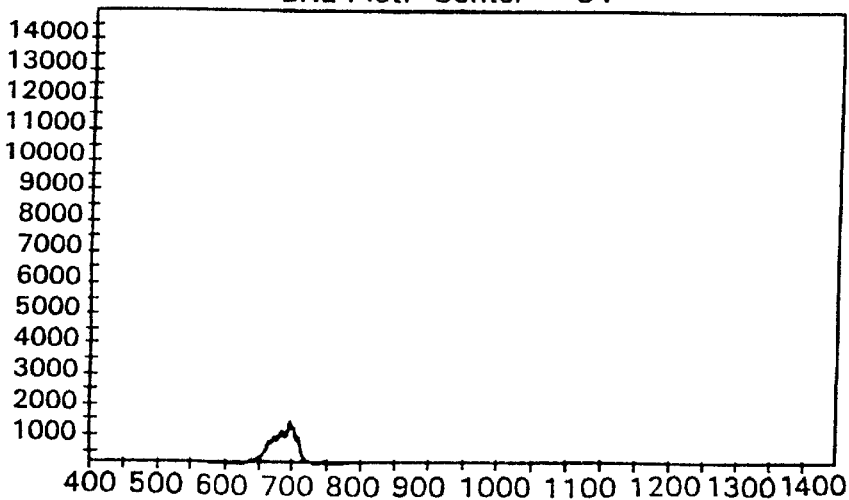
Figure 35:
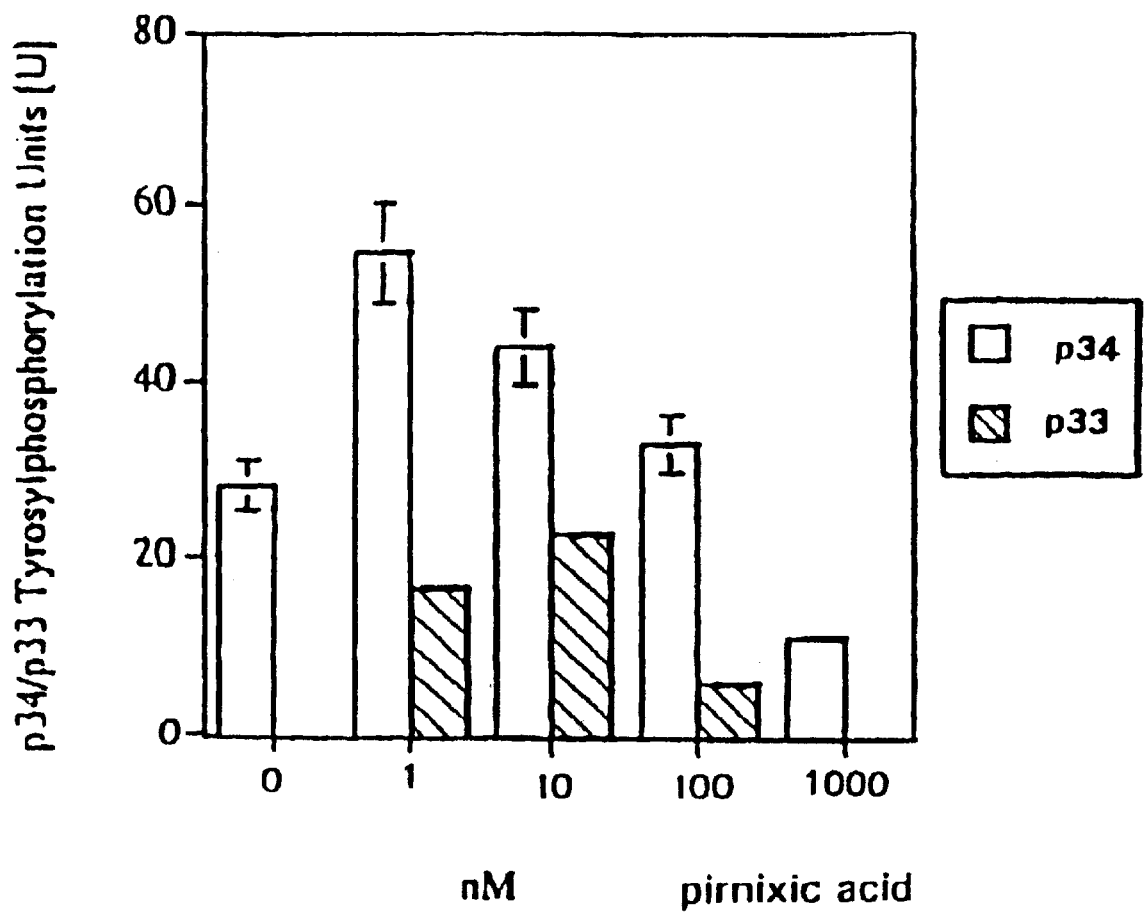
FIG. 35. Bar graphs depicting the quantification of the scanning densitometry of the putative cyclin dependent kinases (p34-top/p33-bottom) from the anti-phosphotyrosine immunoblot. Exposure of BNL CL2 cells to pirnixic acid for 24 h results in increases in tyrosylphosphorylation of p34 relative to the vehicle control for the 1 and 10 nM concentrations, 96 and 58% increases, respectively. At 100 nM pirnixic acid, the tyrosylphosphorylation of p34 is similar to the vehicle control, while at 1000 nM tyrosine phosphorylation of p34 is depressed 60% from the vehicle control. Twenty percent serum supplementation results in an increase of tyrosylphosphorylation of p34 of 229%, relative to the vehicle control. The 0.5% serum supplementation control exhibits no tyrosylphosphorylation at p33, while pirnixic acid exposure enhances tyrosylphosphorylation of this putative CDK to 2.0, 2.5 and 0.5 density units, respectively, at the 1, 10, and 100 nM concentrations. The increases in tyrosylphosphorylation of p33 by pirnixic acid at 1 and 10 nM are roughly 4 times the p33 tyrosine phosphorylation produced by 20% serum supplementation. Each bar on the graph represents the result of scanning an immunoblot produced from the pooled whole cell lysates of four plates per treatment. Error bars represent the 10 percent coefficient of variation in the quantification of density.
Figure 36A:
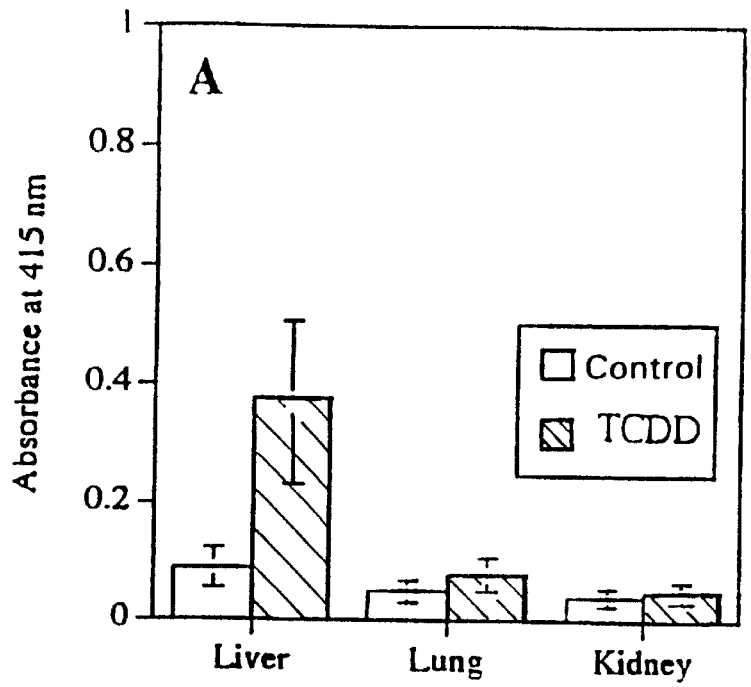
FIG. 36. Bar graph depicting the microtiter methodology for quantification of tyrosylphosphorylation of tissue CDK. The capture antibody was anti-PSTAIR and the secondary antibody was anti-phosphotyrosine. Dosing of C57BL/6J female mice daily with 0, 0.25, 0.5, 1 or 2 ng TCDD/kg-day (A, B, C and D, respectively) results in enhanced tyrosylphosphorylation of hepatic CDK but not pulmonary or renal CDK. This identifies the target tissue for the cellular proliferative effects of TCDD as the liver. Maximal increase in tyrosylphosphorylation of hepatic CDK is observed at the 0.5 ng TCDD/kg-day dose regimen. The error bars represent the 95 percent confidence interval of the mean absorbance determined at 415 nm for each of the treatments (n=10 mice per treatment).
Figure 36B:
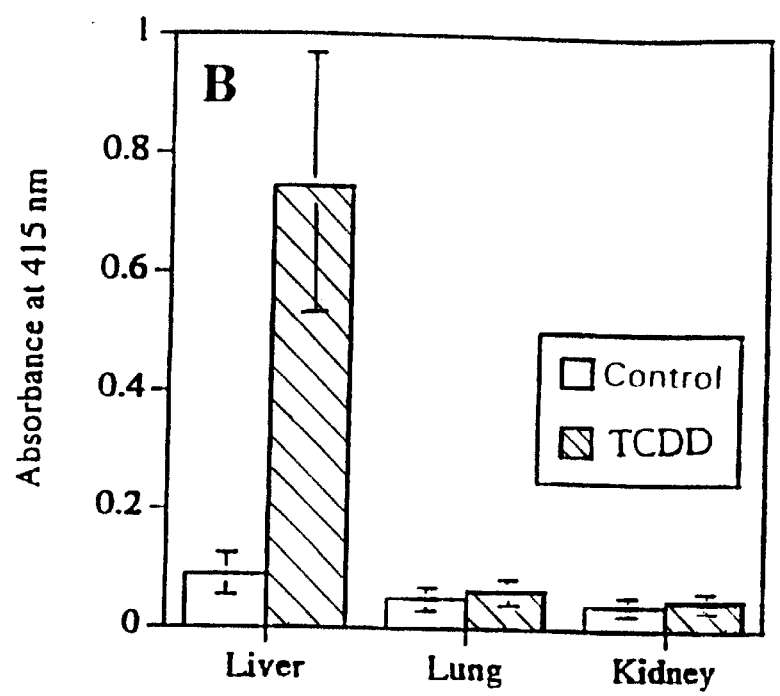
Figure 36C:
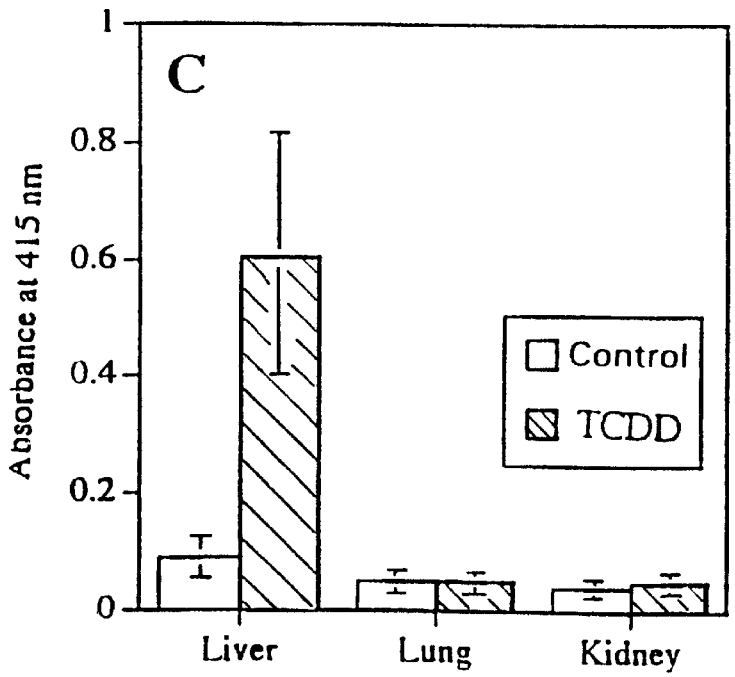
Figure 36D:
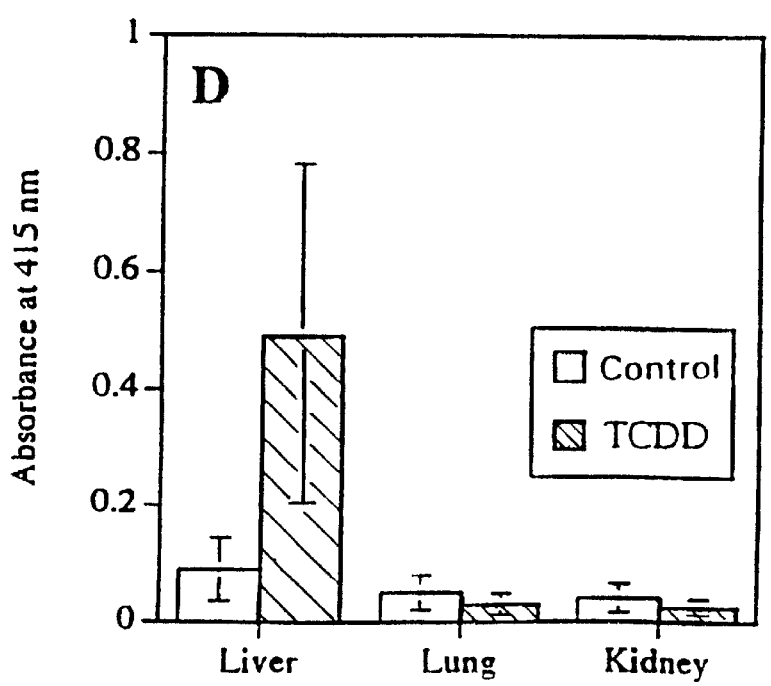
Figure 37A:
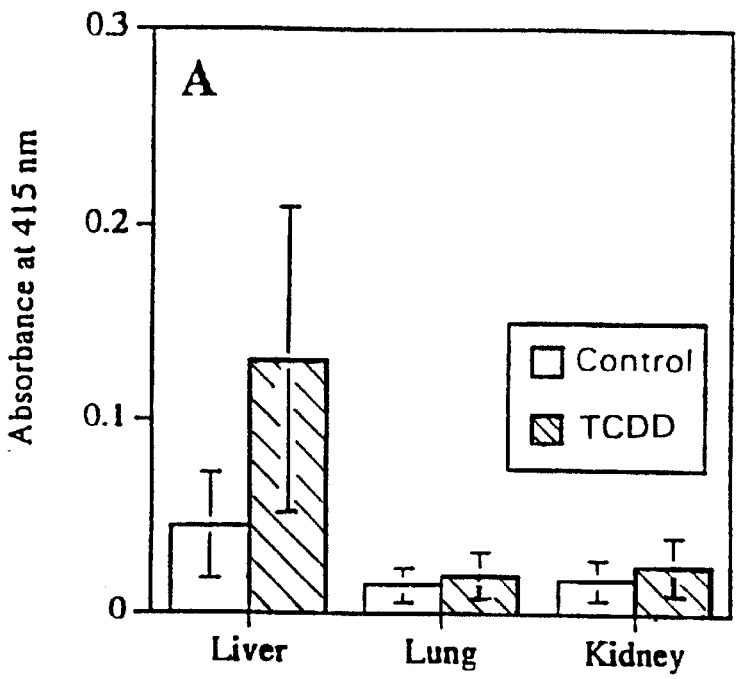
FIG. 37. Bar graph depicting the microtiter methodology for quantification of tyrosylphosphorylation of tissue $p34^{cdc2}$ kinase. The capture antibody was anti-C-terminus and the secondary antibody was anti-phosphotyrosine. Dosing of C57BL/6J female mice daily with 0, 0.25, 0.5, 1 or 2 ng TCDD/kg-day (A, B, C and D, respectively) results in enhanced tyrosylphosphorylation of hepatic $p34^{cdc2}$ kinase but not pulmonary or renal $p34^{cdc3}$ kinase. This identifies the target tissue for the cellular proliverative effects of TCDD as the liver. Maximal increase in tyrosylphosphorylation of hepatic $p34^{cdc2}$ kinase is observed at the 0.5 ng TCDD/kg-day dose regimen. The error bars represent the 95 percent confidence interval of the mean absorbance determined at 415 nm for each of the treatments (n=10 mice per treatment).
Figure 37B:
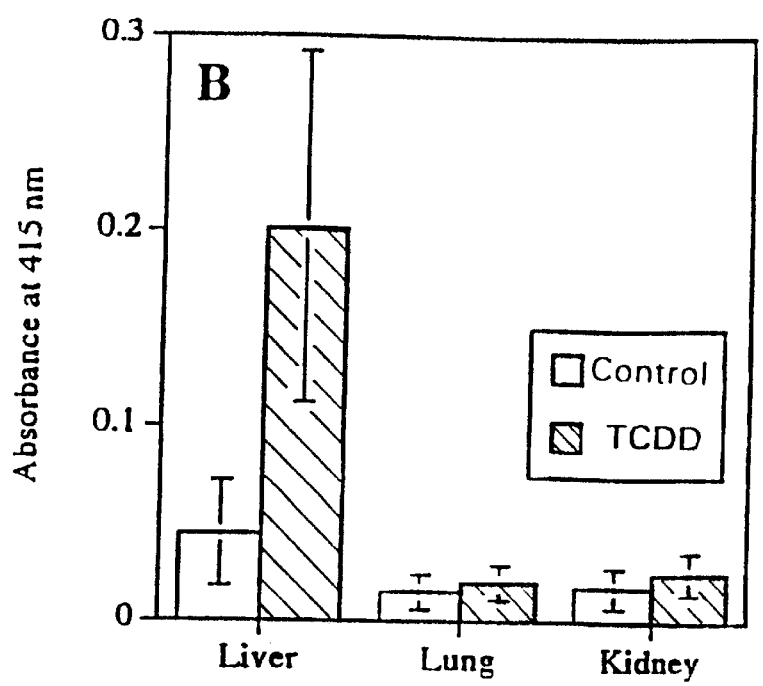
Figure 37C:
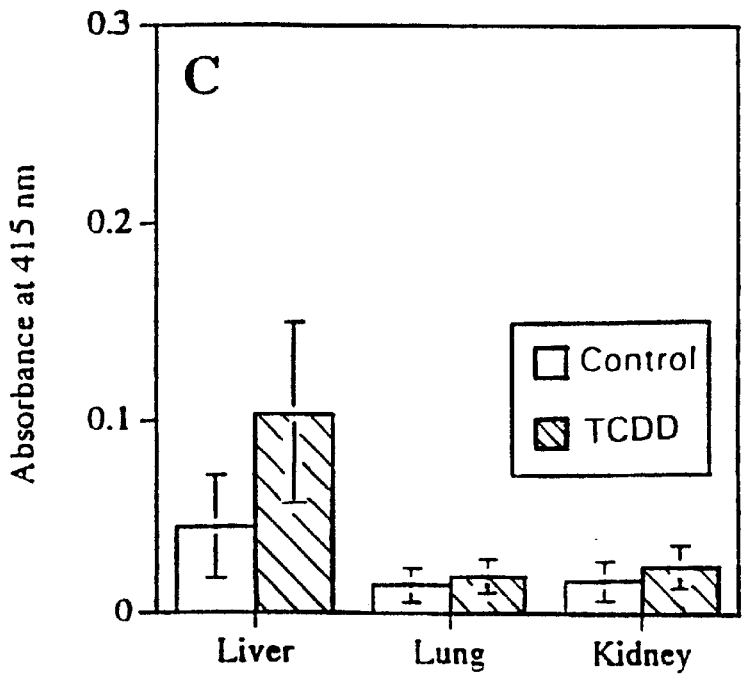
Figure 37D:
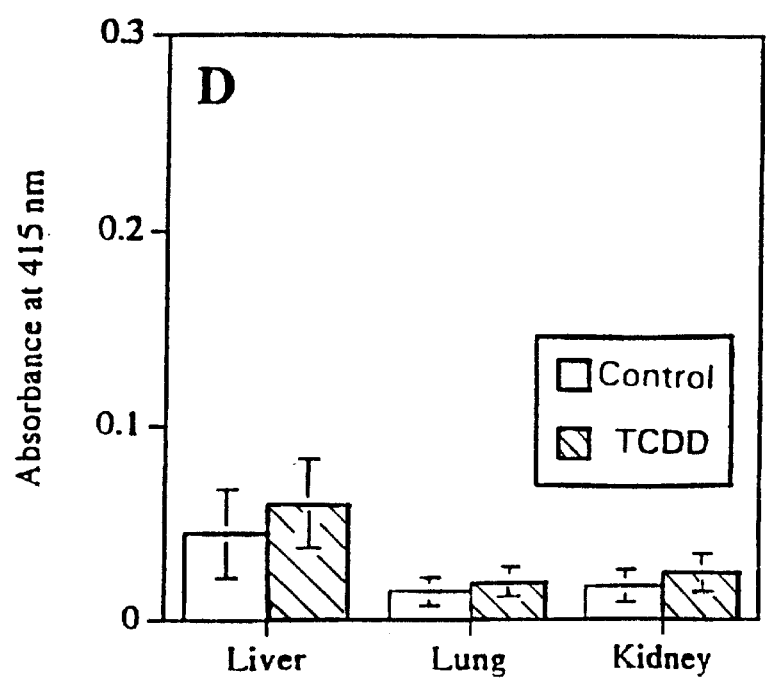

Exposure of BNL CL2 cells to pirnixic acid for 24 h results in increases in tyrosylphosphorylation of p34 relative to the vehicle control for the 1 and 10 nM concentrations, 96 and 58% increases, respectively. At 100 nM pirnixic acid the tyrosylphosphorylation of p34 is similar to the vehicle control, while at 1000 nM tyrosine phosphorylation of p34 is depressed 60% from the vehicle control. Twenty percent serum supplementation results in an increase of tyrosylphosphorylation of p34 of 229%, relative to the vehicle control. The 5% serum supplementation control exhibits no tyrosylphosphorylation at p33, while pirnixic acid exposure enhances tyrosylphosphorylation of this putative CDK to 2.0, 2.5 and 0.5 density units, respectively, at the 1, 10, and 100 nM concentrations. The increases in tyrosylphosphorylation of p33 by pirnixic acid at 1 and 10 nM are roughly 4 times the p33 tyrosine phosphorylation produced by 20% serum supplementation The anti-phosphotyrosine immunoblot of BNL CL.2 cell lysate protein separated using an 11% SDS-PAGE gel for BNL CL.2 cells exposed to the four concentrations of pirnixic acid is presented in FIG. 33. Results of scanning the control and TCDD-treated lanes are presented in FIG. 34; the represented peaks are p34 and p33 tyrosylphosphosphoproteins. In FIG. 35 the putative cyclin dependent kinases (p34/p33) are quantified from the anti-phosphotyrosine immunoblot.

EXAMPLE 10

Use of a microtiter assay for the assessment of enhanced tyrosylphosphorylation of cyclin-dependent kinases (CDK) or p34$^{cdc2}$ kinase in hepatic, pulmonary and renal cytosol (S-9) preparations from C57BL/6J female mice administered 2,3,7,8-tetrachlorodibenzo-p-dioxin for 90 days Summary The regulation of the tyroslyphosphorylaltion status of the cytosolic cyclin dependent kinases (CDK) is considered the control mechanism for the entry into $G_1$ from $G_0$, the START signal, and also for the movement of the cell from $G_2$ to M, the initiation of mitosis. A microtiter kit is described that allows for the demonstration of enhanced tyrosylphosphorylation of hepatic CDK as well as p34$^{cdc2}$ kinase kinase following the daily administration of 0.25, 0.5, 1 or 2 ng 2,3,7,8-tetrachlorodibenzo-p-dioxin (TCDD)/kg to young, female mice for 90 days. It is also demonstrated that the microtiter kit may be used to assay for enhanced tyrosylphosphorylation of CDK in extrahepatic tissues and thus allow for the identification of the most sensitive responding tissue.

Materials and Methods

Materials and Chemicals:

Immobilon 2 microtiter plates Dynatech (Shantifly, Va.)

Anti-PSTAR polyclonal antibody UBI (Lake Placid, N.Y.)

Anti-C-termrninus polyclonal antibody UBI (Lake Placid, N.Y.)

Anti-phosphotyrosine monolocral antibody UBI (Lake Placid, N.Y.)

Peroxidase-labeled rabbit anti-primary antibody BioRad (Melville, N.Y.)

BSA (bovine serum albumin) [Sigma #A-3350]

Triton X-100 [Sigma #X-100]

EGTA (ethylene glycol-bis(β-aminoethylether)N,N,N',N'-tetaacetic acid) [Sigma #E-4378]

PMSF (phenylmethylsulifonyl fluoride) [Sigma #P-7626]

Leupeptin [Sigma #L-2984]

Soy bean trypsin inhibitor [Sigma #T-9003]

N-Tosyl-L-phenylalanine chloromethyl ketone [Sigma #T-4376]

Sodium fluoride [Sigma #S-6521]

β-Glycerophosphate [Sigma #G-6626]

Paranitrophenyl phosphate [Sigma #104-0]

Sodium orthovanadate [Sigma #S-6508]

DTT (dithiothreitol) [Sigma #D-0632]

$MgCl_2$

ABTS (2,2'-Azino-bis(3-ethylbenzhazoline-6-sulfonicacid) diammonium salt) [Sigma #A-1888]

$H_2O_2$ (hydrogen peroxide) [Sigma #H-1009]

TRIS [Sigma (St. Louis, Mo.)]

Na Carbonate [Sigma (St. Louis, Mo.)]

2,3,7,8-tetrachlorodibenzo-p-dioxin [AccuStandard, Inc. (New Haven, Conn.)]

Reagents:

A. Sodium carbonate buffer; 0.1M, pH 9.6
  a) Mix 71.3 ml of 1M $NaHCO_3$ and 28 ml of 1M $Na_2CO_3$.
  b) Add 800 m dd$H_2O$.
  c) Adjust pH to 9.6 and Qs to 1 l.

B. 10X Phosphate buffered saline; 0.15M, pH 7.2
  a) NaCl, 80.0 g/l.
  b) KCl, 2.0 g/l.
  c) $NA_2HPO_4$, 11.5 g/l.
  d) $NaH_2PO_4$, 2.0 g/l.

C. Blocking buffer; PBS with 3% BSA
  a) 1×PBS with 3 g BSA per 100 ml.

D. Washing buffer; PBS with 0.2% Triton X-100
  a) 1×PBS with 0.2 ml of Triton X-100 per ml.

E. Prep Buffer; 25 mM Tris-HCl, pH 8.0 with 10 mM $MgCl_2$, 15 mM EGTA, 0.1% Triton X-100, 0.1 mM PMSF, 0.1 mM Na fluoride, 60 mM β-glycerophosphate, 15 mM paranitrophenylphosphate, 0.1 mM Na orthovanidate, 1 μg/ml leupeptin, 10 μg/ml soybean trypsin inhibitor, 1 μg/ml aprotinin, and 10 μg/ml tosyl phenylalanine F. Assay buffer; 50 mM Tris-HCl, pH 7.4 with 10 mM MgCl$_2$, 1 mM DTT, and all inhibitors of phosphatases and proteases contained in Prep buffer G. Citrate buffer
   a) Add 9.6 g Citric acid (MW 192.12) to 950 ml ddH$_2$O.
   b) Adjust pH to 4.0 with 5M NaOH and store at 4° C.

H. ABTS stock solution
   a) 0.5487 g ABTS to 25 ml with double distilled H$_2$O and store at 4° C.

I. ABTS substrate; 0.4 mM ABTS
   a) 0.05 ml ABTS
   b) 0.02 ml diluted H$_2$O$_2$ (0.5M)
   c) 5.0 ml citrate buffer Animals and dosing Four to six-wk old, female C57BL/6J mice are obtained from Harton Sprague Dawley (Indianapolis, Ind.). The mice are fed Prolab RMH 1000 (Agway, Cortland, N.Y.) and receive tap water ad libitum. All mice are housed three per cage and maintained on a photoperiod of 12 h. Mice are administered TCDD in corn oil at 0, 0.25, 0.5, 1, or 2 ng/kg by oral gavage daily for a period of 90 days. Ten mice are treated at each dose and the volume of the dose is approximately 0.1 mL per mouse.

Procedure

Plate preparation 1. 100 μl of anti-PSTAIR or anti-C-terminus antibody at a concentration of 10 μg/mL in of 0.1M Na carbonate buffer pH 9.6 is added to the wells of a microtiter plate and incubated overnight at 4° C. These are the capture antibodies and will retain all CDK or p34$^{cdc2}$ kinase, respectively.

2. Wash plates 3× with washing buffer by filling the wells, allowing them to sit for two minutes, and inverting and shaking them. This step removes all.

3. Block plates for two hours at room temp by filling the wells with blocking buffer. The plates can be washed 1× with washing buffer and stored for several weeks at 4° C.

4. Wash fresh plated 3× or stored plates 2× with washing buffer prior to use.

Sample preparation

All preparation procedures are performed on individual or pooled hepatic, pulmonary or renal samples. Preparation and −80° C. storage of tissue S-9 fractions is performed exactly as previously described in the scientific literature (32). This procedure involves killing the mouse by cervical dislocation, removing the liver, lung or kidney sample and homogenizing the tissue in three volumes of Prep buffer. This tissue homogenate is centrifuged at 9,000×g for 20 min at 4° C. The resulting supernatant fraction, termed the S-9, is decanted into 1.5 mL plastic, conical tubes, frozen in a dry ice/ethanol bath and stored at −80° C. until the microtiter assay can be performed.

Assay 1. 200 μg of sample tissue protein is diluted in Prep buffer and mixed 1:1 with blocking buffer.

2. This is added to the wells of a prepared plate and incubated for 5 hr at 4° C. with slow constant shaking.

3. Plates are washed 3× with washing buffer and 1× with assay buffer.

4. 200 μl of primary (anti-phosphotyrosine) antibody at a dilution of 1:1000 in blocking buffer is added to each well and incubated for 2 hr at 4° C.

5. Plates are washed 3× with washing buffer.

6. 200 μl of peroxidase-conjugated (anti-mouse) secondary antibody at a dilution of 1:3000 in blocking buffer is added to each well and incubated for 1 hr at 4° C.

7. Wash plates 3× with washing buffer.

8. Add 200 μl of ABTS solution and read once a minute for 10 min in kinetics mode (Biotek EL312) at 415 nm.

Intepretation of results

Microtiter assay—The anti-PSTAIR or anti-C-terminus antibody will, respectively, capture all CDK or p34$^{cdc2}$ kinase present in the tissue S-9 fraction in the microtiter well. The anti-phosphotyrosine antibody quantifies the extent of tyrosylphosphorylation of the total CDK or p34cdc2 kinase. This quantification represents the extent to which the cells from the sampled tissue have been signaled to exit the Go stage of the cell cycle (index of proliferative signaling) by exposure to the test chemical. The current state of knowledge in the role of the cyclin dependent kinases in controlling the cell cycle (43–48) does not allow for an absolute determination as to the extent of CDK tyrosylphosphorylation relating to the strength of the proliferative signal. The fact that molecules other than peptide-like growth factors have the ability to enhance the tyrosylphosphorylation status of the CDK has not been reported in the literature. Therefore, interpretation of the capacity of a test chemical to direct the cell toward mitosis relies on a comparison to a control group treated only with the vehicle. A test chemical is considered positive for the capacity to function as a nongenotoxic carcinogen when the extent of CDK or p34$^{cdc2}$ kinase tyrosylphophorylation is statistically greater (p<0.05) than a concurrent control.

Results

Microtiter assay—As seen in FIG. 36, the dosing of C57BL/6J female mice with 0, 0.25. 0.5, 1 or 2 ng TCDD/kg-day (A, B, C and D, respectively) for 90 days results in enhanced tyrosylphosphorylation of hepatic CDK but not pulmonary or renal CDK. This identifies the target tissue for the cellular proliferative effects of TCDD as the liver. Maximal increase in tyrosylphoshorylation of hepatic CDK is observed at the 0.5 ng TCDD/kg-day dose regimen. Results for the tryosylphosphorylation of p34$^{cdc2}$ kinase are similar (FIG. 37), although the absolute increase observed is lower. This is due to the fact that p34cdc2 kinase represents only one of several possible CDK in the cytosol that function to regulate cell replecation.

EXAMPLE 11

Use of a microtiter assay for the assessment of enhanced expression of cyclin-dependent kinases (CDK) or p34$^{cdc2}$ kinase in hepatic cytosol (S-9) preparations from young male rats 1, 2, or 3 days following the administration of the nongenotoxic carcinogen pirinixic acid (WY14,643)

Summary

This example demonstrates of the utility of the assay for the quantification of CDK response elicited by a test chemical in vivo following an exposure period of any length and a description of a kit to perform the assay.

It is observed that the administration of the nongenotoxic carcinogen pirinixic acid to young, male rats results in the enhanced expression of total cytosolic cyclin-dependent kinases (CDK). A microtiter kit is described that allows for the demonstration of enhanced expression of hepatic CDK as well as p34$^{cdc2}$ kinase following a single dose of 50 mg pirinixic acid.

Materials and Methods

Materials and Chemicals

Immobilon 2 microtiter plates Dynatech (Shantilly, Va.)

Anti-C-terminus cdc2 polyclonal antibody UBI (Lake Placid, N.Y.)

Anti-PSTAIR UBI (Lake Placid, N.Y.)
Peroxidase-labeled rabbit anti-primary antibody BioRad (Melville, N.Y.)
BSA (bovine serum albumin) [Sigma #A-3350]
Triton X-100 [Sigma #X-100]
EGTA (ethylene glycol-bis($\beta$-aminoethyl ether)N,N,N',N'-tetraacetic acid)[Sigma #E-4378]
PMSF (phenylmethylsulfonyl fluoride) [Sigma #P-7626]
Leupeptin [Sigma #L-2884]
Soy bean trypsin inhibitor [sigma #T-9003]
N-Tosyl-L-phenylalanine chloromethyl ketone [Sigma #T-4376]
Sodium fluoride [Sigma #S-6521]
$\beta$-Glycerophosphate [Sigma #G-6626]
Paranitrophenyl phosphate [Sigma #104-0]
Sodium orthovanadate [Sigma #S-6508]
DTT (dithiothreitol) [Sigma #D-0632]
$MgCl_2$
ABTS (2,2'-Azino-bis(3-ethylbenzhiazoline-6-sulfonic acid) dianonium salt) [Sigma #A-1888]
$H_2O_2$ (hydrogen peroxide) [Sigma #H-1009]
TRIS [Sigma (St. Louis, Mo.)]
Na Carbonate [Sigma (St. Louis, Mo.)]
Pirinixic acid [ChemSynLabs (Lenexa, Ky.)]
Reagents
A. Sodimm carbonate buffer; 0.1M, pH 9.6
  a) Mix 71.3 ml of 1M $NaHCO_3$ and 28 ml of 1M $Na_2CO_3$.
  b) Add 800 ml $ddH_2O$.
  c) Adjust pH to 9.6 and Qs to 1 l.
B. 10×Phosphate buffered salle; 0.15M, pH 7.2
  a) NaCl, 80.0 g/l.
  b) KCl, 2.0 g/l.
  c) $Na_2HPO_4$, 11.5 g/l.
  d) $NaH_2PO_4$, 2.0 g/l.
C. Blocking buffer; PBS with 3% BSA
  a) 1×PBS with 3 g BSA per 100 ml.
D. Washing buffer; PBS with 0.2% Triton X-100
  a) 1×PBS with 0.2 ml of Triton X-100 per ml.
E. Prep Buffer, 25 mM Tris-HCl, pH 8.0 with 10 mM $MgCl_2$, 15 mM EGTA, 0.1% Triton X-100, 0.1 mM PMSF, 0.1 mM Na fluoride, 60 mM $\beta$-glycerophosphate, 15 mM paranitrophenylphosphate, 0.1 mM Na orthovanidate, 1 $\mu$g/ml leupeptin, 10 $\mu$g/ml soybean trypsin inhibitor, 1 $\mu$g/ml aprotinin, and 10 $\mu$g/ml tosyl pherylalaine
F. Assay buffer; 50 mM Tris-HCl, pH 7.4 with 10 mM $MgCl_2$, 1 mM DTT, and all inhibitors of phosphatases and proteases contained in Prep buffer
G. Citrate buffer
  a) Add 9.6 g Citric acid (MW 192.12) to 950 ml $ddH_2O$.
  b) Adjust pH to 4.0 with 5M NaOH and store at 4° C.
H. ARTS stock solution
  a) 0.5487 g ABTS to 25 ml with double distilled $H_2O$ and store at 4° C.
I. ABTS substrate; 0.4 mM ABTS
  a) 0.05 ml ABTS
  b) 0.02 ml diluted $H_2O_2$ (0.5M)
  c) 5.0 ml citrate buffer
Animals, dosing and preparation of tissue S9
This procedure is performed as described in Example 2 except only a single 50 mg/kg dose of pirinixic acid is administered. Livers are removed from rats on postdosing days 1, 2 and 3.

Figure 38:
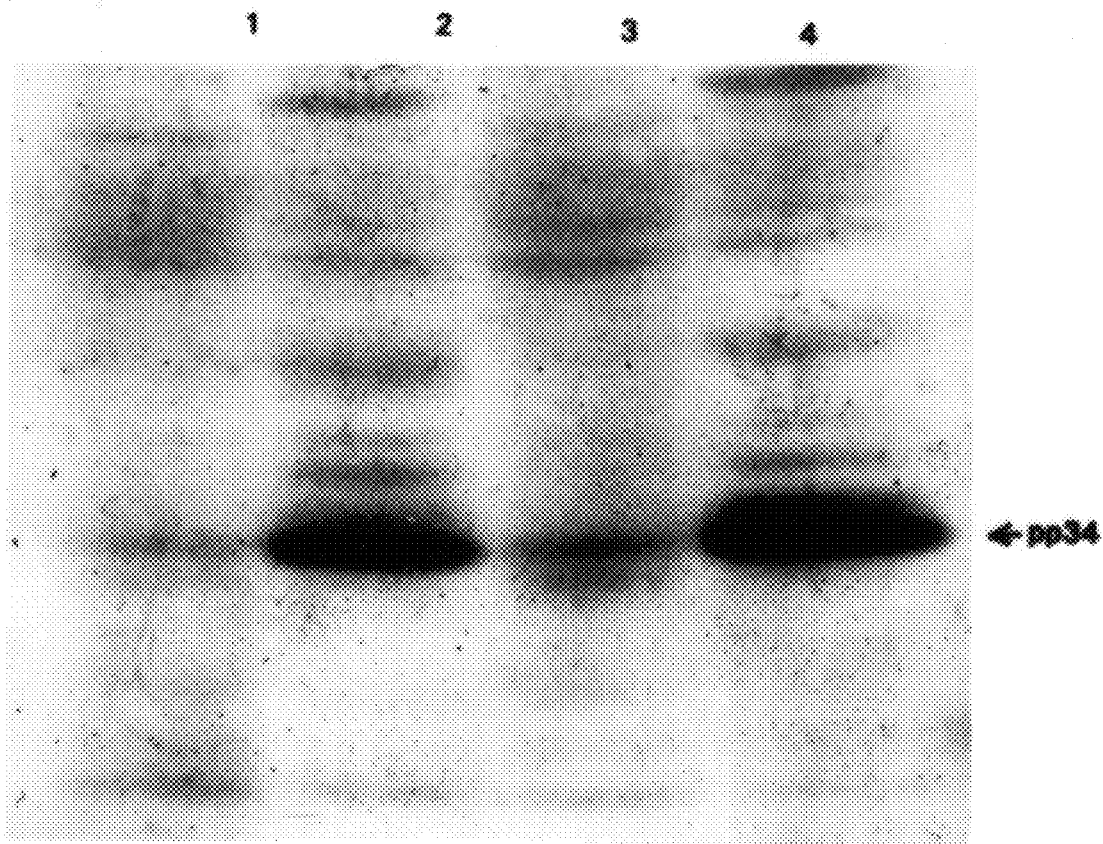
FIG. 38. The anti-cdc2 C-terminus immunoblot of rat hepatic S9 proteins separated using 10 to 11% SDS-PAGE gels for control (lanes 1 and 3) and WY 14,643-treated rats (lanes 2 and 4). A single intensely-stained band was visible in the CDK region (32 to 35 kDa) in hepatic S9 samples obtained from rats three days after receiving a single does of 50 mg WY 14,643/kg. This band is barely visible in hepatic S9 from control rats.

Gel electrophoresis and immunoblotting with anti-cdc2 C-terminus
These procedures are carried out as described in Example 1 except that anti-cdc2 C-terminus is used in place of anti-PSTAIR antibody.
Protein determination
This procedure is performed as described in Example 1.
Microtiter assay procedure
Sample preparation
All preparation procedures are performed on individual or pooled hepatic (tissue) samples. Preparation and −80° C. storage of tissue S9 fractions is performed exactly as previously described in the scientific literature (32). This procedure involves killing the rat by cervical dislocation, removing and homogenizing the tissue in three volumes of Prep buffer. This tissue homogenate is centrifuged at 9,000×g for 20 min at 4° C. The resulting supernatant fraction, termed the S9, is decanted into 1.5 ml plastic, conical tubes, frozen in a dry ice/ethanol bath and stored at −80° C. until the microtiter assay can be performed.
Assay
  1. 50 $\mu$g of S9 tissue protein is diluted in Prep buffer and mixed 1:1 with blocking buffer.
  2. This is added to the wells of a prepared plate and incubated for 5 hr at 4° C. with slow constant shaking.
  3. Plates are washed 3× with washing buffer and 1× with assay buffer.
  4. 200 $\mu$l of primary (anti-cdc2 C-terminus) antibody at a dilution of 1:1000 in blocking buffer is added to each well and incubated for 2 hr at 4° C.
  5. Plates are washed 3× with washing buffer.
  6. 200 $\mu$l of peroxidase-conjugated (anti-mouse) secondary antibody at a dilution of 1:3000 in blocking buffer is added to each well and incubated for 1 hr at 4° C.
  7. Wash plates 3× with washing buffer.
  8. Add 200 $\mu$l of ABTS solution and read once a minute for 10 min in kinetics mode (Biotek EL312) at 415 nm.
Interpretation of results
Microtiter assay—Due to cross-reactivity with other, unidentified CDK, the anti-cdc2 C-terminus antibody will quantify the total CDK expression in the tissue. This quantification represents the extent to which the cells from the sampled tissue have been signaled to exit the $G_o$ stage of the cell cycle (index of proliferative signaling) by exposure to the test chemical. The current state of knowledge in the role of the cyclin dependent kinases in controlling the cell cycle (43–48) does not allow for an explanation as to the strength of the proliferative signal. The fact that molecules other than peptide-like growth factors have the ability to enhance the expression of the CDK has not been reported in the literature. Therefore, interpretation of the capacity of a test chemical to direct the cell toward replication relies on a comparison to a concurrent control group treated only with the vehicle used to administer the test chemical. A test chemical is considered positive for the capacity to function as a nongenotoxic carcinogen when the extent of CDK or p34$^{cdc2}$ kinase expression is statistically greater (p<0.05) than a concurrent control.
Results
Immunoblotting with anti-cdc2 C-terminus—FIG. 38 depicts the immunoblot of rat hepatic S9 protein separated using 10 to 11% SDS-PAGE gels for control (lanes 1 and 3) and WY14,643-treated rats (lanes 2 and 4). A single intensely-stained band was visible in the CDK region (32 to 35 kDa) in hepatic S9 samples obtained from rats 3 days after receiving a single dose of 50 mg WY14,643/kg.

Figure 39:
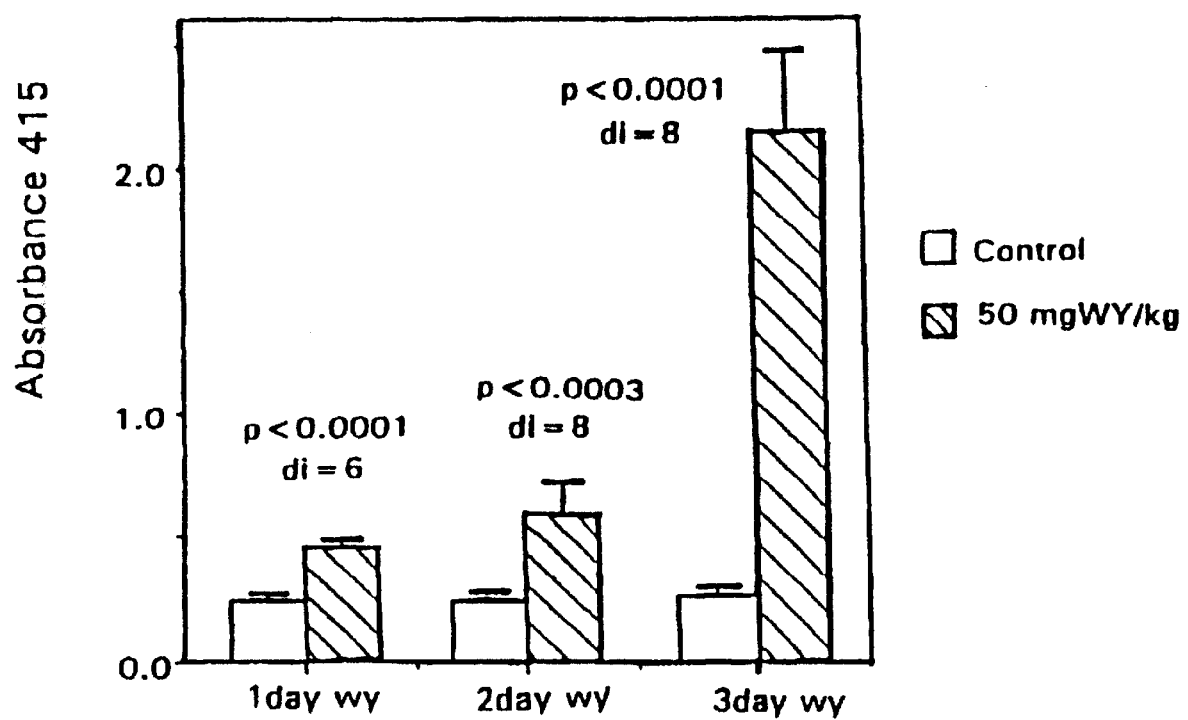
FIG. 39. Bar graph depicting the microtiter methodology for quantification of CDK expression in rat liver S9. The treated rats receive a single does of 50 mg pirnixic acid/kg and are killed 1, 2 or 3 days later; control rats are dosed with the vehicle alone. The mean absorbance developed at 415 nm over 10 min is presented on the y-axis. Error bars represent standard deviations of n=4 (1 day) and n=5 (2 and 3 day) rats per treatment. The extent of CDK expression the livers of young, male rats receiving a single does of 50 mg/kg of WY 14,643 increases steadily during the 3-day postdosing observation period. CDK expression in control animals remains constant over the same 3-day period.

Microtiter assay—As seen in FIG. 39, the extent of CDK expression in the livers of young, male rats receiving a single dose of 50 mg/kg of WY14,643 increases steadily during the 3-day postdosing observation period. CDK expression in control animals remains constant over the same 3-day period.

EXAMPLE 12

Enhanced expression of CDK in BNL CL.2 cell lysates 48 hours following exposure to the nongenotoxic carcinogen 2,3,7,8-tetrachlorodibenzo-p-dioxin Summary This example demonstrates the utility of the assay for the quantification of CDK response elicited by a test chemical in vitro following an exposure period of 48 hours.

It is demonstrated that exposure of BNL CL.2 cells to 0.1, 1, or 10 nM 2,3,7,8-tetrachlorodibenzo-p-dioxin for 48 hours in a low serum media enhances the expression of two cell lysate proteins, p34 and p33 immunoreactive with anti-cdc2 C-terminus antibody, compared to dimethylsulfoxide-treated controls. These results indicate that the early in vitro effects of the nongenotoxic carcinogen 2,3,7,8-tetrachlorodibenzo-p-dioxin can be quantified through a change in cellular CDK expression and therefore that stimulation of CDK is specific for nongenotoxic carcinogens.

Materials and Methods

Chemicals

This section is as previously described in Example 6.

Tissue culture cells, culture conditions and dosing

BNL CL.2 cells (ATCC TIB73) are purchased from American Type Culture Collection (Bethesda, Md.). These cells are representative of normal mouse hepatocytes. All other procedures were performed as detailed in Example 6.

The following concentrations and reagents are added to the appropriate tubes (4 plates/treatment). Dimethyl sulfoxide (DMSO) is used as the diluent for TCDD.

10 mL of DMEM+20% FBS-HI+0.1% DMSO (positive control)
10 mL of DMEM+0.5% FBS-HI+0.1% DMSO
10 mL of DMEM+0.5% FBS-HI+0.1 nM TCDD
10 mL of DMEM+0.5% FBS-HI+1.0 nM TCDD
10 mL of DMEM+0.5% FBS-HI+10 nM TCDD All plates were returned to the incubator for 48 h at the environmental conditions listed above. After the 48 h incubation period, the cells are harvested using the harvesting procedure described.

Gel electrophoresis and immunoblotting with anti-cdc2 C-terminus

These procedures are carried out as described in Example 1 except that anti-cdc2 C-terminus antibody is used in place of anti-PSTAIR antibody.

Protein determination

This procedure is performed as described in Example 1.

Results

Figure 40:
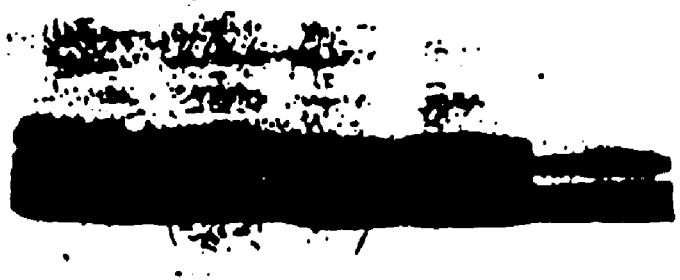
FIG. 40. Anti-cdc2 C-terminus immunoblot of BNL CL.2 cell lysate protein separated using 10 to 11% SDS-Page gels for BNL CL.2 cells exposed to 0.1, 1, or 10 nM 2,3,7,8-tetrachlorodibenzo-p-dioin (TCDD; lanes 8,9, and 10, respectively) or DMSO vehicle (lane 6) for 48 h in 0.5% serum supplemented media. Lane 7 is the 20% serum-supplemented control. TCDD exposure results in increased expression of CDK relative to the DMSO control.

Exposure of BNL CL2 cells to 0.1, 1, or 10 nM 2,3,7,8-tetrachlorodibenzo-p-dioxin (TCDD) for 48 h results in an increase in expression of anti-cdc2 C-terminus immunoreactive proteins p34 and p33 compared to the serum deprived DMSO control (FIG. 40, lanes 8,9 and 10 compared to lane 6). CDK protein expression at 10 nM TCDD was similar to that observed with serum stimulation (lane 10 compared to lane 7).

EXAMPLE 13

Testing Chemical Compounds or Test Samples for Nongenotoxic Carcinogens

The assays systems and methods disclosed in Examples 1–12 can be used to test chemical compounds, human and animal serum, air, water, and soil environmental samples for the presence of nongenotoxic carcinogens.

The above reagents, including antibodies, with or without aliquots of the cell lines described in the Examples may be packaged in the form of kits for the testing of suspected nongenotoxic carcinogens. Equivalent reagents, antibodies or cell lines may be substituted for the ones described in the Examples. In one preferred embodiment, a panel of three cell lines are included in the test kits. The three cell lines are a murine cell line, a rat cell line and a human cell line. Cell lines which are suitable for this purpose include murine BNL-CL.2 cells, a primary rat hepatic cell line developed by Paracelsian, Inc., PRLN-RH1, and a human hepatic cell line such as Hep G2 (ATCCG HB-8065).

Tissue samples, cells, and cell lysates from an individual person or animal can be substituted for the cell lines described, when testing for an individual's sensitivity to nongenotoxic carcinogens. Only reagents and antibodies would therefore be packaged in kits to test individual susceptibility.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

Literature Cited

1. Farber, E.(1991) Hepatocyte proliferation in stepwise development of experimental liver cell cancer. Dig. Diso Sci. 36, 973–978
2. Farber, E.(1984) The multistep nature of cancer development. Cancer Res 44, 4217–4223
3. Kanduc, D.; Aresta, A.; Quagliariello, E. and Farber, E. (1992) Effect of MNU on the methylation pattern of hepatic DNA during compensatory cell proliferation. Biochem. Biophys. Res Commun. 184, 107–111
4. Ames, B. N. (1984) The detection of environmental mutagens and potential carcinogens. Cancer 53, 2034–2040
5. MdCann, J. and Ames, B. N. (1976) Detection of carcinogens as mutagens in the Salmonella/microsome test: assay of 300 chemicals: discussion. Proc. Natl. Acad. Sci. U.S.A. 73, 950–954
6. Ames, B. N.; Durston, W. E.; Yamasaki, E. and Lee, F. D. (1973) Carcinogens are mutagens: a simple test system combining liver homogenates for activation and bacteria for detection. Proc. Natl. Acad. Sci. U.S.A. 70, 2281–2285
7. Ames, B. N.; Lee, F. D. and Durston, W. E. (1973) An improved bacterial test system for the detection and classification of mutagens and carcinogens. Proc. Natl. Acad. Sci. U.S.A. 70, 782–786
8. Ames, B. N. (1979) Identifying environmental chemicals causing mutations and cancer. Science 204, 587–593
9. Gold, L. S.; Slone, T. H.; Manley, N. B.; Garfinkel, G. B.; Hudes, E. S.; Rohrbach, L. and Ames, B. N. (1991) The Carcinogenic Potency Database: analyses of 4000 chronic animal cancer experiments published in the general literature and by the U.S. National Cancer Institute/National Toxicology Program. Environ. Health Perspect. 96, 11–15
10. Farber, E. (1988) Initiators, promoters and the uncertainty principle. Tumour. Biol. 9, 165–169
11. Farber, E. and Sarma, D. S. (1986) Chemical carcinogenesis: the liver as a model. Pathol. Immunopathol. Res 5, 1–28
12. Moslen, M. T.; Ahluwalia, M. B. and Farber, E. (1985) 1,2-Dibromoethane initiation of hepatic nodules in Sprague-Dawley rats selected with Solt-Farber system. Arch. Toxicol. 58, 118–119
13. Gold, L. S.; Bernstein, L. and Ames, B. N. (1990) The importance of ranking possible carcinogenic hazards using HERP. Risk. Anal. 10, 625–8; discussi
14. Busser, M. T. and Lutz, W. K. (1987) Stimulation of DNA synthesis in rat and mouse liver by various tumor promoters. Carcinogenesis 8, 1433–1437
15. Wolfle, D.; Munzel, P.; Fischer, G. and Bock, K. W. (1988) Altered growth control of rat hepatocytes after treatment with 3,4,3',4'-tetrachlorobiphenyl in vivo and in vitro. Carcinogenesis 9, 919–924
16. Chida, K.; Hashiba, H.; Sasaki, K. and Kuroki, T. (1986) Activation of protein kinase C and specific phosphorylation of a Mr 90,000 membrane protein of promotable BALB/3T3 and C3H/10T1/2 cells by tumor promoters. Cancer Res 46, 1055–1062
17. Smith, B. M. and Colburn, N. H. (1988) Protein kinase C and its substrates in tumor promoter-sensitive and —resistant cells. J. Biol. Chem. 263, 6424–6431
18. Novak-Hofer, I.; Kung, W.; Fabbro, D. and Eppenberger, U. (1987) Estrogen stimulates growth of mammary tumor cells ZR-75 without activation of S6 kinase and S6 phosphorylation. Difference from epidermal growth factor and alpha-transforming growth-factor-induced proliferation. Eur. J. Biochem. 164, 445–451
19. Hunter, T. (1987) A thousand and one protein kinases. Cell 50, 823–829
20. Hunter, T. and Cooper, J. A. (1985) Protein-tyrosine kinases. Annu. Rev. Biochem. 54, 897–930
21. Hunter, T.; Alexander, C. B. and Cooper, J. A. (1985) Protein phosphorylation and growth control. Ciba. Found. Symp. 116, 188–204
22. Yarden, Y. and Ullrich, A. (1988) Growth factor receptor tyrosine kinases. Annu. Rev. Biochem. 57, 443–478
23. Yarden, Y. and Ullrich, A. (1988) Molecular analysis of signal transduction by growth factors. Biochemistry 27, 3113–3119
24. Ullrich, A.; Riedel, H.; Yarden, Y.; Coussens, L.; Gray, A.; Dull, T.; Schlessinger, J.; Waterfield, M. D. and Parker, P. J. (1986) Protein kinases in cellular signal transduction: tyrosine kinase growth factor receptors and protein kinase C. Cold. Spring. Harb. Symp. Quant. Biol. 51 Pt 2, 713–724
25. Yarden, Y.; Kuang, W. J.; Yang-Feng, T.; Coussens, L.; Munemitsu, S.; Dull, T. J.; Chen, E.; Schlessinger, J.; Francke, U. and Ullrich, A. (1987) Human proto-oncogene c-kit: a new cell surface receptor tyrosine kinase for an unidentified ligand. EMBO J. 6, 3341–3351
26. Hunter, T. (1986) Cancer. Cell growth control mechanisms [news]. Nature 322, 14–16
27. Funasaka, Y.; Boulton, T.; Cobb, M.; Yarden, Y.; Fan, B.; Lyman, S. D.; Williams, D. E.; Anderson, D. M.; Zakut, R.; Mishima, Y. and et al, (1992) c-Kit-kinase induces a cascade of protein tyrosine phosphorylation in normal human melanocytes in response to mast cell growth factor and stimulates mitogen-activated protein kinase but is down-regulated in melanomas. Mol. Biol. Cell 3, 197–209
28. Bouton, A. H.; Kanner, S. B.; Vines, R. R. and Parsons, J. T. (1991) Tyrosine phosphorylation of three cellular proteins correlates with transformation of rat 1 cells by pp61src. Mol. Carcinog. 4, 145–152
29. Arion, D.; Meijer, L.; Brizuela, L. and Beach, D. (1988) cdc2 is a component of the M phase-specific histone H1 kinase: evidence for identity with MPF. Cell 55, 371–378
30. Arion, D. and Meijer, L. (1989) M-phase-specific protein kinase from mitotic sea urchin eggs: cyclic activation depends on protein synthesis and phosphorylation but does not require DNA or RNA synthesis. Exp. Cell Res 183, 361–375
31. Maller Jl;, ; Gautier, J.; Langan, T. A.; Lohka, M. J.; Shenoy, S.; Shalloway, D. and Nurse, P., (1989) Maturation-promoting factor and the regulation of the cell cycle. J. Cell Sci. Suppl. 12, 53–63
32. Ma, X. F.; Gibbons, J. A. and Babish, J. G. (1991) Benzo[e]pyrene pretreatment of immature, female C57BL/6J mice results in increased bioactivation of aflatoxin B1 in vitro. Toxicol. Lett. 59, 51–58
33. Laemmli, U. K. and Favre, M. (1973) Maturation of the head of bacteriophage T4. I. DNA packaging events. J. Mol. Biol. 80, 575–599
34. Towbin, H.; Staehelin, T. and Gordon, J. (1979) Electrophoretic transfer of proteins from polyacrylamide gels to nitrocellulose sheets: procedure and some applications. Proc. Natl. Acad. Sci. U.S.A. 76, 4350–4354
35. Smith, P. K.; Krohn, R. I.; Hermanson, G. T.; Mallia, A. K.; Gartner, F. H.; Provenzano, M. D.; Fujimoto, E. K.; Goeke, N. M.; Olson, B. J. and Klenk, D. C. (1985) Measurement of protein using bicinchoninic acid [published erratum appears in Anal Biochem 1987 May 15;163(1):279]. Anal. Biochem. 150, 76–85
36. Elledge, S. J. and Spottswood, M. R. (1991) A new human p34 protein kinase, CDK2, identified by complementation of a cdc28 mutation in Saccharomyces cerevisiae, is a homolog of Xenopus Eg1. EMBO J. 10, 2653–2659
37. Brizuela, L.; Draetta, G. and Beach, D. (1989) Activation of human CDC2 protein as a histone H1 kinase is associated with complex formation with the p62 subunit Proc. Natl. Acad. Sci. U.S.A. 86, 4362–4366
38. Draetta, G.; Luca, F.; Westendorf, J.; Brizuela, L.; Ruderman, J. and Beach, D. (1989) Cdc2 protein kinase is complexed with both cyclin A and B: evidence for proteolytic inactivation of MPF. Cell 56, 829–838
39. Sjolander, S. and Urbaniczky, C. (1991) Integrated fluid handling system for biomolecular interaction analysis. Anal. Chem. 63, 2338–2345
40. Altschuh, D.; Dubs, M. C.; Weiss, E.; Zeder-Lutz, G. and Van Regenmortel, M. H. (1992) Determination of kinetic constants for the interaction between a monoclonal antibody and peptides using surface plasmon resonance. Biochemistry 31, 6298–6304
41. Dubs, M. C.; Altschuh, D. and Van Regenmortel, M. H. (1992) Mapping of viral epitopes with conformationally specific monoclonal antibodies using biosensor technology. J. Chromatogr. 597, 391–396
42. Dubs, M. C.; Altschuh, D. and Van Regenmortel, M. H. (1992) Interaction between viruses and monoclonal antibodies studied by surface plasmon resonance. Immunol. Lett. 31, 59–64
43. Draetta, G. and Beach, D. (1988) Activation of cdc2 protein kinase during mitosis in human cells cell cycle-dependent phosphorylation and subunit rearrangement. Cell 54, 17–26
44. Ducommun, B.; Brambilla, P.; Felix, M. A.; Franza, B. R. Jr.; Karsenti, E. and Draetta, G. (1991) cdc2 phosphorylation is required for its interaction with cyclin. EMBO J. 10, 3311–3319
45. Draetta, G. and Beach, D. (1989) The mammalian cdc2 protein kinase: mechanisms of regulation during the cell cycle. J. Cell Sci. Suppl. 12, 21–27
46. Draetta, G. (1990) Cell cycle control in eukaryotes: molecular mechanisms of cdc2 activation. Trends. Biochem. Sci. 15, 378–383

47. Norla, A. O.; Draetta, G.; Beach, D. and Wang, J. Y. (1989) Reversible tyrosine phosphorylation of cdc2 dephosphorylation accompanies activation during entry into mitosis. Cell 58, 193–203
48. Draetta, G.; Piwnica-Worms, H.; Morrison, D.; Druker, B.; Roberts, T. and Beach, D. (1988) Human cdc2 protein kinase is a major cell-cycle regulated tyrosine kinase substrate. Nature 336, 738–744

---

---

What is claimed is:

1. An assay to screen whether a test chemical or sample is a nongenotoxic carcinogen comprising:
   a) adding the test chemical compound or sample to an assay system selected from the group consisting of an animal, a cell culture, and a panel of cell lines, which expresses at least one cyclin dependent kinase (CDK);
   b) measuring the level of at least one tyrosylphosphorylated CDK; and
   c) detecting an increase in the level of said tyrosylphosphorylated CDK when the test compound or sample is a nongenotoxic, carcinogen.

2. The assay according to claim 1, wherein the nongenotoxic carcinogen is selected from the group consisting of chlorinated biphenyls, hormones, dioxins and peroxisome proliferators.

3. The assay according to claim 1, wherein the nongenotoxic carcinogen is a tumor promoter.

4. The assay according to claim 1, wherein the nongenotoxic carcinogen is nonmutagenic.

5. The assay of claim 1, wherein the CDK is p34$^{cdc2}$.

6. The assay of claim 5, wherein the CDK is detectable on a polyacrylamide gel at a band from about 32 to about 34 kDa.

7. The assay of claim 1, wherein the animal is a rodent.

8. The assay of claim 1, wherein the panel of cell lines is a murine cell line, a rat cell line and a human cell line.

9. The assay of claim 1, wherein the cell culture is a 3T3 cell culture.

10. The assay of claim 1, wherein the cell culture is a BNL-CL.2 cell culture.

11. A method to screen whether a test sample contains a nongenotoxic carcinogen comprising:
   a) adding an aliquot of the test sample to an assay system selected from the group consisting of an animal a cell culture, which expresses at least one cyclin dependent kinase (CDK);
   b) measuring the level of at least one tyrosylphosphorylated CDX; and
   c) detecting an increase in the level of said tyrosylphosphorylated CDK when the test sample is a nongenotoxic carcinogen.

12. The method according to claim 11, wherein the nongenotoxic carcinogen is selected from the group consisting of chlorinated biphenyls, hormones, dioxins and peroxisome proliferators.

13. The method according to claim 11, wherein the nongenotoxic carcinogen is a tumor promoter.

14. The method according to claim 11, wherein the nongenotoxic carcinogen is also nonmutagenic.

* * * * *

UNITED STATES PATENT AND TRADEMARK OFFICE
CERTIFICATE OF CORRECTION

PATENT NO. : 5,955,289
DATED : September 21, 1999
INVENTOR(S) : Xinfang Ma. et al It is certified that error appears in the above-identified patent and that said Letters Patent is hereby corrected as shown below:

On the title page, item [73] Assignee, change the assignee to
-- Paracelsian, Inc. --

Signed and Sealed this

First Day of February, 2000

Attest:

Attesting Officer

Q. TODD DICKINSON

Acting Commissioner of Patents and Trademarks

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 6 amino acids
      (B) TYPE: amino acid
      (C) STRANDEDNESS: single
      (D) TOPOLOGY: linear (xi) SEQUENCE DESCRIPTION: SEQ ID NO:1:

Pro Ser Thr Ala Ile Arg
1          5